(12) United States Patent
Cherqui

(10) Patent No.: US 12,012,437 B2
(45) Date of Patent: *Jun. 18, 2024

(54) METHODS OF TREATING MITOCHONDRIAL DISORDERS

(71) Applicant: The Regents of the University of California, Oakland, CA (US)

(72) Inventor: Stephanie Cherqui, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 17/484,324

(22) Filed: Sep. 24, 2021

(65) Prior Publication Data

US 2022/0009977 A1    Jan. 13, 2022

Related U.S. Application Data

(62) Division of application No. 16/082,487, filed as application No. PCT/US2017/022447 on Mar. 15, 2017.

(60) Provisional application No. 62/312,105, filed on Mar. 23, 2016.

(51) Int. Cl.
| C07K 14/47 | (2006.01) |
| A01K 67/0276 | (2024.01) |
| A01K 67/0278 | (2024.01) |
| A61K 35/28 | (2015.01) |
| A61P 25/28 | (2006.01) |
| C12N 9/22 | (2006.01) |
| C12N 15/11 | (2006.01) |
| C12N 15/86 | (2006.01) |

(52) U.S. Cl.
CPC .......... *C07K 14/47* (2013.01); *A01K 67/0276* (2013.01); *A01K 67/0278* (2013.01); *A61K 35/28* (2013.01); *A61P 25/28* (2018.01); *C12N 9/22* (2013.01); *C12N 15/11* (2013.01); *C12N 15/86* (2013.01); *A01K 2207/15* (2013.01); *A01K 2217/05* (2013.01); *A01K 2217/075* (2013.01); *A01K 2217/15* (2013.01); *A01K 2227/105* (2013.01); *A01K 2267/0318* (2013.01); *C07K 2319/60* (2013.01); *C12N 2310/20* (2017.05); *C12N 2740/16043* (2013.01); *C12N 2800/80* (2013.01)

(58) Field of Classification Search
None
See application file for complete search history.

(56) References Cited

U.S. PATENT DOCUMENTS

| 9,066,966 | B2 | 6/2015 | Puccio et al. |
| 10,617,770 | B2 | 4/2020 | Corti et al. |
| 2007/0031847 | A1 | 2/2007 | Cargill et al. |
| 2008/0050393 | A1 | 2/2008 | Tang et al. |
| 2014/0142160 | A1 | 5/2014 | Lee et al. |
| 2014/0315782 | A1 | 10/2014 | Tremblay et al. |
| 2015/0225722 | A1 | 8/2015 | Ozsolak |
| 2016/0237455 | A1* | 8/2016 | Glucksmann .......... C12N 15/85 |
| 2016/0340661 | A1 | 11/2016 | Cong et al. |
| 2016/0340662 | A1 | 11/2016 | Zhang et al. |
| 2016/0354487 | A1 | 12/2016 | Zhang et al. |
| 2016/0355796 | A1 | 12/2016 | Davidson et al. |
| 2016/0355797 | A1 | 12/2016 | Konermann et al. |
| 2017/0128528 | A1 | 5/2017 | Samulski |
| 2018/0170985 | A1 | 6/2018 | Tremblay et al. |
| 2018/0344817 | A1 | 12/2018 | Smith et al. |
| 2019/0119337 | A1 | 4/2019 | Cherqui |
| 2020/0056206 | A1 | 2/2020 | Tremblay et al. |

FOREIGN PATENT DOCUMENTS

| WO | WO-2014/118346 A1 | 8/2014 |
| WO | WO-2015/089462 | 6/2015 |
| WO | WO-2017/015245 A1 | 1/2017 |

OTHER PUBLICATIONS

Ouellet et al. 128. Deletion of GAA Repeats Expansion from the Intron 1 of the Frataxin Gene Using CRISPR/Cas9 System, Molecular Therapy, May 2015; 23(1): pp. S52-S53. (Year: 2015).*
"Mitochondrion", Wikipedia, downloaded Jun. 21, 2022 (23 pages).
Vannocci et al., "A new cellular model to follow Friedreich's ataxia development in a time-resolved way" The Company of Biologists Ltd, Disease Models & Mechanisms, Jul. 1, 2015, 8(7):711-719.
Al-Mahdawi, et al., GAA repeat instability in Friedreich ataxia YAC transgenic mice. Genomics 84, 301-310 (2004).
Buyse et al. Idebenone treatment in Friedreich's ataxia: neurological, cardiac, and biochemical monitoring. Neurology. May 27, 2003;60(10):1679-81.
Campuzano, et al., Frataxin is reduced in Friedreich ataxia patients and is associated with mitochondrial membranes. Human molecular genetics 6, 1771-1780 (1997).
Capotondo et al. Brain conditioning is instrumental for successful microglia reconstitution following hematopoietic stem cell transplantation. Proc Natl Acad Sci U S A. Sep. 11, 2012;109(37):15018-23. Epub Aug. 23, 2012.
EP17770835.1 Extended European Search Report mailed Oct. 4, 2019.
Gaide Chevronnay et al. Hematopoietic Stem Cells Transplantation Can Normalize Thyroid Function in a Cystinosis Mouse Model. Endocrinology. Apr. 2016;157(4):1363-71. Epub Jan. 26, 2016.

(Continued)

Primary Examiner — Allison M Fox
Assistant Examiner — Alyssa G Weston
(74) Attorney, Agent, or Firm — Foley & Lardner LLP

(57) ABSTRACT

Provided herein are methods for treating a disease or disorder associated with mitochondrial dysfunction through ex vivo introduction of a nucleic acid molecule into hematopoietic stem and progenitor cells (HSPCs) followed by transplantation of the HSPCs into a subject in need of treatment. The nucleic acid molecule may include a functional human frataxin (hFXN) or may include a gene editing system that when transfected into the cells removes a trinucleotide extension mutation of endogenous hFXN.

14 Claims, 20 Drawing Sheets

Specification includes a Sequence Listing.

(56) References Cited

OTHER PUBLICATIONS

Harrison et al. Hematopoietic stem cell gene therapy for the multisystemic lysosomal storage disorder cystinosis. Mol Ther. Feb. 2013;21(2):433-44. Epub Oct. 23, 2012.
J Torres-Torronteras et al, "Hematopoietic gene therapy restores thymidine phosphorylase activity in a cell culture and a murine model of MNGIE", Gene Therapy, (2011), vol. 18, No. 8, pp. 795-806.
Jones et al. Mesenchymal stem cells improve motor functions and decrease neurodegeneration in ataxic mice. Mol Ther. Jan. 2015;23(1):130-8. Epub Jul. 29, 2014.
Li, et al., "Excision of Expanded GAA Repeats Alleviates the Molecular Phenotype of Friedreich's Ataxia", Molecular Therapy, Jun. 2015, vol. 23, No. 6, pp. 1055-1065.
Naphade et al. Brief reports: Lysosomal cross-correction by hematopoietic stem cell-derived macrophages via tunneling nanotubes. Stem Cells. Jan. 2015;33(1):301-9.
PCT/US2017/022447 International Search Report and written Opinion mailed Aug. 11, 2017.
Perez-Luz, et al., Delivery of the 135 kb human frataxin genomic DNA locus gives rise to different frataxin isoforms. Genomics 106, 76-82 (2015)May 2015.
Peterson et al. Long-term multilineage engraftment of autologous genome-edited hematopoietic stem cells in nonhuman primates. Blood. May 19, 2016;127(20):2416-26. Epub Mar. 15, 2016.
Rahman. Emerging aspects of treatment in mitochondrial disorders. J Inherit Metab Dis. Jul. 2015;38(4):641-53. Epub May 12, 2015.
Rocca et al. Transplantation of wild-type mouse hematopoietic stem and progenitor cells ameliorates deficits in a mouse model of Friedreich's ataxia. Sci Transl Med. Oct. 25, 2017;9(413):eaaj2347.
Shen et al. Frataxin Deficiency Promotes Excess Microglial DNA Damage and Inflammation that Is Rescued by PJ34. PLoS One. Mar. 8, 2016;11(3):e0151026.
Vallabhaneni et al. Vascular smooth muscle cells initiate proliferation of mesenchymal stem cells by mitochondrial transfer via tunneling nanotubes. Stem Cells Dev. Nov. 20, 2012;21(17):3104-13. Epub Jul. 13, 2012.
Vanhee, S et al., "Pluripotent Stem Cell based Gene Therapy for Hematological Diseases", Critical Reviews in Oncology/Hematology, (Sep. 14, 2015), vol. 97, pp. 238-246.
International Search Report and Written Opinion dated Sep. 16, 2021, from application No. PCT/US2021/021850.
Cradick et al., "COSMID: A Web-based Tool for Identifying and Validating CRISPR/Cas Off-target Sites", Molecular Therapy-Nucleic Acids, Dec. 2, 2014, 3, e214, 10 pages.
Doench et al., "Optimized sgRNA design to maximize activity and minimize off-target effects of CRISPR-Cas9", Nature Biotechnology, Feb. 2016, 34(2), pp. 184-191.
Evans-Galea et al., "Cell and Gene Therapy for Friedreich Ataxia: Progress to Date", Human Gene Therapy, Aug. 2014 25(8), pp. 684-693.
Pastore et al., "Frataxin: a protein in search for a function", Journal of Neurochemistry, Aug. 2013, Suppl 1, pp. 43-52.
Tajiri et al., "Autologous Stem Cell Transplant with Gene Therapy for Friedreich Ataxia", Med Hypotheses, Sep. 2014, 83(3), pp. 296-298.
US Non-Final Office Action dated Mar. 28, 2023, for U.S. Appl. No. 16/082,487.
US Non-Final Office Action dated May 1, 2023, for U.S. Appl. No. 16/820,368.
Van Maele et al., "Impact of the Central Polypurine Tract on the Kinetics of Human Immunodeficiency Virus Type 1 Vector Transduction", Journal of Virology, Apr. 2003, vol. 77, No. 8, pp. 4685-4694.
US Final Office Action dated Aug. 18, 2023, for U.S. Appl. No. 16/082,487.
US Final Office Action dated Sep. 13, 2023, for U.S. Appl. No. 16/820,368.
Zaibak et al., "Integration of functional bacterial artificial chromosomes into human cord blood-derived multipotent stem cells", Gene Therapy, Mar. 2009, vol. 16, No. 3, pp. 404-414.
US Notice of Allowance dated Apr. 10, 2024, for U.S. Appl. No. 16/820,368.
US Notice of Allowance dated Mar. 28, 2024, for U.S. Appl. No. 16/082,487.

* cited by examiner

Unaffected

FRDA

WT

YG8R

YG8R/YG8R HSPCs

YG8R/WT HSPCs

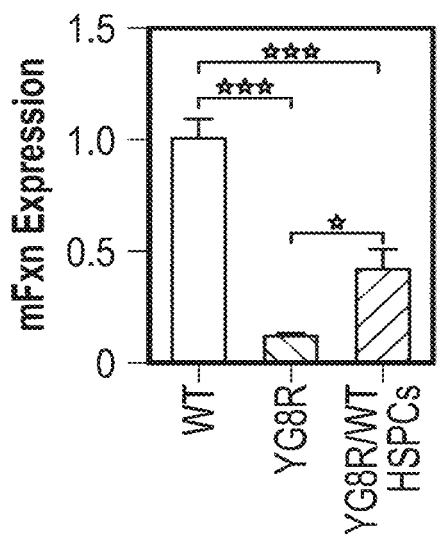 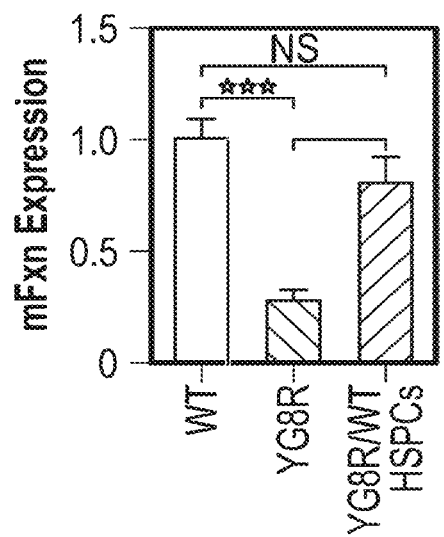
FIG. 3D  FIG. 3E
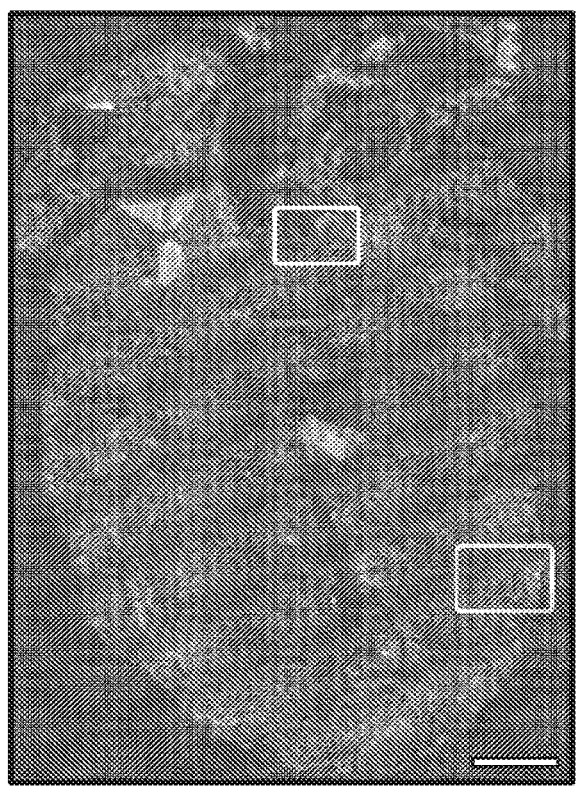 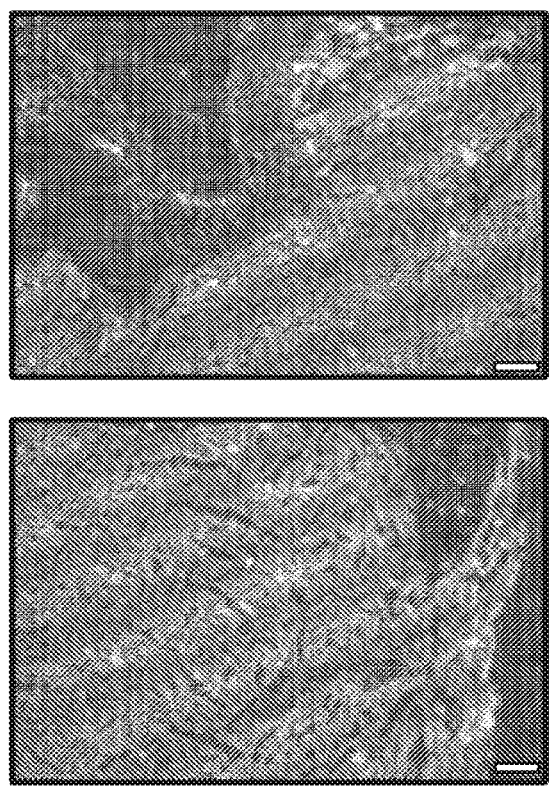
FIG. 3F

SEQUENCE LISTING

```
<160> NUMBER OF SEQ ID NOS: 16

<210> SEQ ID NO 1
<211> LENGTH: 1504
<212> TYPE: DNA
<213> ORGANISM: Homo sapiens
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (92)..(92)
<223> OTHER INFORMATION: a, c, t, g, unknown or other
<220> FEATURE:
<221> NAME/KEY: modified_base
<222> LOCATION: (167)..(167)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other

<400> SEQUENCE: 1
tttacagggc ataactcatt ttatccttac cacaatccta tgaagtagga acttttataa      60
aacgcatttt atatncaagg gcacagagag gntaattaac ttgccctctg gtcacacagc     120
taggaagtgg gcagagtaca gatttacact aggcatccgt ctcctgnccc cacatancca     180
gctgctgtaa acccataccg gcggccaagc agcctcaatt tgtgcatgca cccacttccc     240
agcaagacag cagctcccaa gttcctcctg tttagaattt tagaagcggc gggccaccag     300
gctgcagtct cccttgggtc aggggtcctg gttgcactcc gtgctttgca caaagcaggc     360
tctccatttt tgttaaatgc acgaatagtg ctaagctggg aagttcttcc tgaggtctaa     420
```

```
cctctagctg ctcccccaca gaagagtgcc tgcggccagt ggccaccagg ggtcgccgca      480
gcacccagcg ctggagggcg gagcgggcgg cagacccgga gcagcatgtg actctcgggc      540
gccgcgcagt agccggcctc ctggcgtcac ccagcccggc ccaggcccag accctcaccc      600
gggtcccgcg gccggcagag ttggccccac tctgcggccg ccgtggcctg cgcaccgaca      660
tcgatgcgac ctgcacgccc cgccgcgcaa gttcgaacca acgtggcctc aaccagattt      720
ggaatgtcaa aaagcagagt gtctatttga tgaatttgag gaaatctgga actttgggcc      780
acccaggctc tctagatgag accacctatg aaagactagc agaggaaacg ctggactctt      840
tagcagagtt ttttgaagac cttgcagaca agccatacac gtttgaggac tatgatgtct      900
cctttgggag tggtgtctta actgtcaaac tgggtggaga tctaggaacc tatgtgatca      960
acaagcagac gccaaacaag caaatctggc tatcttctcc atccagtgga cctaagcgtt     1020
atgactggac tgggaaaaac tgggtgttct cccacgacgg cgtgtccctc catgagctgc     1080
tggccgcaga gctcactaaa gcctaaaaaa ccaaactgga cttgtcttgg ttggcctatt     1140
ccggaaaaga tgcttgatgc ccagccccgt tttaaggaca ttaaaagcta tcaggccaag     1200
accccagctt cattatgcag ctgaggtgtg tttttttgttg ttgttgttgt ttattttttt     1260
tattcctgct tttgaggaca cttgggctat gtgtcacagc tctgtacaaa caatgtgttg     1320
cctcctacct tgcccccaag ttctgatttt taatttctat ggaagatttt ttggattgtc     1380
ggatttcctc cctcacatga tacccttat cttttataat gtcttatgcc tatacctgaa     1440
tataacaacc tttaaaaaag caaataata agaaggaaaa attccaggag ggaaaaaaaa     1500
aaaa                                                                 1504

<210> SEQ ID NO 2
<211> LENGTH: 633
<212> TYPE: DNA
<213> ORGANISM: Homo sapiens

<400> SEQUENCE: 2
atgtggactc tcgggcgccg cgcagtagcc ggcctcctgg cgtcacccag cccggcccag       60
gcccagaccc tcacccgggt cccgcggccg gcagagttgg ccccactctg cggccgccgt      120
ggcctgcgca ccgacatcga tgcgacctgc acgccccgcc gcgcaagttc gaaccaacgt      180
ggcctcaacc agatttggaa tgtcaaaaag cagagtgtct atttgatgaa tttgaggaaa      240
tctggaactt tgggccaccc aggctctcta gatgagacca cctatgaaag actagcagag      300
gaaacgctgg actctttagc agagtttttt gaagaccttg cagacaagcc atacacgttt      360
gaggactatg atgtctccct tgggagtggt gtcttaactg tcaaactggg tggagatcta      420
ggaacctatg tgatcaacaa gcagacgcca aacaagcaaa tctggctatc ttctccatcc      480
agtggaccta agcgttatga ctggactggg aaaaactggg tgttctccca cgacggcgtg      540
tccctccatg agctgctggc cgcagagctc actaaagcct aaaaaccaa actggacttg      600 tcttggttgg cctattccgg aaaagatgct tga                                  633

<210> SEQ ID NO 3
<211> LENGTH: 1096
<212> TYPE: DNA
<213> ORGANISM: Mus musculus

<400> SEQUENCE: 3
cggccgcgga gctggagtag catgtgggcg ttcggaggtc gcgcagccgt gggcttgctg       60
```

```
ccccggacgg cgtcccgggc ctccgcctgg gtcgggaacc cgcgctggag ggaaccgatc    120
gtaacctgcg gccgccgagg cctacatgtc acagtcaacg ccggcgccac cgccacgcc     180 catttgaacc tccactacct ccagattctg aacatcaaaa agcagagcgt ctgcgtggtg    240
catttgagga acttggggac attggacaac ccaagctctc tagacgagac agcgtatgaa    300
agactggcgg aagagaccct ggactccctg gccgagttct ttgaagacct cgcagacaag    360
ccctataccc tggaggacta cgatgtctct tttggggatg cgtgctcac cattaagctg     420 ggcggggatc tagggaccta cgtgatcaac aagcagaccc caaacaagca aatctggctg    480
tcttctcctt ccagcggccc caagcgctat gactggaccg ggaagaactg ggtgtactct    540
catgacggcg tgtctctgca tgagctgctg gccagggagc tgactaaagc tttaaacacc    600
aaactggact tgtcttcatt ggcctattct ggaaaaggca cttgactgcc agccagattc    660
caagacatta aacactgtca ggtgaagacc cccagcctcc tcctgtagct gaatgtctgc    720
cttcccatac ctgctcctga agatagtcac accgtgtgtg acagtctgt gaaaaaagtg     780 tgttccctcc cacccctgtcc ccggacctgg ctcttcattt ctacagacat tgttaggat    840 tatgtcattt gctccccaac ctgagacctc tggtctctta gaaagtctta tatgctgggc    900
agtggtggcg cacgccttta atcccagcac tcggaggca gaggcaggcg gatttctgag     960
ttggaggcca gcctggttta cagagtgagt tccaggacag ccaggactac acagagaaac   1020
cctgtgtcga aaaaaaaaa aaaaaaaga aagaaagaaa gtcttacacc acaagtgtgt    1080
ccatgatata acagcc                                                   1096

<210> SEQ ID NO 4
<211> LENGTH: 624
<212> TYPE: DNA
<213> ORGANISM: Mus musculus

<400> SEQUENCE: 4
atgtgggcgt tcggaggtcg cgcagccgtg ggcttgctgc cccggacggc gtcccgggcc     60
tccgcctggg tcgggaaccc gcgctggagg gaaccgatcg taacctgcgg ccgccgaggc   120
ctacatgtca cagtcaacgc cggcgccacc cgccacgccc atttgaacct ccactacctc   180
cagattctga acatcaaaaa gcagagcgtc tgcgtggtgc atttgaggaa cttggggaca   240
ttggacaacc caagctctct agacgagaca gcgtatgaaa actggcgga agagaccctg    300 gactccctgg ccgagttctt tgaagacctc gcagacaagc cctataccct ggaggactac   360
gatgtctctt ttggggatgg cgtgctcacc attaagctgg gcggggatct agggacctac   420
gtgatcaaca agcagacccc aaacaagcaa atctggctgt cttctccttc cagcggcccc   480
aagcgctatg actggaccgg gaagaactgg gtgtactctc atgacggcgt gtctctgcat   540
gagctgctgg ccagggagct gactaaagct ttaaacacca aactggactt gtcttcattg   600
gcctattctg gaaaaggcac ttga                                           624

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttccctcta ccctgccttc                                                 20
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggagaacagt ggacacagta aca                                             23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catcgccttc tatcgccttc t                                               21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggcagataa aggaaggaga tac                                             23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgatagggc aacaccaata a                                               21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttaggatcca tgtggactct cg                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaggatcca gcatcttttc cg                                              22

```
<210> SEQ ID NO 12
<211> LENGTH: 5100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5100)
<223> OTHER INFORMATION: This sequence may encompass 90-1700 'gaa'
      repeating units

<400> SEQUENCE: 12
```

| | | | | | |
|---|---|---|---|---|---|
| gaagaagaag | aagaagaaga | agaagaagaa | gaagaagaag | aagaagaaga | agaagaagaa     60 |
| gaagaagaag | aagaagaaga | agaagaagaa | gaagaagaag | aagaagaaga | agaagaagaa    120 |
| gaagaagaag | aagaagaaga | agaagaagaa | gaagaagaag | aagaagaaga | agaagaagaa    180 |
| gaagaagaag | aagaagaaga | agaagaagaa | gaagaagaag | aagaagaaga | agaagaagaa    240 |
| gaagaagaag | aagaagaaga | agaagaagaa | gaagaagaag | aagaagaaga | agaagaagaa    300 |
| gaagaagaag | aagaagaaga | agaagaagaa | gaagaagaag | aagaagaaga | agaagaagaa    360 |
| gaagaagaag | aagaagaaga | agaagaagaa | gaagaagaag | aagaagaaga | agaagaagaa    420 |
| gaagaagaag | aagaagaaga | agaagaagaa | gaagaagaag | aagaagaaga | agaagaagaa    480 |
| gaagaagaag | aagaagaaga | agaagaagaa | gaagaagaag | aagaagaaga | agaagaagaa    540 |
| gaagaagaag | aagaagaaga | agaagaagaa | gaagaagaag | aagaagaaga | agaagaagaa    600 |
| gaagaagaag | aagaagaaga | agaagaagaa | gaagaagaag | aagaagaaga | agaagaagaa    660 |
| gaagaagaag | aagaagaaga | agaagaagaa | gaagaagaag | aagaagaaga | agaagaagaa    720 |
| gaagaagaag | aagaagaaga | agaagaagaa | gaagaagaag | aagaagaaga | agaagaagaa    780 |
| gaagaagaag | aagaagaaga | agaagaagaa | gaagaagaag | aagaagaaga | agaagaagaa    840 |
| gaagaagaag | aagaagaaga | agaagaagaa | gaagaagaag | aagaagaaga | agaagaagaa    900 |
| gaagaagaag | aagaagaaga | agaagaagaa | gaagaagaag | aagaagaaga | agaagaagaa    960 |
| gaagaagaag | aagaagaaga | agaagaagaa | gaagaagaag | aagaagaaga | agaagaagaa   1020 |
| gaagaagaag | aagaagaaga | agaagaagaa | gaagaagaag | aagaagaaga | agaagaagaa   1080 |
| gaagaagaag | aagaagaaga | agaagaagaa | gaagaagaag | aagaagaaga | agaagaagaa   1140 |
| gaagaagaag | aagaagaaga | agaagaagaa | gaagaagaag | aagaagaaga | agaagaagaa   1200 |
| gaagaagaag | aagaagaaga | agaagaagaa | gaagaagaag | aagaagaaga | agaagaagaa   1260 |
| gaagaagaag | aagaagaaga | agaagaagaa | gaagaagaag | aagaagaaga | agaagaagaa   1320 |
| gaagaagaag | aagaagaaga | agaagaagaa | gaagaagaag | aagaagaaga | agaagaagaa   1380 |
| gaagaagaag | aagaagaaga | agaagaagaa | gaagaagaag | aagaagaaga | agaagaagaa   1440 |
| gaagaagaag | aagaagaaga | agaagaagaa | gaagaagaag | aagaagaaga | agaagaagaa   1500 |
| gaagaagaag | aagaagaaga | agaagaagaa | gaagaagaag | aagaagaaga | agaagaagaa   1560 |
| gaagaagaag | aagaagaaga | agaagaagaa | gaagaagaag | aagaagaaga | agaagaagaa   1620 |
| gaagaagaag | aagaagaaga | agaagaagaa | gaagaagaag | aagaagaaga | agaagaagaa   1680 |
| gaagaagaag | aagaagaaga | agaagaagaa | gaagaagaag | aagaagaaga | agaagaagaa   1740 |
| gaagaagaag | aagaagaaga | agaagaagaa | gaagaagaag | aagaagaaga | agaagaagaa   1800 |
| gaagaagaag | aagaagaaga | agaagaagaa | gaagaagaag | aagaagaaga | agaagaagaa   1860 |
| gaagaagaag | aagaagaaga | agaagaagaa | gaagaagaag | aagaagaaga | agaagaagaa   1920 |

-continued

```
gaagaagaag aagaagaaga agaagaagaa gaagaagaag aagaagaaga agaagaagaa      1980
gaagaagaag aagaagaaga agaagaagaa gaagaagaag aagaagaaga agaagaagaa      2040
gaagaagaag aagaagaaga agaagaagaa gaagaagaag aagaagaaga agaagaagaa      2100
gaagaagaag aagaagaaga agaagaagaa gaagaagaag aagaagaaga agaagaagaa      2160
gaagaagaag aagaagaaga agaagaagaa gaagaagaag aagaagaaga agaagaagaa      2220
gaagaagaag aagaagaaga agaagaagaa gaagaagaag aagaagaaga agaagaagaa      2280
gaagaagaag aagaagaaga agaagaagaa gaagaagaag aagaagaaga agaagaagaa      2340
gaagaagaag aagaagaaga agaagaagaa gaagaagaag aagaagaaga agaagaagaa      2400
gaagaagaag aagaagaaga agaagaagaa gaagaagaag aagaagaaga agaagaagaa      2460
gaagaagaag aagaagaaga agaagaagaa gaagaagaag aagaagaaga agaagaagaa      2520
gaagaagaag aagaagaaga agaagaagaa gaagaagaag aagaagaaga agaagaagaa      2580
gaagaagaag aagaagaaga agaagaagaa gaagaagaag aagaagaaga agaagaagaa      2640
gaagaagaag aagaagaaga agaagaagaa gaagaagaag aagaagaaga agaagaagaa      2700
gaagaagaag aagaagaaga agaagaagaa gaagaagaag aagaagaaga agaagaagaa      2760
gaagaagaag aagaagaaga agaagaagaa gaagaagaag aagaagaaga agaagaagaa      2820
gaagaagaag aagaagaaga agaagaagaa gaagaagaag aagaagaaga agaagaagaa      2880
gaagaagaag aagaagaaga agaagaagaa gaagaagaag aagaagaaga agaagaagaa      2940
gaagaagaag aagaagaaga agaagaagaa gaagaagaag aagaagaaga agaagaagaa      3000
gaagaagaag aagaagaaga agaagaagaa gaagaagaag aagaagaaga agaagaagaa      3060
gaagaagaag aagaagaaga agaagaagaa gaagaagaag aagaagaaga agaagaagaa      3120
gaagaagaag aagaagaaga agaagaagaa gaagaagaag aagaagaaga agaagaagaa      3180
gaagaagaag aagaagaaga agaagaagaa gaagaagaag aagaagaaga agaagaagaa      3240
gaagaagaag aagaagaaga agaagaagaa gaagaagaag aagaagaaga agaagaagaa      3300
gaagaagaag aagaagaaga agaagaagaa gaagaagaag aagaagaaga agaagaagaa      3360
gaagaagaag aagaagaaga agaagaagaa gaagaagaag aagaagaaga agaagaagaa      3420
gaagaagaag aagaagaaga agaagaagaa gaagaagaag aagaagaaga agaagaagaa      3480
gaagaagaag aagaagaaga agaagaagaa gaagaagaag aagaagaaga agaagaagaa      3540
gaagaagaag aagaagaaga agaagaagaa gaagaagaag aagaagaaga agaagaagaa      3600
gaagaagaag aagaagaaga agaagaagaa gaagaagaag aagaagaaga agaagaagaa      3660
gaagaagaag aagaagaaga agaagaagaa gaagaagaag aagaagaaga agaagaagaa      3720
gaagaagaag aagaagaaga agaagaagaa gaagaagaag aagaagaaga agaagaagaa      3780
gaagaagaag aagaagaaga agaagaagaa gaagaagaag aagaagaaga agaagaagaa      3840
gaagaagaag aagaagaaga agaagaagaa gaagaagaag aagaagaaga agaagaagaa      3900
gaagaagaag aagaagaaga agaagaagaa gaagaagaag aagaagaaga agaagaagaa      3960
gaagaagaag aagaagaaga agaagaagaa gaagaagaag aagaagaaga agaagaagaa      4020
gaagaagaag aagaagaaga agaagaagaa gaagaagaag aagaagaaga agaagaagaa      4080
gaagaagaag aagaagaaga agaagaagaa gaagaagaag aagaagaaga agaagaagaa      4140
gaagaagaag aagaagaaga agaagaagaa gaagaagaag aagaagaaga agaagaagaa      4200
gaagaagaag aagaagaaga agaagaagaa gaagaagaag aagaagaaga agaagaagaa      4260
gaagaagaag aagaagaaga agaagaagaa gaagaagaag aagaagaaga agaagaagaa      4320
```

```
gaagaagaag aagaagaaga agaagaagaa gaagaagaag aagaagaaga agaagaagaa    4380
gaagaagaag aagaagaaga agaagaagaa gaagaagaag aagaagaaga agaagaagaa    4440
gaagaagaag aagaagaaga agaagaagaa gaagaagaag aagaagaaga agaagaagaa    4500
gaagaagaag aagaagaaga agaagaagaa gaagaagaag aagaagaaga agaagaagaa    4560
gaagaagaag aagaagaaga agaagaagaa gaagaagaag aagaagaaga agaagaagaa    4620
gaagaagaag aagaagaaga agaagaagaa gaagaagaag aagaagaaga agaagaagaa    4680
gaagaagaag aagaagaaga agaagaagaa gaagaagaag aagaagaaga agaagaagaa    4740
gaagaagaag aagaagaaga agaagaagaa gaagaagaag aagaagaaga agaagaagaa    4800
gaagaagaag aagaagaaga agaagaagaa gaagaagaag aagaagaaga agaagaagaa    4860
gaagaagaag aagaagaaga agaagaagaa gaagaagaag aagaagaaga agaagaagaa    4920
gaagaagaag aagaagaaga agaagaagaa gaagaagaag aagaagaaga agaagaagaa    4980
gaagaagaag aagaagaaga agaagaagaa gaagaagaag aagaagaaga agaagaagaa    5040
gaagaagaag aagaagaaga agaagaagaa gaagaagaag aagaagaaga agaagaagaa    5100

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gaagaagaag aagaagaaga agaagaagaa gaagaagaag aagaagaaga agaagaagaa      60
gaagaagaag aagaagaaga agaagaagaa gaagaagaag aagaagaaga agaagaagaa     120
gaagaagaag aagaagaaga agaagaagaa gaagaagaag aagaagaaga agaagaagaa     180
gaagaagaag aagaagaaga agaagaagaa gaagaagaag aagaagaaga agaagaagaa     240
gaagaagaag aagaagaaga agaagaagaa gaagaagaag aagaagaaga agaagaagaa     300
gaagaagaag aagaagaaga agaagaagaa gaagaagaag aagaagaaga agaagaagaa     360
gaagaagaag aagaagaaga agaagaagaa gaagaagaag aagaagaaga agaagaagaa     420
gaagaagaag aagaagaaga agaagaagaa gaagaagaag aagaagaaga agaagaagaa     480
gaagaagaag aagaagaaga agaagaagaa gaagaagaag aagaagaaga agaagaagaa     540
gaagaagaag aagaagaaga agaagaagaa gaagaagaag aagaagaaga agaagaagaa     600
gaagaagaag aagaagaaga agaagaagaa gaagaagaag aagaagaaga agaagaagaa     660
gaagaagaag aagaagaaga agaagaagaa gaagaagaag aagaagaaga agaagaagaa     720
gaagaagaag aagaagaaga agaagaagaa gaagaagaag aagaagaaga agaagaagaa     780
gaagaagaag aagaagaaga agaagaagaa gaagaagaag aagaagaaga agaagaagaa     840
```

<210> SEQ ID NO 15
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(129)
<223> OTHER INFORMATION: This sequence may encompass 1-43 'gaa'
      repeating units

<400> SEQUENCE: 15
gaagaagaag aagaagaaga agaagaagaa gaagaagaag aagaagaaga agaagaagaa      60
gaagaagaag aagaagaaga agaagaagaa gaagaagaag aagaagaaga agaagaagaa     120
gaagaagaa                                                              129

<210> SEQ ID NO 16
<211> LENGTH: 5100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5100)
<223> OTHER INFORMATION: This sequence may encompass 44-1700 'gaa'
      repeating units

<400> SEQUENCE: 16
gaagaagaag aagaagaaga agaagaagaa gaagaagaag aagaagaaga agaagaagaa      60
gaagaagaag aagaagaaga agaagaagaa gaagaagaag aagaagaaga agaagaagaa     120
gaagaagaag aagaagaaga agaagaagaa gaagaagaag aagaagaaga agaagaagaa     180
gaagaagaag aagaagaaga agaagaagaa gaagaagaag aagaagaaga agaagaagaa     240
gaagaagaag aagaagaaga agaagaagaa gaagaagaag aagaagaaga agaagaagaa     300
gaagaagaag aagaagaaga agaagaagaa gaagaagaag aagaagaaga agaagaagaa     360
gaagaagaag aagaagaaga agaagaagaa gaagaagaag aagaagaaga agaagaagaa     420
gaagaagaag aagaagaaga agaagaagaa gaagaagaag aagaagaaga agaagaagaa     480
gaagaagaag aagaagaaga agaagaagaa gaagaagaag aagaagaaga agaagaagaa     540
gaagaagaag aagaagaaga agaagaagaa gaagaagaag aagaagaaga agaagaagaa     600
gaagaagaag aagaagaaga agaagaagaa gaagaagaag aagaagaaga agaagaagaa     660
gaagaagaag aagaagaaga agaagaagaa gaagaagaag aagaagaaga agaagaagaa     720
gaagaagaag aagaagaaga agaagaagaa gaagaagaag aagaagaaga agaagaagaa     780
gaagaagaag aagaagaaga agaagaagaa gaagaagaag aagaagaaga agaagaagaa     840
gaagaagaag aagaagaaga agaagaagaa gaagaagaag aagaagaaga agaagaagaa     900
gaagaagaag aagaagaaga agaagaagaa gaagaagaag aagaagaaga agaagaagaa     960
gaagaagaag aagaagaaga agaagaagaa gaagaagaag aagaagaaga agaagaagaa    1020
gaagaagaag aagaagaaga agaagaagaa gaagaagaag aagaagaaga agaagaagaa    1080
gaagaagaag aagaagaaga agaagaagaa gaagaagaag aagaagaaga agaagaagaa    1140
gaagaagaag aagaagaaga agaagaagaa gaagaagaag aagaagaaga agaagaagaa    1200

-continued

```
gaagaagaag aagaagaaga agaagaagaa gaagaagaag aagaagaaga agaagaagaa      1260
gaagaagaag aagaagaaga agaagaagaa gaagaagaag aagaagaaga agaagaagaa      1320
gaagaagaag aagaagaaga agaagaagaa gaagaagaag aagaagaaga agaagaagaa      1380
gaagaagaag aagaagaaga agaagaagaa gaagaagaag aagaagaaga agaagaagaa      1440
gaagaagaag aagaagaaga agaagaagaa gaagaagaag aagaagaaga agaagaagaa      1500
gaagaagaag aagaagaaga agaagaagaa gaagaagaag aagaagaaga agaagaagaa      1560
gaagaagaag aagaagaaga agaagaagaa gaagaagaag aagaagaaga agaagaagaa      1620
gaagaagaag aagaagaaga agaagaagaa gaagaagaag aagaagaaga agaagaagaa      1680
gaagaagaag aagaagaaga agaagaagaa gaagaagaag aagaagaaga agaagaagaa      1740
gaagaagaag aagaagaaga agaagaagaa gaagaagaag aagaagaaga agaagaagaa      1800
gaagaagaag aagaagaaga agaagaagaa gaagaagaag aagaagaaga agaagaagaa      1860
gaagaagaag aagaagaaga agaagaagaa gaagaagaag aagaagaaga agaagaagaa      1920
gaagaagaag aagaagaaga agaagaagaa gaagaagaag aagaagaaga agaagaagaa      1980
gaagaagaag aagaagaaga agaagaagaa gaagaagaag aagaagaaga agaagaagaa      2040
gaagaagaag aagaagaaga agaagaagaa gaagaagaag aagaagaaga agaagaagaa      2100
gaagaagaag aagaagaaga agaagaagaa gaagaagaag aagaagaaga agaagaagaa      2160
gaagaagaag aagaagaaga agaagaagaa gaagaagaag aagaagaaga agaagaagaa      2220
gaagaagaag aagaagaaga agaagaagaa gaagaagaag aagaagaaga agaagaagaa      2280
gaagaagaag aagaagaaga agaagaagaa gaagaagaag aagaagaaga agaagaagaa      2340
gaagaagaag aagaagaaga agaagaagaa gaagaagaag aagaagaaga agaagaagaa      2400
gaagaagaag aagaagaaga agaagaagaa gaagaagaag aagaagaaga agaagaagaa      2460
gaagaagaag aagaagaaga agaagaagaa gaagaagaag aagaagaaga agaagaagaa      2520
gaagaagaag aagaagaaga agaagaagaa gaagaagaag aagaagaaga agaagaagaa      2580
gaagaagaag aagaagaaga agaagaagaa gaagaagaag aagaagaaga agaagaagaa      2640
gaagaagaag aagaagaaga agaagaagaa gaagaagaag aagaagaaga agaagaagaa      2700
gaagaagaag aagaagaaga agaagaagaa gaagaagaag aagaagaaga agaagaagaa      2760
gaagaagaag aagaagaaga agaagaagaa gaagaagaag aagaagaaga agaagaagaa      2820
gaagaagaag aagaagaaga agaagaagaa gaagaagaag aagaagaaga agaagaagaa      2880
gaagaagaag aagaagaaga agaagaagaa gaagaagaag aagaagaaga agaagaagaa      2940
gaagaagaag aagaagaaga agaagaagaa gaagaagaag aagaagaaga agaagaagaa      3000
gaagaagaag aagaagaaga agaagaagaa gaagaagaag aagaagaaga agaagaagaa      3060
gaagaagaag aagaagaaga agaagaagaa gaagaagaag aagaagaaga agaagaagaa      3120
gaagaagaag aagaagaaga agaagaagaa gaagaagaag aagaagaaga agaagaagaa      3180
gaagaagaag aagaagaaga agaagaagaa gaagaagaag aagaagaaga agaagaagaa      3240
gaagaagaag aagaagaaga agaagaagaa gaagaagaag aagaagaaga agaagaagaa      3300
gaagaagaag aagaagaaga agaagaagaa gaagaagaag aagaagaaga agaagaagaa      3360
gaagaagaag aagaagaaga agaagaagaa gaagaagaag aagaagaaga agaagaagaa      3420
gaagaagaag aagaagaaga agaagaagaa gaagaagaag aagaagaaga agaagaagaa      3480
gaagaagaag aagaagaaga agaagaagaa gaagaagaag aagaagaaga agaagaagaa      3540
gaagaagaag aagaagaaga agaagaagaa gaagaagaag aagaagaaga agaagaagaa      3600
```

```
gaagaagaag aagaagaaga agaagaagaa gaagaagaag aagaagaaga agaagaagaa    3660
gaagaagaag aagaagaaga agaagaagaa gaagaagaag aagaagaaga agaagaagaa    3720
gaagaagaag aagaagaaga agaagaagaa gaagaagaag aagaagaaga agaagaagaa    3780
gaagaagaag aagaagaaga agaagaagaa gaagaagaag aagaagaaga agaagaagaa    3840
gaagaagaag aagaagaaga agaagaagaa gaagaagaag aagaagaaga agaagaagaa    3900
gaagaagaag aagaagaaga agaagaagaa gaagaagaag aagaagaaga agaagaagaa    3960
gaagaagaag aagaagaaga agaagaagaa gaagaagaag aagaagaaga agaagaagaa    4020
gaagaagaag aagaagaaga agaagaagaa gaagaagaag aagaagaaga agaagaagaa    4080
gaagaagaag aagaagaaga agaagaagaa gaagaagaag aagaagaaga agaagaagaa    4140
gaagaagaag aagaagaaga agaagaagaa gaagaagaag aagaagaaga agaagaagaa    4200
gaagaagaag aagaagaaga agaagaagaa gaagaagaag aagaagaaga agaagaagaa    4260
gaagaagaag aagaagaaga agaagaagaa gaagaagaag aagaagaaga agaagaagaa    4320
gaagaagaag aagaagaaga agaagaagaa gaagaagaag aagaagaaga agaagaagaa    4380
gaagaagaag aagaagaaga agaagaagaa gaagaagaag aagaagaaga agaagaagaa    4440
gaagaagaag aagaagaaga agaagaagaa gaagaagaag aagaagaaga agaagaagaa    4500
gaagaagaag aagaagaaga agaagaagaa gaagaagaag aagaagaaga agaagaagaa    4560
gaagaagaag aagaagaaga agaagaagaa gaagaagaag aagaagaaga agaagaagaa    4620
gaagaagaag aagaagaaga agaagaagaa gaagaagaag aagaagaaga agaagaagaa    4680
gaagaagaag aagaagaaga agaagaagaa gaagaagaag aagaagaaga agaagaagaa    4740
gaagaagaag aagaagaaga agaagaagaa gaagaagaag aagaagaaga agaagaagaa    4800
gaagaagaag aagaagaaga agaagaagaa gaagaagaag aagaagaaga agaagaagaa    4860
gaagaagaag aagaagaaga agaagaagaa gaagaagaag aagaagaaga agaagaagaa    4920
gaagaagaag aagaagaaga agaagaagaa gaagaagaag aagaagaaga agaagaagaa    4980
gaagaagaag aagaagaaga agaagaagaa gaagaagaag aagaagaaga agaagaagaa    5040
gaagaagaag aagaagaaga agaagaagaa gaagaagaag aagaagaaga agaagaagaa    5100
```

METHODS OF TREATING MITOCHONDRIAL DISORDERS

CROSS REFERENCE TO RELATED APPLICATION(S)

This application is a divisional of U.S. Ser. No. 16/082,487, filed Sep. 5, 2018, which is a U.S. national phase application under 35 U.S.C. § 371 of International Application No. PCT/US2017/022447, filed Mar. 15, 2017, which claims the benefit of priority under 35 U.S.C. § 119(e) of U.S. Ser. No. 62/312,105, filed Mar. 23, 2016, the entire content of each of which is incorporated herein by reference.

GRANT INFORMATION

This invention was made with government support under NS090066 and NS108965 awarded by the National Institutes of Health. The United States government has certain rights in the invention.

SEQUENCE LISTING

The instant application contains a Sequence Listing which has been submitted electronically in ASCII format and is hereby incorporated by reference in its entirety. Said ASCII copy, created on Sep. 23, 2021, is named 114198-3029_SL.txt and is 23,521 bytes in size.

BACKGROUND OF THE INVENTION

Field of the Invention

The invention relates generally to mitochondrial disease and more specifically to methods of treating mitochondrial diseases with hematopoietic stem and progenitor cell (HSPC) gene therapy.

Background Information

Mitochondrial disease is a group of disorders caused by dysfunctional mitochondria, the organelles that are the powerhouse of the cell. Mitochondria are found in every cell of the human body except red blood cells, and convert the energy of food molecules into the ATP that powers most cell functions. Mitochondrial diseases are sometimes caused by mutations in the mitochondrial DNA that affect mitochondrial function. Other causes of mitochondrial disease are mutations in genes of the nuclear DNA, whose gene products are imported into the mitochondria (mitochondrial proteins) as well as acquired mitochondrial conditions. Mitochondrial diseases take on unique characteristics both because of the way the diseases are often inherited and because mitochondria are so critical to cell function. The subclass of these diseases that have neuromuscular disease symptoms are often called mitochondrial myopathies. Symptoms associated with mitochondrial disease typically include poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction and dementia.

Mitochondrial diseases/disorders may be caused by mutations, acquired or inherited, in mitochondrial DNA (mtDNA) or in nuclear genes that code for mitochondrial components. They may also be the result of acquired mitochondrial dysfunction due to adverse effects of drugs, infections, or other environmental causes.

One of the most common inherited autosomal recessive diseases associated with reduced expression of the nuclear-encoded mitochondrial protein, frataxin, is Friedreich's ataxia (FRDA) which affects people at an early age. Point mutations have also been described resulting in truncated or dysfunctional frataxin. FRDA is characterized by ataxia, areflexia, sensory loss, muscle weakness, and cardiomyopathy. Symptoms typically begin between 5 to 15 years of age and patients will be in a wheelchair within 10-15 years of onset.

FRDA is caused, in 98% of all cases, by a genetic mutation resulting in expansion of GAA repeats in the first intron of the frataxin gene (FXN). In healthy individuals the alleles may contain up to about 40 GAA repeats, whereas expanded alleles in FRDA patients can consist of 90 to 1700 repeats (SEQ ID NO: 12) (see FIG. 1). The GAA repeat expansion leads to reduced expression of frataxin, a highly conserved mitochondrial protein mainly expressed in mitochondria-rich tissues including the nervous system, muscle, and heart. Also, carriers (heterozygous for the expanded allele) show ~50% reduction of frataxin mRNA and protein levels compared to normal expression, although they do not show any symptoms. While its function is not fully elucidated, frataxin is an iron binding protein participating in Fe—S cluster assembly and in its absence, iron accumulates within mitochondria leading to defective iron-mediated biosynthetic processes and increased oxidative stress.

Expanded GAA repeats form an intramolecular triple-helix (triplex), so-called H-DNA, in supercoiled plasmids isolated from *E. coli*. Several models representing the triplex structures formed at expanded GAA repeats are proposed, and direct evidence for a pyrimidine motif H-DNA structure at pathological GAA expansions in vitro has recently been provided. Also, formation of a higher order structure named "sticky DNA" has been observed in frataxin GAA repeats-containing plasmids using gel electrophoresis and atomic force microscopy. The molecular structure of sticky DNA is not resolved; however, current evidence demonstrates that sticky DNA forms as one long intramolecular triplex structure or by the association of two triplexes.

The observed effects on DNA replication and transcription are dependent on the length and orientation of the GAA repeats in plasmids, which correlate with formation of the specific DNA structure (H-DNA). Finally, the GAA repeats are associated with a pattern of DNA methylation and histone acetylation in the adjacent regions and the formation of silenced chromatin. The presence of H-DNA and higher order structures within the GAA repeats is believed to recruit chromatin-remodeling protein complexes that maintain a close chromatin structure leading to down-regulation of frataxin gene transcription.

Numerous data have demonstrated that analysis of GAA repeats constitute an essential part in the diagnosis of FRDA along with clinical diagnosis. Molecular genetic tests are also performed to identify carriers and in prenatal testing. Current FA diagnostic methods involve polymerase chain reaction (PCR) analysis and Southern blotting technique. The PCR test is performed by amplification of the GAA repeat-containing DNA region in the frataxin gene. The different PCR reactions that have been employed to map GAA repeat expansions are classical PCR, long-range PCR or triplet-primed PCR (TP-PCR). In all cases, the size of the PCR fragment is analyzed using agarose-gel electrophoresis and DNA sequencing. In most cases, both PCR and Southern blot are combined to complement the results. Problems encountered during amplification of medium- and long-sized GAA repeats (i.e., number of repeats >200) using PCR have been reported. The repetitive nature of the expanded sequence and its ability to adopt H-DNA and higher order DNA structures are the two main factors causing polymerase pausing leading to false results.

To date, there are no known cures or preventative measures for such mitochondrial diseases, with current therapies being directed to treating the associated symptoms. Thus, there is a need in the art for alternative or improved methods for treating mitochondrial diseases/disorders.

SUMMARY OF THE INVENTION

Accordingly, in one aspect, the invention provides a method of treating a mitochondrial disease or disorder in a subject. The method includes introducing ex vivo a functional human frataxin (hFXN) into hematopoietic stem and progenitor cells (HSPCs) of the subject, and transplanting the HSPCs into the subject, thereby treating the mitochondrial disease or disorder. The step of introducing may include contacting a vector comprising a polynucleotide encoding hFXN and a FXN promoter (or other regulatory sequence that is operable with the polynucleotide and in the cell) with the HSPCs and allowing expression of hFXN. In various embodiments, the mitochondrial disease or disorder is selected from the group consisting of Friedreich's ataxia (FRDA), diabetes, Leigh syndrome, Leber's hereditary optic neuropathy, myoneurogenic gastrointestinal encephalopathy, and cancer. The subject may be a mammal, such as a human. In various embodiments, the vector is a self-inactivating (SIN)-lentivirus vector, such as pCCL-FRDAp-FXN. In various embodiments, expression of hFXN corrects neurologic, cardiac and muscular complications within about 6-12 months post-transplantation. In another aspect, the hFXN polynucleotide is introduced into HSPCs in vivo in a subject.

In another aspect, the present invention provides a method of treating a mitochondrial disease or disorder in a subject comprising contacting cells expressing hFXN from the subject with a vector encoding a gene editing system that when transfected into the cells removes a trinucleotide extension mutation of endogenous hFXN, thereby treating the mitochondrial disease or disorder. In various embodiments, the gene editing system is selected from the group consisting of CRISPR/Cas, zinc finger nucleases, and transcription activator-life effector nucleases. The step of contacting may include obtaining a sample of cells from the subject, transfecting or transducing the gene editing system into the sample of cells to create gene-corrected cells, and thereafter, transplanting the gene-corrected cells into the subject. The sample of cells may be any cells expressing hFXN, such as blood cells and HSPCs from the subject.

In another aspect, the present invention provides an expression cassette comprising a promoter or regulatory sequence functionally linked to a polynucleotide encoding hFXN. Also provided are a vector, such as a self-inactivating (SIN)-lentivirus vector, that includes a regulatory sequence such as a promoter functionally linked to a polynucleotide encoding hFXN.

BRIEF DESCRIPTION OF THE DRAWINGS

FIG. 1A shows the results of WT (n=16), YG8R control (n=4), YG8R/YG8R HSPCs (n=5) and YG8R/WT HSPCs (n=13) mice at both 5 and 9 months of age. Locomotor activity was tested using an open field, coordination using a rotarod, gait using an automated gait analysis system and muscle strength using forelimb grip strength. Data are expressed as means±sem; *P<0.05, P<0.005, *P<0.0005; NS statistically non-significant. For statistical comparison of three experimental groups, a mixed analysis of variance (ANOVA) with age of testing as a within-subjects variable was used followed by independent sample t-test. FIG. 1B is a representation showing intron 1 of an unaffected (top) frataxin gene (FXAN) and intron 1 of FRDA (bottom) FXN, and discloses SEQ ID NOs: 15-16, respectively, in order of appearance. FIG. 1C shows Nissl-stained sections of lumbar DRG (L5) from representative 9-month-old WT (n=15), YG8R control (n=4), YG8R/YG8R HSPCs (n=4) and YG8R/WT HSPCs (n=11) mice. DRGs of YG8R controls exhibit large vacuoles (arrows). Scale bars, 100 µm. Graph on the right depicts total vacuole area per DRG area; data are expressed as means±sem; P<0.005; *P<0.0005. NS, statistically non-significant. FIG. 1D shows representative confocal images from a WT GFP+ HSPC-transplanted YG8R mouse 7 months post-transplantation stained with anti-GFP and anti-NeuN. Left: Image of a lumbar (L5) DRG illustrates engraftment of GFP+ HSPC-derived cells throughout DRG. Scale bar, 100 µm. Magnified image (below) demonstrates frequent close association of HSPC-derived cells with DRG neurons. Scale bar, 20 µm. Right: Images of cervical, thoracic and lumbar spinal cord show abundant HSPC engraftment throughout spinal cord gray and white matter at all levels. Scale bars, 250 µm.

FIG. 2A shows representative transverse sections of the brain of a WT GFP+ HSPC-transplanted YG8R mouse 7 months post-transplantation labeled with anti-GFP and anti-NeuN. Scale bar, 1 mm. Magnified picture #1 of the brain shows that GFP+ HSPC-derived cells are observed in periventricular regions including the corpus callosum (cc), lateral septal nuclei (LS), caudate putamen (CP), anterior cingulate area (ACA), and the somatosensory cortex (M1, S2). VL, lateral ventricle. Scale bar, 150 µm. Magnified picture #2 of ventral striatum of the brain shows that the engrafted GFP+ HSPCs are present in regions of the ventral striatum including the anterior commissure (aco), nucleus accumbens (ACB), and lateral septal nuclei (LS). CP, caudate putamen. Scale bar, 150 µm. Magnified picture #3 shows that GFP+ HSPC-derived cells are observed in the ventral pallidum (PAL) and the ventral striatum, including the islands of Calleja (isl) and the olfactory tubercle (OT). Scale bar, 150 µm. GFP+ HSPCs were also detected through gray and white matter of the brainstem and cerebellum. Scale bar, 500 µm. Insets depict engraftment within the dentate nucleus (DN) of the cerebellum and the spinal trigeminal nucleus (Sp) of the brainstem. Scale bar, 50 µm. FIG. 2B shows confocal image of brain labeled with anti-GFP, anti-Iba1 and anti-NeuN. Most of the bone marrow-derived GFP+ cells co-localize with the microglial marker Iba1. Scale bar, 30 µm. FIG. 2C shows quantification of murine frataxin mRNA expression in cerebellum from WT (n=14), YG8R (n=8) and YG8R/HSPCs (n=13) mice. Data are represented as fold change relative to WT normalized to GAPDH. Data are expressed as means±sem; P<0.005, *P<0.0005. FIG. 2D shows the results of a representative Western blot showing the level of oxidation in cerebrum of one WT, one YG8R, one YG8R/YG8R HSPCs and one YG8R/WT HSPCs mouse with (+) or without (−) derivatization reagent. Oxyblot analysis detected significantly higher level of oxidized proteins in cerebrum of 9-month-old YG8R (n=4) and YG8R/YG8R HSPCs (n=4) compared to WT (n=6) and YG8R/HSPCs (n=6) mice. Data are expressed as means±sem; *P<0.05, NS statistically non-significant. FIG. 2E shows scatter plots of mitochondrial gene changes in cerebrum from WT animals (n=3) compared to YG8R (n=3) (left scatter plot) or YG8R/WT HSPCs mice (n=3) (right scatter plot). The center line represents the cipher, and upregulated and downregulated genes are noted by dots, respectively. mRNA changes that are significantly different between groups are represented on a separate bar graph. Data are expressed as means±sem; *P<0.05, P<0.005, *P<0.0005, NS statistically non significant as compared to WT.

FIGS. 3A-3H are pictorial and graphical diagrams showing transplanted HSPCs engraft abundantly in heart and muscle. FIG. 3A shows the results of a representative Western blot showing level of oxidation in skeletal muscle of one WT, one YG8R and one YG8R/HSPCs mouse with (+) or without (−) derivatization reagent. Oxyblot analysis detects high level of protein oxidation only in skeletal muscle of 9-month-old YG8R controls (YG8R, n=4 and YG8R/YG8R HSPCs, n=5) compared to WT (n=16) and YG8R/HSPCs (n=13) mice. Error bars indicate SEM. *p<0.05, NS statistically non-significant. FIG. 3B shows quantification of lactate and pyruvate by mass-spectrometry in muscle tissues from WT (n=6), YG8R (n=3) and YG8R/WT HSPCs (n=5) mice. The lactate/pyruvate ratio is significantly increased in the YG8R mice compared to WT while comparable in YG8R/WT HSPCs animals. Error bars indicate sem; *P<0.05, ***P<0.0005, NS statistically non-significant. FIG. 3C shows representative Perl's staining of heart sections from 18 month old WT, YG8R control and YG8R/WT HSPCs. Characteristic staining indicates iron deposition. Scale bars, 50 μm and 15 μm (zoom). The associated bar graph shows iron quantification in heart sections from WT (n=4), YG8R controls (YG8R (n=2), YG8R/YG8R HSPCs (n=2)), and YG8R/WT HSPCs (n=3). Error bars indicate sem; *P<0.05, NS statistically non-significant. FIGS. 3D-3E show quantification of murine frataxin mRNA expression in heart (FIG. 3D) and skeletal muscle (FIG. 3E) from WT (n=12), YG8R (n=7) and YG8R/HSPCs (n=11) mice. Data are represented as fold change relative to WT normalized to GAPDH, error bars indicate sem; *P<0.05, P<0.005, *P<0.0005, NS statistically non-significant. FIG. 3F shows an image of a heart section from WT HSPCs transplanted YG8R mouse 7 months post-transplantation stained with anti-GFP, the cardiomyocyte marker anti-α-actinin and DAPI. GFP+ cells are found in all the cardiac tissue with a highest expression in the valve suggesting that HSPCs derived cells are entering the heart by the blood flow. Scale bar, 150 μm. Magnified pictures of the heart show high level of engraftment in the left ventricle (bottom) and in the base of the aorta (top). Scale bars, 50 μm. FIG. 3G shows skeletal muscle section from WT HSPCs transplanted YG8R mouse 7 months post-transplantation stained with anti-GFP, filamentous actin dye Phalloidin and DAPI. GFP+ cells are engrafted homogenously in the tissue. Scale bar, 150 μm. Magnified picture of the skeletal muscle (on the left) shows that GFP+ cells are localized interstitially between muscle fibers. Scale bar, 50 μm. FIG. 3H shows quantification of murine MuRF-1, Atrogin-1 and myostatin mRNA expression in skeletal muscle from WT (n=5), YG8R (n=5) and YG8R/HSPCs (n=5) mice. Data are represented as fold change relative to WT normalized to GAPDH, error bars indicate sem; *P<0.05, NS statistically non-significant.

FIGS. 4A and 4B show representative frames from confocal imaging movies of YG8R-derived fibroblasts (F) co-cultured with primary macrophages (M) isolated from a DsRed Cox8-GFP transgenic mouse (FIG. 4A) or with IC21 macrophages transduced with a LV-hFXN-GFP and stained with a red MitoTracker (FIG. 4B). Scale bar, 10 μm. FIG. 4C shows a representative confocal image of brain sections from an YG8R mouse transplanted with DsRed+ HSPCs (control) and brain and spinal cord sections from an YG8R mouse transplanted with DsRed+/Cox8-GFP+ HSPCs at 7 months post-transplantation labelled with an anti-NeuN antibody. In addition to the DsRed-derived bone marrow cells, cox8-GFP are observed in host neurons in brain and spinal cord (arrows). For DRG, heart and muscle, see FIGS. 7A and 7B. Scale bars, 10 μm. FIG. 4D shows representative confocal images of spinal cord section from an YG8R mouse transplanted with DsRed+/Cox8-GFP+ HSPCs at 7 months post-transplantation labelled with an anti-NeuN antibody showing cox8-GFP within the branch extension of the DsRed+ microglial cell (arrows). Scale bar, 5 μm. FIG. 4E shows quantification of neurons containing cox8-GFP in the cervical spinal cord gray matter of YG8R mice transplanted with DsRed+/Cox8-GFP+ HSPCs at 7 months post-transplantation (for description of the automatic unbiased quantification method see FIG. 8). FIG. 4F shows representative confocal images of brain and spinal cord sections from an YG8R mouse transplanted with DsRed+ HSPCs transduced with LV-hFXN-GFP at 7 months post-transplantation and stained with anti-mcherry and anti-NeuN antibodies. In addition to the DsRed-derived bone marrow cells, frataxin-GFP are observed in host neurons. Scale bar, 10 μm.

FIGS. 6A and 6B show confocal images of DRG, spinal cord and brain sections from WT GFP+ HSPC-transplanted YG8R mice labeled with anti-GFP, anti-CD68 (FIG. 6A), anti-MHCII (FIG. 6B), anti-NeuN (FIG. 6A), and DAPI. Scale bars, 30 μm. FIGS. 6C and 6D show transverse spinal cord (FIG. 6C) and brain (FIG. 6D) section from WT GFP+ HSPC-transplanted YG8R mouse labeled with anti-MHCII. Scale bars, 100 μm (FIG. 6C) and 300 μm (FIG. 6D). FIG. 6E shows a confocal image of brain section from WT GFP+ HSPC-transplanted YG8R mouse labeled with anti-vwf Scale bar, 50 μm. FIG. 6F shows a confocal image of choroid plexus from WT DsRed+ HSPC-transplanted YG8R mouse labeled with anti-RFP and anti-Iba1. Scale bar, 100 μm.

FIG. 9A shows a representative transverse image of cervical spinal cord gray matter from a YG8R mouse at 7 months following transplantation with Cox8-GFP DsRed HSPCs, stained with anti-NeuN. Scale bar, 500 μm. FIG. 9B shows automatic outline and quantification of neurons by ImagePro software. FIG. 9C shows that GFP signal is only counted within the delineated neurons (arrow) and not outside (star). FIG. 9D shows the percentage of neurons within the gray matter of the spinal cord that contain GFP for three different animals (transplanted) and for one control. The entire gray matter from three experimental animals and one control (three sections per animal) were quantified.

DETAILED DESCRIPTION OF THE INVENTION

Figure 1A:
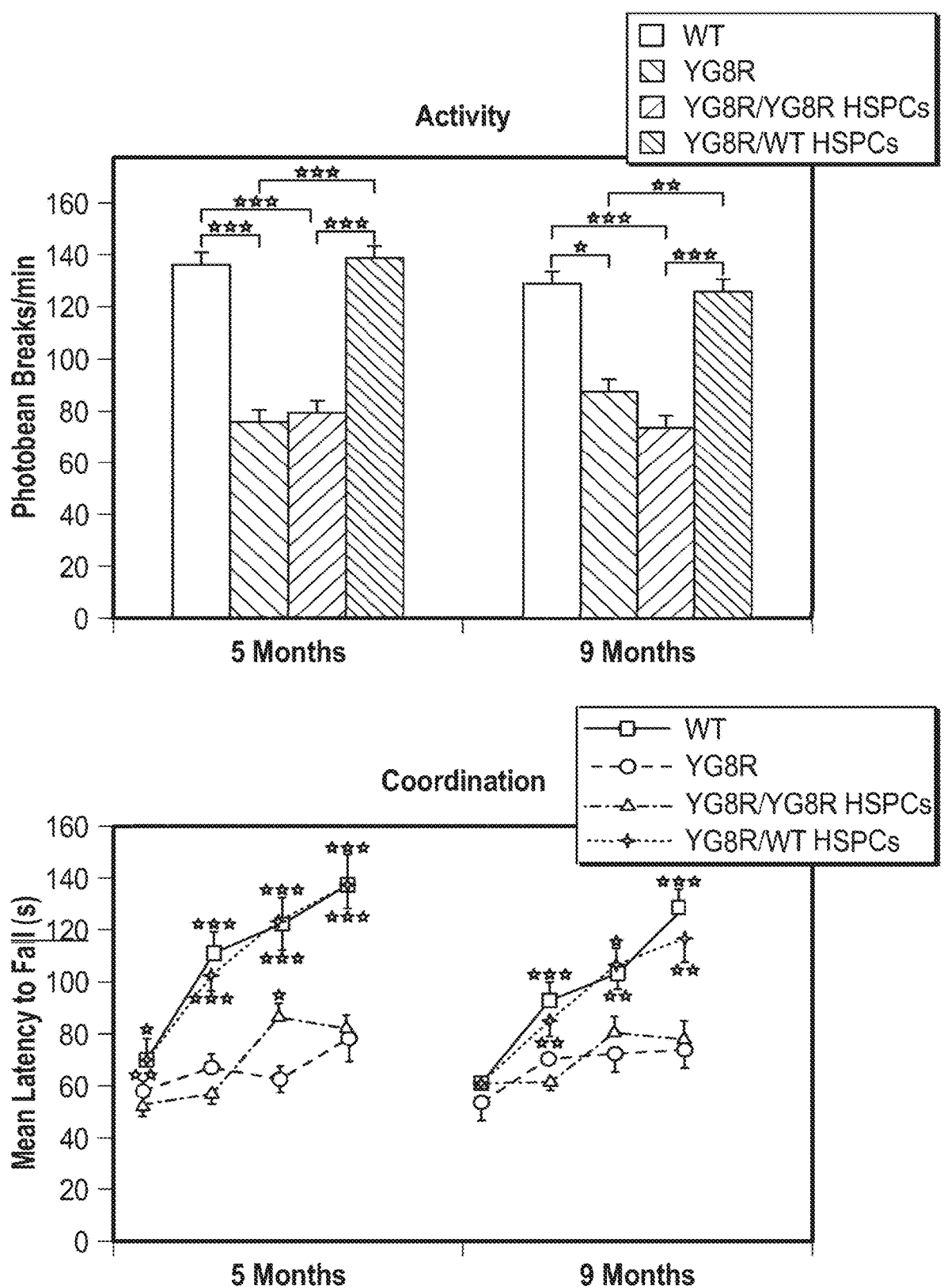
FIGS. 1A-1D are graphical and pictorial diagrams showing that systemic transplantation of WT HSPCs prevents sensory neuron degeneration and neurobehavioral deficits in YG8R mice.
Figure 1A:
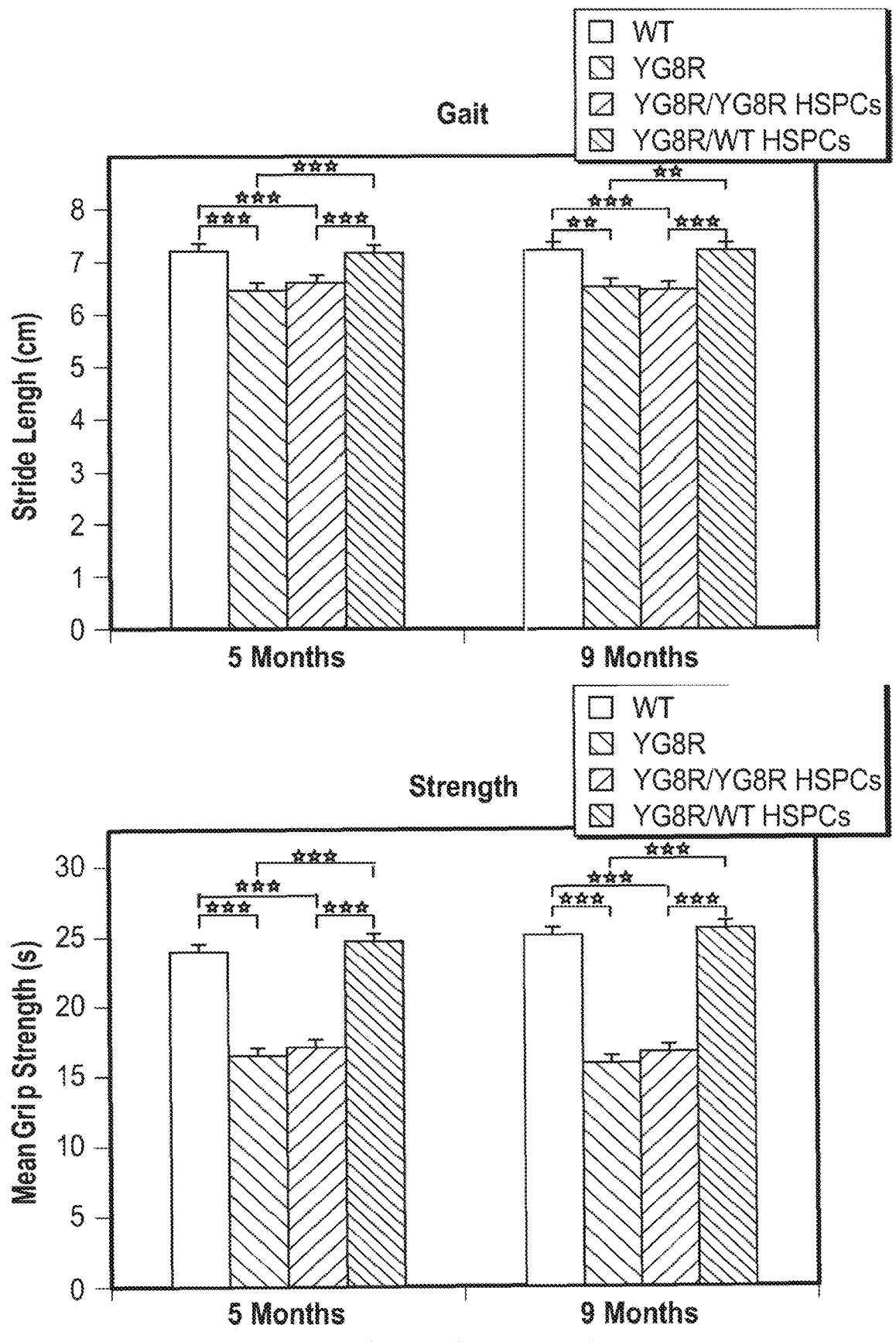
Figure 1B:
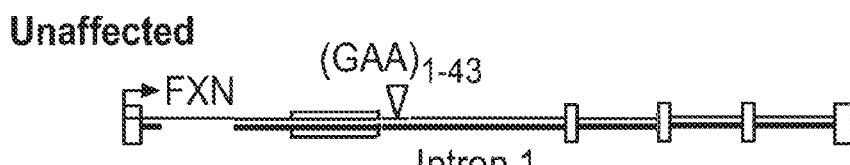
Figure 1B:
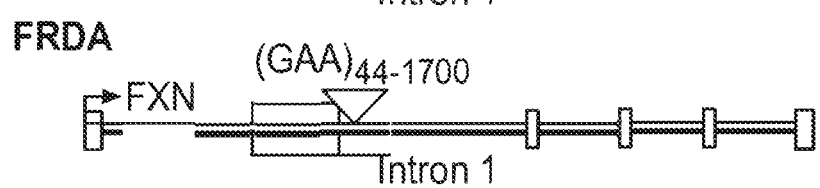

The present invention is based on the finding of complete phenotypic correction of mitochondrial disorders occurs after a single transplantation of wildtype hematopoietic stem and progenitor cells, which differentiated into phagocytic cells in the nervous system, muscle and heart leading to the neuronal and myocyte cross-correction. There is a pressing need to identify effective therapies for mitochondrial disorders such as FRDA for which there remains no treatment. To date, preclinical studies using stem cells or gene therapy have had limited success, or have been restricted to assessment of specific tissues.

The present disclosure demonstrates that a self-inactivating (SIN)-lentivirus vector containing the human frataxin (hFXN) cDNA as well as the optimal promoter can be used to ex vivo gene-corrected patients' autologous hematopoietic stem and progenitor cells (HSPCs), which can then be re-transplant in the patients to repopulate their bone marrow, which will be a reservoir of "healthy" cells for the rest of the life of the patients. These cells mobilize and integrate into the diseased tissues (brain, muscle, heart), and will lead to their rescue. While autologous HSPCs are used in the illustrative examples herein, one of skill in the art would recognize that other HSPCs would be useful as well (e.g., allogeneic).

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" or "host organism," as used herein, refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician. Thus, the term "therapeutically effective amount" is used herein to denote any amount of a formulation that causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "therapeutic effect," as used herein, encompasses a therapeutic benefit and/or a prophylactic benefit as described herein.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually orally or by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and infrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. In addition, there are a variety of biomaterial-based technologies such as nano-cages and pharmacological delivery wafers (such as used in brain cancer chemotherapeutics) which may also be modified to accommodate this technology.

The viral vectors most commonly assessed for gene transfer are based on DNA-based adenoviruses (Ads) and adeno-associated viruses (AAVs) and RNA-based retroviruses and lentiviruses. Lentivirus vectors have been most commonly used to achieve chromosomal integration.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods.

As used herein, "treatment" or "treating" means to administer a composition to a subject or a system with an undesired condition. The condition can include a disease or disorder. "Prevention" or "preventing" means to administer a composition to a subject or a system at risk for the condition. The condition can include a predisposition to a disease or disorder. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur.

As used herein, the term "genetic modification" is used to refer to any manipulation of an organism's genetic material in a way that does not occur under natural conditions. Methods of performing such manipulations are known to those of ordinary skill in the art and include, but are not limited to, techniques that make use of vectors for transforming cells with a nucleic acid sequence of interest. Included in the definition are various forms of gene editing in which DNA is inserted, deleted or replaced in the genome of a living organism using engineered nucleases, or "molecular scissors." These nucleases create site-specific double-strand breaks (DSBs) at desired locations in the genome. The induced double-strand breaks are repaired through nonhomologous end-joining (NHEJ) or homologous recombination (HR), resulting in targeted mutations (i.e., edits).

There are several families of engineered nucleases used in gene editing, for example, but not limited to, meganucleases, zinc finger nucleases (ZFNs), transcription activator-like effector-based nucleases (TALEN), and the CRISPR-Cas system.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with elements including a Cas gene and specifically designed CRISPRs, nucleic acid sequences can be cut and modified at any desired location. Methods of preparing compositions for use in genome editing using the CRISPR/Cas systems are described in detail in US Pub. No. 2016/0340661, US Pub. No. 20160340662, US Pub. No. 2016/0354487, US Pub. No. 2016/0355796, US Pub. No. 20160355797, and WO 2014/018423, which are specifically incorporated by reference herein in their entireties.

Thus, as used herein, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer", "guide RNA" or "gRNA" in the context of an endogenous CRISPR system), or other sequences and transcripts from a CRISPR locus. One or more tracr mate sequences operably linked to a guide sequence (e.g., direct repeat-spacer-direct repeat) can also be referred to as "pre-crRNA" (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, Science, 15:339(6121):819-823 (2013) and Jinek, et al., Science, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.upsud.fr, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms. The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J Biol. Chem.* 269:31,978-31,982 (1994b), all of which are incorporated herein by reference. One or more of these enzymes (or enzymatically functional fragments thereof) can be used as a source of cleavage domains.

Transcription activator-like effector nucleases (TALENs) have an overall architecture similar to that of ZFNs, with the main difference being that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats. Methods of engineering TAL to bind to specific nucleic acids are described in Cermak, et al, *Nucl. Acids Res.* 1-11 (2011); US Published Application No. 2011/0145940, which discloses TAL effectors and methods of using them to modify DNA; Miller et al. *Nature Biotechnol* 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246. Each of the foregoing references are incorporated herein by reference in their entireties.

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site. Therefore, in some embodiments, the genome editing vector or composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing vector or composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6xHis (SEQ ID NO: 13), a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted" way, for example gene knock-out, gene knock-in, gene editing, gene tagging, etc., as used in, for example, gene therapy.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium.

Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, a "regulatory gene" or "regulatory sequence" is a nucleic acid sequence that encodes products (e.g., transcription factors) that control the expression of other genes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

As used herein, the term "humanized mouse" (Hu-mouse) is a mouse developed to carry functioning human genes, cells, tissues, and/or organs. Humanized mice are commonly used as small animal models in biological and medical research for human therapeutics. Immunodeficient mice are often used as recipients for human cells or tissues, because they can relatively easily accept heterologous cells due to lack of host immunity.

HSCs possess the ability of multipotency (i.e., one HSC can differentiate into all functional blood cells) and self-renewal (i.e., HSCs can divide and give rise to an identical daughter cell, without differentiation). Through a series of lineage commitment steps, HSCs give rise to progeny that progressively lose self-renewal potential and successively become more and more restricted in their differentiation capacity, generating multi-potential and lineage-committed progenitor cells, and ultimately mature functional circulating blood cells.

The ability of hematopoietic stem and progenitor cells (HSPCs) to self-renew and differentiate is fundamental for the formation and maintenance of life-long hematopoiesis and deregulation of these processes may lead to severe clinical consequences. HSPCs are also highly valuable for their ability to reconstitute the hematopoietic system when transplanted and this has enabled their use in the clinic to treat a variety of disorders including bone marrow failure, myeloproliferative disorders and other acquired or genetic disorders that affect blood cells.

As used herein, a "pluripotent cell" refers to a cell derived from an embryo produced by activation of a cell containing DNA of all female or male origin that can be maintained in vitro for prolonged, theoretically indefinite period of time in an undifferentiated state that can give rise to different differentiated tissue types, i.e., ectoderm, mesoderm, and endoderm. "Embryonic stem cells" (ES cells) are pluripotent stem cells derived from the inner cell mass of a blastocyst, an early-stage preimplantation embryo.

As used herein "pharmaceutically acceptable carrier" encompasses any of the standard pharmaceutical carriers, such as a phosphate buffered saline solution, water and emulsions such as an oil/water or water/oil emulsion, and various types of wetting agents.

This work shows that one-time hematopoietic stem and progenitor cell (HSPC) transplantation holds the potential to become a life-long curative therapy for a disease or disorder associated with mitochondrial dysfunction. Given the risks associated with allogeneic stem cell transplantation, the objective was to develop an autologous HSPC gene therapy for mitochondrial diseases.

As discussed above, mitochondrial diseases/disorders may be caused by mutations, acquired or inherited, in mitochondrial DNA (mtDNA) or in nuclear genes that code for mitochondrial components. They may also be the result of acquired mitochondrial dysfunction due to adverse effects of drugs, infections, or other environmental causes.

Examples of mitochondrial diseases include, but are not limited to, mitochondrial myopathy, diabetes mellitus and deafness (DAD), Leber's hereditary optic neuropathy (LHON), Leigh syndrome, subacute sclerosing encephalopathy, Neuropathy, ataxia, retinitis pigmentosa, and ptosis (NARP), myoneurogenic gastrointestinal encephalopathy (MNGIE), Myoclonic Epilepsy with Ragged Red Fibers (MERRF), Mitochondrial myopathy, encephalomyopathy, lactic acidosis, stroke-like symptoms (MELAS), mitochondrial neurogastrointestinal encephalomyopathy (MNGIE) and diseases due to mitochondrial complex deficiency, such as Friedreich's ataxia (FRDA).

FRDA is a progressively lethal multi-systemic disease. Although the exact function of FXN is still under debate, it is predicted to assist in the biogenesis of mitochrondrial iron-sulfur clusters. Thus, frataxin deficiency results in altered cellular iron metabolism, increased mitochondrial iron load, decreased mitochondrial energy production and biogenesis as well as increased oxidative stress. Clinical features include gait and limb ataxia, muscle weakness, dysarthria and also vision and hearing anomalies, diabetes and cardiomyopathy. Frataxin deficiency impacts neuronal functions particularly and this affects mainly the peripheral and central nervous systems (CNS), leading to the progressive destruction of the Dorsal Root Ganglia (DRG). This progressive neurodegeneration leads to loss of motor skills and progressive muscle degeneration, and ultimately inability to walk within 10 to 15 years of onset. Heart abnormalities cause premature death in 60% to 80% of the affected individuals; the average age of death is in the mid-thirties. The different clinical trials of pharmacological compounds against oxidative stress (idebone and Coenzyme Q10) or mitochondrial iron accumulation (deferipone) failed to prove efficacy. An epigenetic approach using a histone deacetylase inhibitor is currently being testing in phase I clinical trial.

Hematopoietic stem and progenitor cells (HSPCs) are ideal candidates for use in regenerative medicine and cell replacement therapies because of their ease of isolation, self-renewal capacity, and safety. As such, the present disclosure evaluates the impact of hematopoietic stem and progenitor cell (HSPC) transplantation in a mouse model of FRDA. The rationale for using HSPC to treat FRDA came from previous work on cystinosis, a multi-systemic lysosomal storage disorder. Briefly, HSPC transplantation using a self-inactivating (SIN)-lentivirus vector containing human CTNS cDNA under the control of the strong ubiquitous short intron-less human Elongation Factor 1 alpha (EFS) promoter in lethally irradiated Ctns$^{-/-}$ mice (mouse model of cystinosis) led to the abundant engraftment of HSPC-derived cells in all organs, which correlated with the dramatic reduction in tissue cystine levels (up to 94% decrease). This treatment also led to long-term preservation of the kidney structure and function, rescue of the eye defects and thyroid dysfunction. These data showed that a single HSPC transplant could prevent the multi-organ failure for the lifespan of the mice. However, these results were particularly surprising as cystinosin is a ubiquitous, lysosomal transmembrane protein. Addressing the cellular mechanism, it was demonstrated that transplanted HSPCs led to the transfer of cystinosin-bearing lysosomes via tunneling nanotubes (TNTs) after differentiating into macrophages. In vivo, macrophage-derived tubular extensions penetrated the dense tubular basement membrane and delivered cystinosin-containing lysosomes into the epithelia in Ctns$^{-/-}$ mice, so as to prevent proximal tubule degeneration. The same mechanism has been demonstrated in the eye and thyroid of HSPC-transplanted Ctns$^{-/-}$ mice.

However, in contrast to the CTNS gene, overexpression of frataxin is toxic. Thus, one strategy is to generate a new lentiviral construct in which FXN will be expressed under the control of its own promoter and test the efficacy and safety of this strategy in vitro and in vivo. Alternatively, or in addition thereto, removing the trinucleotide extension mutation using gene editing techniques is contemplated to correct the defect in FRDA HSPC.

Accordingly, in one aspect, the invention provides a method of treating a mitochondrial disease or disorder in a subject. The method includes introducing ex vivo a functional human frataxin (hFXN) into hematopoietic stem and progenitor cells (HSPCs) of the subject, and thereafter transplanting the HSPCs into the subject, thereby treating the mitochondrial disease or disorder. The step of introducing may include contacting a vector comprising a polynucleotide encoding hFXN and a ubiquitous or endogenous FXN promoter with the HSPCs and allowing expression of hFXN. In various embodiments, the vector is a self-inactivating (SIN)-lentivirus vector, such as pCCL-EFS-FXN or pCCL-FRDAp-FXN. In various embodiments, expression of hFXN corrects neurologic, cardiac and muscular complications within about 6-12 months post-transplantation.

```
Nucleic acid sequences for human and mouse
frataxin (FRDA) are known in the art. See, for
example, GenBank Accession No.: U43747.1, human
frataxin mRNA, complete cds, which provides the
nucleic acid sequence (SEQ ID NO: 1):
TTTACAGGGCATAACTCATTTTATCCTTACCACAATCCTATGAAGTAGG

AACTTTTATAAAACGCATTTTATATNCAAGGGCACAGAGAGGNTAATTA

ACTTGCCCTCTGGTCACACAGCTAGGAAGTGGGCAGAGTACAGATTTAC

ACTAGGCATCCGTCTCCTGNCCCCACATANCCAGCTGCTGTAAACCCAT

ACCGGCGGCCAAGCAGCCTCAATTTGTGCATGCACCCACTTCCCAGCAA

GACAGCAGCTCCCAAGTTCCTCCTGTTTAGAATTTTAGAAGCGGCGGGC

CACCAGGCTGCAGTCTCCCTTGGGTCAGGGGTCCTGGTTGCACTCCGTG

CTTTGCACAAAGCAGGCTCTCCATTTTTGTTAAATGCACGAATAGTGCT

AAGCTGGGAAGTTCTTCCTGAGGTCTAACCTCTAGCTGCTCCCCACAG

AAGAGTGCCTGCGGCCAGTGGCCACCAGGGGTCGCCGCAGCACCCAGCG

CTGGAGGGCGGAGCGGGCGGCAGACCCGGAGCAGCATGTGACTCTCGGG

CGCCGCGCAGTAGCCGGCCTCCTGGCGTCACCCAGCCCGGCCCAGGCCC

AGACCCTCACCCGGGTCCCGCGGCCGGCAGAGTTGGCCCCACTCTGCGG

CCGCCGTGGCCTGCGCACCGACATCGATGCGACCTGCACGCCCCGCCGC

GCAAGTTCGAACCAACGTGGCCTCAACCAGATTTGGAATGTCAAAAAGC

AGAGTGTCTATTTGATGAATTTGAGGAAATCTGGAACTTTGGGCCACCC

AGGCTCTCTAGATGAGACCACCTATGAAAGACTAGCAGAGGAAACGCTG

GACTCTTTAGCAGAGTTTTTTGAAGACCTTGCAGACAAGCCATACACGT

TTGAGGACTATGATGTCTCCTTTGGGAGTGGTGTCTTAACTGTCAAACT

GGGTGGAGATCTAGGAACCTATGTGATCAACAAGCAGACGCCAAACAAG

CAAATCGGCTATCTTCTCCATCCAGTGGACCTAAGCGTTATGACTGGA

CTGGGAAAAACTGGGTGTTCTCCCACGACGGCGTGTCCCTCCATGAGCT

GCTGGCCGCAGAGCTCACTAAAGCCTTAAAAACCAAACTGGACTTGTCT

TGGTTGGCCTATTCCGGAAAAGATGCTTGATGCCCAGCCCCGTTTTAAG

GACATTAAAAGCTATCAGGCCAAGACCCCAGCTTCATTATGCAGCTGAG

GTGTGTTTTTGTTGTTGTTGTTGTTTATTTTTTTATTCCTGCTTTTG

AGGACACTTGGGCTATGTGTCACAGCTCTGTACAAACAATGTGTTGCCT

CCTACCTTGCCCCCAAGTTCTGATTTTTAATTTCTATGGAAGATTTTTT

GGATTGTCGGATTTCCTCCCTCACATGATACCCCTTATCTTTTATAATG

TCTTATGCCTATACCTGAATATAACAACCTTTAAAAAAGCAAAATAATA

AGAAGGAAAAATTCCAGGAGGGAAAAAAAAAAAA,

GenBank Accession No.: U43747.1:526-1158, human
frataxin mRNA, complete cds, which provides the
nucleic acid sequence (SEQ ID NO: 2):
ATGTGGACTCTCGGGCGCCGCGCAGTAGCCGGCCTCCTGGCGTCACCCA

GCCCGGCCCAGGCCCAGACCCTCACCCGGGTCCCGCGGCCGGCAGAGTT

GGCCCCACTCTGCGGCCGCCGTGGCCTGCGCACCGACATCGATGCGACC

TGCACGCCCCGCCGCGCAAGTTCGAACCAACGTGGCCTCAACCAGATTT

GGAATGTCAAAAAGCAGAGTGTCTATTTGATGAATTTGAGGAAATCTGG

AACTTTGGGCCACCCAGGCTCTCTAGATGAGACCACCTATGAAAGACTA

GCAGAGGAAACGCTGGACTCTTTAGCAGAGTTTTTTGAAGACCTTGCAG

ACAAGCCATACACGTTTGAGGACTATGATGTCTCCTTTGGGAGTGGTGT

CTTAACTGTCAAACTGGGTGGAGATCTAGGAACCTATGTGATCAACAAG

CAGACGCCAAACAAGCAAATCGGCTATCTTCTCCATCCAGTGGACCTA

AGCGTTATGACTGGACTGGGAAAAACTGGGTGTTCTCCCACGACGGCGT

GTCCCTCCATGAGCTGCTGGCCGCAGAGCTCACTAAAGCCTTAAAAACC

AAACTGGACTTGTCTTGGTTGGCCTATTCCGGAAAAGATGCTTGA,

GenBank Accession No.: U95736.1, Mus musculus
frataxin mRNA, complete cds, which provides the
nucleic acid sequence (SEQ ID NO: 3):
CGGCCGCGGAGCTGGAGTAGCATGTGGGCGTTCGGAGGTCGCGCAGCCG

TGGGCTTGCTGCCCCGGACGGCGTCCCGGGCCTCCGCCTGGGTCGGGAA

CCCGCGCTGGAGGGAACCGATCGTAACCTGCGGCCGCCGAGGCCTACAT

GTCACAGTCAACGCCGGCGCCACCCGCCACGCCCATTTGAACCTCCACT

ACCTCCAGATTCTGAACATCAAAAAGCAGAGCGTCTGCGTGGTGCATTT

GAGGAACTTGGGGACATTGGACAACCCAAGCTCTCTAGACGAGACAGCG

TATGAAAGACTGGCGGAAGAGACCCTGGACTCCCTGGCCGAGTTCTTTG

AAGACCTCGCAGACAAGCCCTATACCCTGGAGGACTACGATGTCTCTTT

TGGGGATGGCGTGCTCACCATTAAGCTGGGCGGGATCTAGGGACCTAC

GTGATCAACAAGCAGACCCCAAACAAGCAAATCTGGCTGTCTTCTCCTT

CCAGCGGCCCCAAGCGCTATGACTGGACCGGGAAGAACTGGGTGTACTC

TCATGACGGCGTGTCTCTGCATGAGCTGCTGGCCAGGGAGCTGACTAAA

GCTTTAAACACCAAACTGGACTTGTCTTCATTGGCCTATTCTGGAAAAG

GCACTTGACTGCCAGCCAGATTCCAAGACATTAAACACTGTCAGGTGAA

GACCCCCAGCCTCCTCCTGTAGCTGAATGTCTGCCTTCCCATACCTGCT

CCTGAAGATAGTCACACCGTGTGTGACAGCTCTGTGAAAAAGTGTGTT

CCCTCCCACCCTGTCCCCGGACCTGGCTCTTCATTTCTACAGACATTTG

TTAGGATTATGTCATTTGCTCCCCAACCTGAGACCTCTGGTCTCTTAGA

AAGTCTTATATGCTGGGCAGTGGTGGCGCACGCCTTTAATCCCAGCACT

CGGGAGGCAGAGGCAGGCGGATTTCTGAGTTGGAGGCCAGCCTGGTTTA
```

-continued

CAGAGTGAGTTCCAGGACAGCCAGGACTACACAGAGAAACCCTGTGTCG

AAAAAAAAAAAAAAAAAAAGAAAGAAAGAAAGTCTTACACCACAAGTGT

GTCCATGATATAACAGCC,
and

GenBank Accession No.: U95736.1:22-645 *Mus musculus* frataxin mRNA, complete cds, which provides the nucleic acid sequence (SEQ ID NO: 4):
ATGTGGGCGTTCGGAGGTCGCGCAGCCGTGGGCTTGCTGCCCCGGACGG

CGTCCCGGGCCTCCGCCTGGGTCGGGAACCCGCGCTGGAGGGAACCGAT

CGTAACCTGCGGCCGCCGAGGCCTACATGTCACAGTCAACGCCGGCGCC

ACCCGCCACGCCCATTTGAACCTCCACTACCTCCAGATTCTGAACATCA

AAAGCAGAGCGTCTGCGTGGTGCATTTGAGGAACTTGGGGACATTGGA

CAACCCAAGCTCTCTAGACGAGACAGCGTATGAAAGACTGGCGGAAGAG

ACCCTGGACTCCCTGGCCGAGTTCTTTGAAGACCTCGCAGACAAGCCCT

ATACCCTGGAGGACTACGATGTCTCTTTTGGGGATGGCGTGCTCACCAT

TAAGCTGGGCGGGGATCTAGGGACCTACGTGATCAACAAGCAGACCCCA

AACAAGCAAATCTGGCTGTCTTCTCCTTCCAGCGGCCCCAAGCGCTATG

ACTGGACCGGGAAGAACTGGGTGTACTCTCATGACGGCGTGTCTCTGCA

TGAGCTGCTGGCCAGGGAGCTGACTAAAGCTTTAAACACCAAACTGGAC

TTGTCTTCATTGGCCTATTCTGGAAAAGGCACTTGA.

In another aspect, the method of treating a mitochondrial disease or disorder in a subject includes contacting cells expressing hFXN from the subject with a vector encoding a gene editing system that when transfected into the cells removes a trinucleotide extension mutation of endogenous hFXN, thereby treating the mitochondrial disease or disorder. In various embodiments, the gene editing system is selected from the group consisting of CRISPR/Cas, zinc finger nucleases, and transcription activator-life effector nucleases. The step of contacting may be performed ex vivo by first obtaining a sample of cells from the subject, transfecting the gene editing system into the sample of cells, and thereafter transplanting the transfected cells into the subject, thereby treating the mitochondrial disease or disorder. The sample of cells may be any cells expressing hFXN, such as, for example, blood cells or HSPCs of the subject.

In addition to lysosomes, mitochondria can readily be transferred via tunneling nanotubes (TNTs). Using the YG8R mouse model, it was therefore tested if HSPC transplantation could rescue FRDA. The premise is that mitochondrial cross-correction would occur in all injured tissues via TNTs generated by HSPC-derived macrophages. YG8R mice are currently considered the best animal model of FRDA as they express only the human mutated frataxin containing 280 GAA repeats (SEQ ID NO: 14), without endogenous murine frataxin, fxn$^{-/-}$ FXN$^+$. This mouse model exhibits a decrease of 57% frataxin expression resulting in a mild progressive phenotype including ataxia, and coordination and locomotor anomalies similar to the clinical manifestations in FRDA patients. The mice display a degeneration of the large sensory neurons of DRG, and decrease in aconitase activity and increase of oxidized proteins in the brain, heart and skeletal muscle. Thus, the advantages of this mouse model, compared to tissue-specific conditional FXN knockout models for FRDA, are that the genetic defect is similar to that of humans and that the impact of stem cell therapy is tested in the CNS, heart and skeletal muscle in the same animal model. The impact of HSPC transplantation in YG8R mice has been impressive as the neurological complications and muscle weakness were fully rescued in the treated mice, with functional, histological and biochemical properties comparable to wild-type (WT) mice.

The present disclosure also demonstrates that HSPCs differentiated into phagocytic cells in the brain, spinal cord, DRG, muscle and heart and transferred frataxin to the adjacent disease cells. These data represent the first proof of concept that FRDA can be treated by HSPC transplantation and the first treatment strategy resulting in physiologic rescue of the complications associated with FRDA in a mouse model.

Given the high risk of morbidity and mortality associated with allogeneic HSPC transplantation, it remains an uncertain therapeutic choice for many diseases after consideration of the risk/benefit ratio. The major complication is graft-versus-host disease (GVHD), acute GVHD grade II-IV occurred in 20% to 32% of patients and chronic GVHD in 16% to 59%, both significantly impacting survival of the recipients. Moreover, high risks of infection related to the myeloablative regimen and immunosuppressive medications account for 16% to 19% of deaths. Since it avoids the risks of immune rejection and GVHD, autologous HSPC transplantation is a safer approach. Thus, in the case of cystinosis, an autologous HSPC transplantation was developed using a self-inactivated (SIN)-lentivirus vector (LV) containing human CTNS cDNA and tested this strategy in the Ctns$^{-/-}$ mice. It was therefore shown that transduced cells were capable of decreasing cystine content in all tissues and led to kidney function improvement. In vitro studies using human CD34+ HSPCs isolated from peripheral blood of healthy donors and cystinosis patients have now completed, and the serial transplantation in the Ctns$^{-/-}$ mice has been significantly advanced.

Accordingly, the present disclosure provides a method for autologous transplantation of ex vivo gene-modified HSPCs to introduce a functional frataxin. In various embodiments, the method involves use of a pCCL SIN-LV vector or gene editing to remove a trinucleotide extension mutation of endogenous hFXN in the HSPCs. As demonstrated herein, this approach has proven effective in the YG8R mouse model. This represents a unique treatment approach for FRDA that should lead to a clinical trial for this disease after completing the pharmacology/toxicology studies. Gene therapy approaches for FRDA have already been tested in vitro and in vivo with successful outcomes. Infection of human fibroblasts derived from FRDA patients with different viral vectors, adeno-associated virus (AAV), LV or herpes simplex virus type 1 (HSV-1), containing human FXN (hFXN) cDNA or full genomic DNA resulted in the partial or complete restoration of the WT cellular phenotype in response to oxidative stress. Human FXN cDNA delivery in the nervous system of conditional neuronal fxn-knockout mice using HSV-1 vector led to the complete recovery in motor coordination. Intraperitoneal injection of AAV-9 vector containing hFXN cDNA in the cardiac and skeletal muscle conditional frataxin-knockout mouse model (MCK mice), doubled the life span of the mice and improved their cardiac function. It has been recently reported that complete prevention and reversal of severe cardiomyopathy in MCK mice by has been achieved by intravenous injection of AAV9-hFXN cDNA.

In contrast to the gene therapy approaches tested so far for FRDA, the present disclosure provides use of a SIN-LV or gene editing to correct HSPCs for a systemic therapeutic strategy. Vectors derived from lentiviruses have supplanted γ-retroviral vector for gene therapy due to their superior gene transfer efficiency and better biosafety profile. Indeed, all cases of leukemogenic complications observed to date in clinical trials or animal models involved the use of retroviral vectors with LTR containing strong enhancer/promoters that can trigger distant enhancer activation. In contrast, the third-generation of lentivirus vectors, SIN-LV, with the deletions in their LTR, contains only one internal enhancer/promoter, which reduces the incidence of interactions with nearby cellular genes, and thus, decreases the risk of onco-genic integration. SIN-LV are also designed to prevent the possibility of developing replication competent lentivirus (RCL) during production of viral supernatants with three packaging plasmids necessary for production. Lentivirus vectors efficiently transduce HSPCs and do not alter their repopulation properties, which make this type of vector an attractive vehicle for stem cell gene therapy.

Clinical trials using SIN-LV to gene-correct human HSPCs are being undertaken in the U.S. and Europe for several conditions including HIV-1, β-thalassemia, immune deficiencies, metabolic diseases and cancers. For immune deficiency disorders, 35 patients have been transplanted with SIN-LV-modified HSPCs so far. A clinical trial in patients with Adrenoleukodystrophy (ALD) has achieved stable gene correction in ~20% of hematopoietic cells in two patients. Cerebral demyelination was arrested without further progression over three years of follow-up, which represents a clinical outcome comparable to that observed after allogeneic transplantation; there was no evidence of clonal dominance. Recently, a clinical trial for Wilskott-Aldrich syndrome was reported in three patients 32 months post-transplantation. Stable and long-term engraftment of the gene-modified HSPCs (25-50%) resulted in improved platelet counts, protection from bleeding and infections, and resolution of eczema. Another clinical success was recently reported in three pre-symptomatic patients with Metachromatic Leukodystrophy. Transduced cell-derived blood cell engraftment achieved 45 to 80%, and up to 24 months later, protein activity was reconstituted to above normal values in cerebrospinal fluid associated with a clear therapeutic benefit.

Because Friedreich's ataxia is a monogenic disease caused by a shortage of the frataxin protein, gene therapy appears to be a promising alternative treatment. The recent gene therapy successes using AAV vectors in the MCK mice not only prevented heart failure when given to presymptomatic animals, but also reversed the cardiomyopathy when given after the onset. While encouraging, this approach presents potential safety and logistic concerns: i) localized delivery by direct viral injection to affected sites poses certain challenges in accessing sites such as heart and brain and leads only to tissue-specific rescue, ii) systemic AAV delivery remains difficult in humans due to the high levels of vector necessary, leading to vector synthesis and safety concerns. In contrast, HSPC gene therapy approach has the key advantages: i) it treats all the complications by a single infusion of stem cells, ii) gene-correction will occur ex vivo in a controlled environment allowing cell characterization prior to transplantation, iii) gene-corrected HSPCs will reside in the bone marrow niche after transplantation where they will self-renew and become a reservoir of healthy cells for the lifespan of the patients, iv) it avoids immune reaction as compared to allogeneic transplantation. Thus, autologous HSPC gene therapy could provide a cure for the lethal disease FRDA for which no treatment currently exists.

Another innovative aspect provided herein is the use of HSPCs as delivery vehicles for functional mitochondrial genes. Many diseases such as metabolic, cancer, cardiovascular and neurodegenerative disorders are associated with mitochondrial dysfunction. Inherited mitochondrial diseases are relatively frequent and affect 1 in every 5,000 children, often causing fatal illnesses. While many attempts have been made to deliver healthy mitochondria to diseased cells and tissues, the efficacy of such approaches has been limited and usually short-term.

The present disclosure demonstrates that one single systemic transplantation of WT HSPCs in young adult YG8R mice fully prevents the development of FRDA pathology including neurobehavioral deficits, muscle weakness and degeneration of DRG sensory neurons. One advantage of exogenous HSPC transplantation is the capacity of these cells to permanently replace/repopulate the marrow and migrate from their niche to differentiate into phagocytic cell types within multiple diseased tissues. HSPCs can even transmigrate across the blood brain barrier and engraft within the CNS as differentiated microglia. This phenomena is enhanced by tissue injury and even by the use of busulfan-mediated myeloablation, as opposed to total body irradiation, which enhances the clinical relevance of this work for the treatment of FRDA. Consistently, it has been shown that transplanted HSPCs differentiate into microglial cells within the CNS of the YG8R mice but also macrophages in DRG, peripheral nerves, skeletal muscle and heart, the primary sites of FRDA pathological complications.

Restoration of mitochondrial function in WT HSPC-treated mice as compared to YG8R controls was evidenced by biochemical, molecular and histological studies. First, significant reduction in oxidative stress was observed in WT HSPC-treated YG8R tissues as compared to control littermates. Oxidative stress is a major component in FRDA pathogenesis and likely to account for neuronal preservation. Oxidative stress has also recently been shown to induce DNA damage and elevation of Poly (ADP-Ribose) Polymerase-1 (PARP-1) expression in frataxin-deficient microglial cells, which increased microglial activation. Because PARP1 activation leads to increased inflammatory cytokine expression in microglial cells, these findings suggest that oxidative stress may induce neuroinflammatory-mediated neurodegeneration in FRDA. Hence, the robust neurological phenotype rescue demonstrated herein in HSPC-treated YG8R may partially be due to the replacement of the frataxin-deficient microglial cells by wild-type microglia, another potential advantage of this therapeutic strategy. Mitochondrial function was also assessed by mitochondrial PCR array profiling in the cerebrum of the mice. The findings provided herein show largely upregulated genes >2 fold change in YG8R mice compared to WT (13 genes out of 84 total) while very few changes were identified between WT and YG8R/WT HSPCs mice (4 genes) and for none the difference was significant. The significantly upregulated genes in YG8R vs WT include three solute mitochondrial carrier family 25 genes, Mipep, an important component of the human mitochondrial import machinery implicated in developmental delay and the fatty acid transporter Cpt1b, which is upregulated in stress and Post-Traumatic Stress Disorder. Finally, cellular iron metabolism dysregulation is evidenced in FRDA by the presence of iron deposits in cardiomyocystes of patients (Lamarche, et al. Lemieux, The cardiomyopathy of Friedreich's ataxia morphological observations in 3 cases. *The Canadian journal of neurological sciences. Le journal canadien des sciences neurologiques* 7, 389-396 (1980)). Similarly, the present disclosure demonstrates the presence of abundant iron deposition in heart sections from YG8R controls while very few were observed in WT and YG8R/WT HSPCs mice, suggesting normal iron metabolism in the treated YG8R mice. In contrast, preclinical and clinical data using an iron chelator are sometimes opposite in function of the dosage (Pandolfo, et al., Deferiprone for the treatment of Friedreich's ataxia. *J Neurochem* 126 Suppl 1, 142-146 (2013)). These data demonstrate correction of mitochondrial function in the different affected tissues in FRDA, brain, skeletal muscle and heart, after one single systemic transplantation of WT HSPCs.

The data provided herein strongly suggest that frataxin cross-correction mechanism is involved in FRDA phenotype rescue after WT HSPC transplantation. Indeed, the evidence demonstrates abundant transfer of the mitochondrial frataxin from the HSPC-derived microglia/macrophages to neurons in brain, spinal cord, and DRGs, and myocytes in skeletal muscle and heart. The data also demonstrates the transfer of the non-related mitochondrial protein Cox8, showing non-selective transfer of mitochondrial proteins occur.

As discussed above, it has previously been reported that HSPC-derived macrophages engrafted in kidney could deliver cystinosin-containing lysosomes to proximal tubular cells via TNTs in the mouse model of cystinosis. In this context, TNTs crossing the basement membrane was the only route possible across the continuous, thick, dense tubular basement membrane to access the tubular cells. Transfer of mitochondria via TNTs has previously been shown in vitro in response to cellular stress, and this prompted the testing of HSPC transplantation in FRDA. Here, it has been shown in culture that frataxin-bearing mitochondria could be transferred via TNT intercellular connections from macrophages to frataxin-deficient cells. In vivo, it has been observed that the mitochondrial proteins frataxin and Cox8 conjugated with GFP within host neurons, demonstrating neuronal cross-correction from microglial cells, which is efficient as about 50% of neurons contained Cox8-GFP in the spinal cord. Several routes have to be considered for this transfer: i) Vesicular exchange of genetic material, messenger RNAs were shown to be transferred from graft-derived microglia to neurons via extracellular vesicles/exosome shedding; ii) Release of mitochondria-containing vesicles, this was previously shown from mesenchymal stem cells to pulmonary alveoli in acute lung injury model, or more recently from astrocytes to neurons in a cerebral ischemia model; iii) Microglia-to-neuron transfer of mitochondria via the microglial branch extensions directly in contact with neurons. While this route has not yet been considered, the data presented herein suggest that this is a possible mode of transfer. Indeed, it has been shown that the mitochondrial proteins Cox8-GFP and FXN-GFP were transferred to neurons and that GFP punctae were also present within the DsRed$^+$ microglial branch extensions. Moreover, it has been shown that most of the neurons containing GFP$^+$ mitochondria were in contact with the DsRed$^+$ microglial branch extensions. Microglial processes are dynamic, actively retracting and expanding, and capable of making direct contact with neurons, especially in context of injury, during which the duration of the contact is prolonged, supporting this hypothesis.

Thus, this strategy turns HSPCs into intelligent and widespread delivery vehicles to obtain stable and sustained cross-correction after their differentiation into microglia/macrophages in the brain, spinal cord, DRG, skeletal muscle and heart. This work also demonstrates the transfer of frataxin from LV-hFXN-GFP-transduced HSPCs to diseased neurons and represents the first proof of concept for the development of a HSPC gene therapy strategy for mitochondrial disorders such as FRDA.

The following examples are intended to illustrate but not limit the invention.

Example 1

Treatment of FRDA Mouse Model Using HPSC Transplantation

Systemic transplantation of wild-type HSPCs prevents onset of locomotor deficits in YG8R mice. To assess the effects of HSPC transplantation on FRDA, the YG8R mouse model expressing the mutant human FXN gene containing 280 GAA repeats (SEQ ID NO: 14), and lacking endogenous murine frataxin, mfxn$^{-/-}$ hFXN$^+$ was used. Lethally irradiated 2 month-old YG8R mice were transplanted with wild-type (WT) GFP-expressing HSPCs (n=13) and donor-derived blood cell engraftment ranged from 35 to 96% as determined by flow cytometry. Mice are sacrificed for analysis at 7 months post-transplantation, i.e., at 9 months of age. As controls, WT littermates (n=17), untreated YG8R (n=4) or lethally irradiated YG8R mice transplanted with mfxn$^{-/-}$ hFXN$^+$ HSPCs (n=5) were analyzed. All the mice were assessed by behavioral testing at 5 months old (3 months post-transplant), and 8 WT, 4 YG8R (3 untreated and 1 transplanted with mfxn$^{-/-}$ hFXN$^+$ HSPCs) and 3 YG8R mice transplanted with WT HSPCs were analyzed at 9 months old.

Progressive neurodegeneration in FRDA patients leads to loss of motor skills and progressive muscle degeneration. The YG8R mouse replicates human FRDA neurological symptoms such as coordination deficits from three months of age with a progressive decrease in locomotor activity. Thus, the effect of HSPC transplantation on performance of motor- and sensory-dependent functional tasks and on muscle strength at both 5 and 9 months of age was assessed (3 and 7 months post-transplantation, respectively). No difference was observed in performance in any of the behavioral tests at either time point between untreated YG8R mice and those transplanted with mfxn$^{-/-}$ hFXN$^+$ HSPCs, indicating that neither irradiation nor transplantation with mfxn$^{-/-}$ hFXN$^+$ HSPCs ameliorate the disease phenotype. Compared to WT mice, YG8R mice (controls) and YG8R mice transplanted with mfxn$^{-/-}$ hFXN$^+$ HSPCs displayed significantly reduced open field locomotor activity, impaired coordination on rotarod, and alterations in gait as well as significantly decreased forelimb grip strength at both time points (FIG. 1A). In contrast, YG8R mice transplanted with WT HSPCs exhibited normal locomotor activity and muscle strength at both 3 and 7 months post-transplantation (FIG. 1A). Interestingly, and in contrast to previous findings in the cystinosis model, the YG8R mouse exhibiting the lowest level of donor-derived blood cell engraftment still exhibited physiological rescue of the neurobehavioral deficits. Together, these data demonstrate that HSPC transplantation in 2-month-old YG8R mice completely rescued the progressive neurobehavioral and muscular deficits characteristic of this FRDA animal model.

Figure 1C:
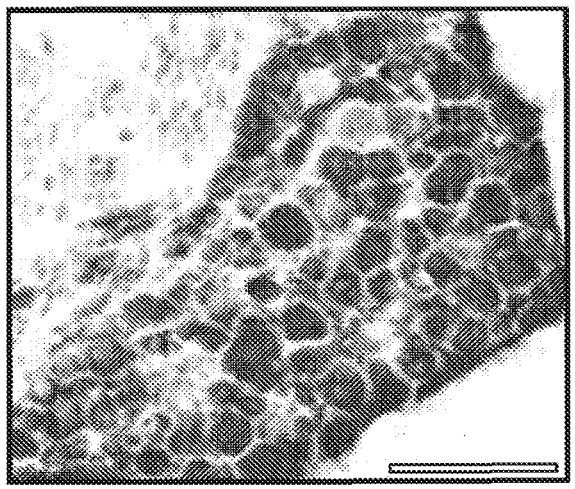
Figure 1C:
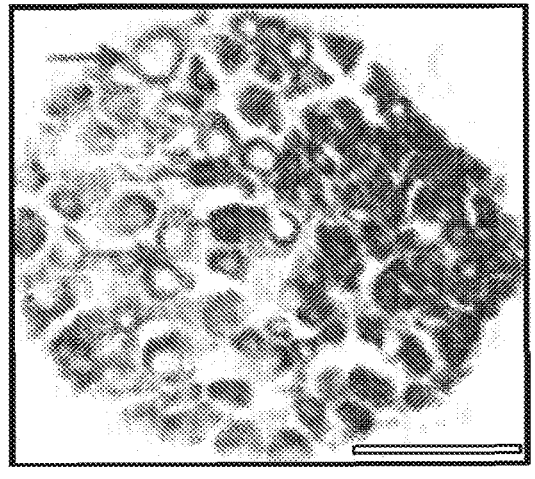
Figure 1C:
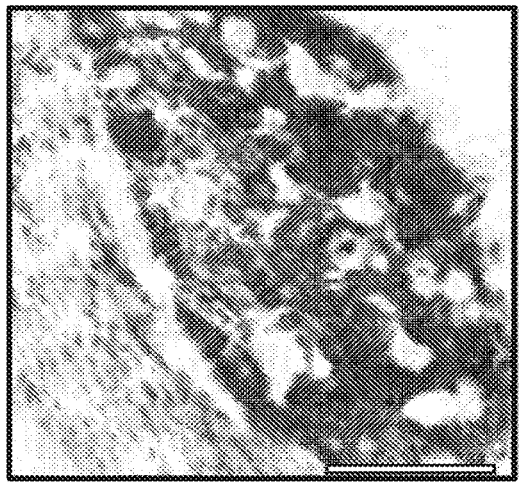
Figure 1C:
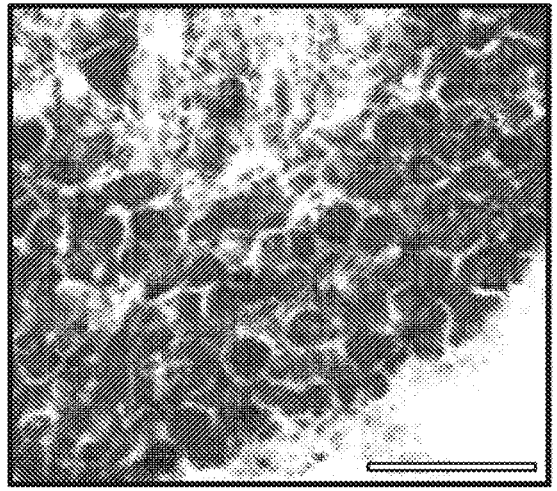
Figure 1C:
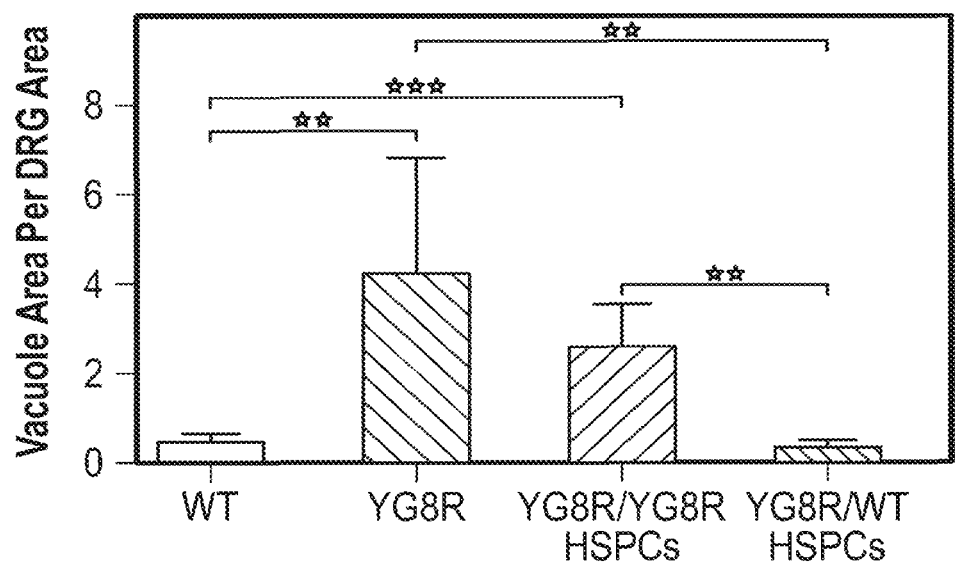

Neurodegeneration in FRDA involves primarily the sensory components of the central nervous system (CNS) and peripheral nervous system (PNS), beginning with loss of large sensory neurons in the dorsal root ganglia (DRG). Loss of sensory neurons in DRGs also occurs in YG8R mice and is characterized by the presence of large vacuoles. In 9-month-old control YG8R mice, vacuolar accumulation in L5 DRG neurons was detected with no significant difference in vacuole area between non-treated and mfxn$^{-/-}$ hFXN$^+$ HSPC-transplanted YG8R mice (FIG. 1C). In contrast, YG8R mice treated with WT HSPCs exhibited a significantly reduced vacuolar area that was comparable to WT mice (FIG. 1C). These data demonstrate that early transplantation of HSPCs prevents the degeneration of sensory neural cell bodies of the DRG in YG8R mice.

Figure 1D:
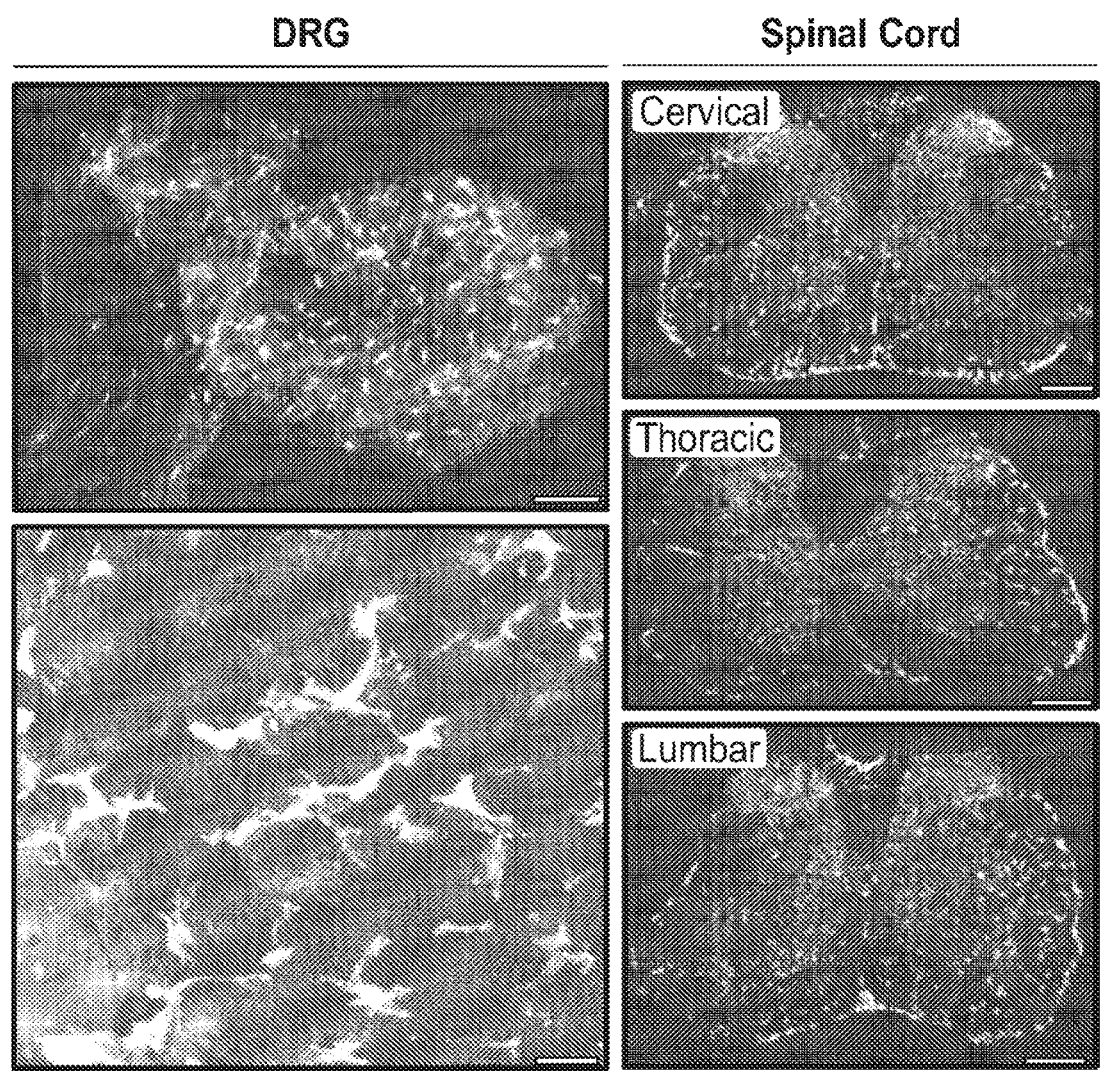
Figure 1E:
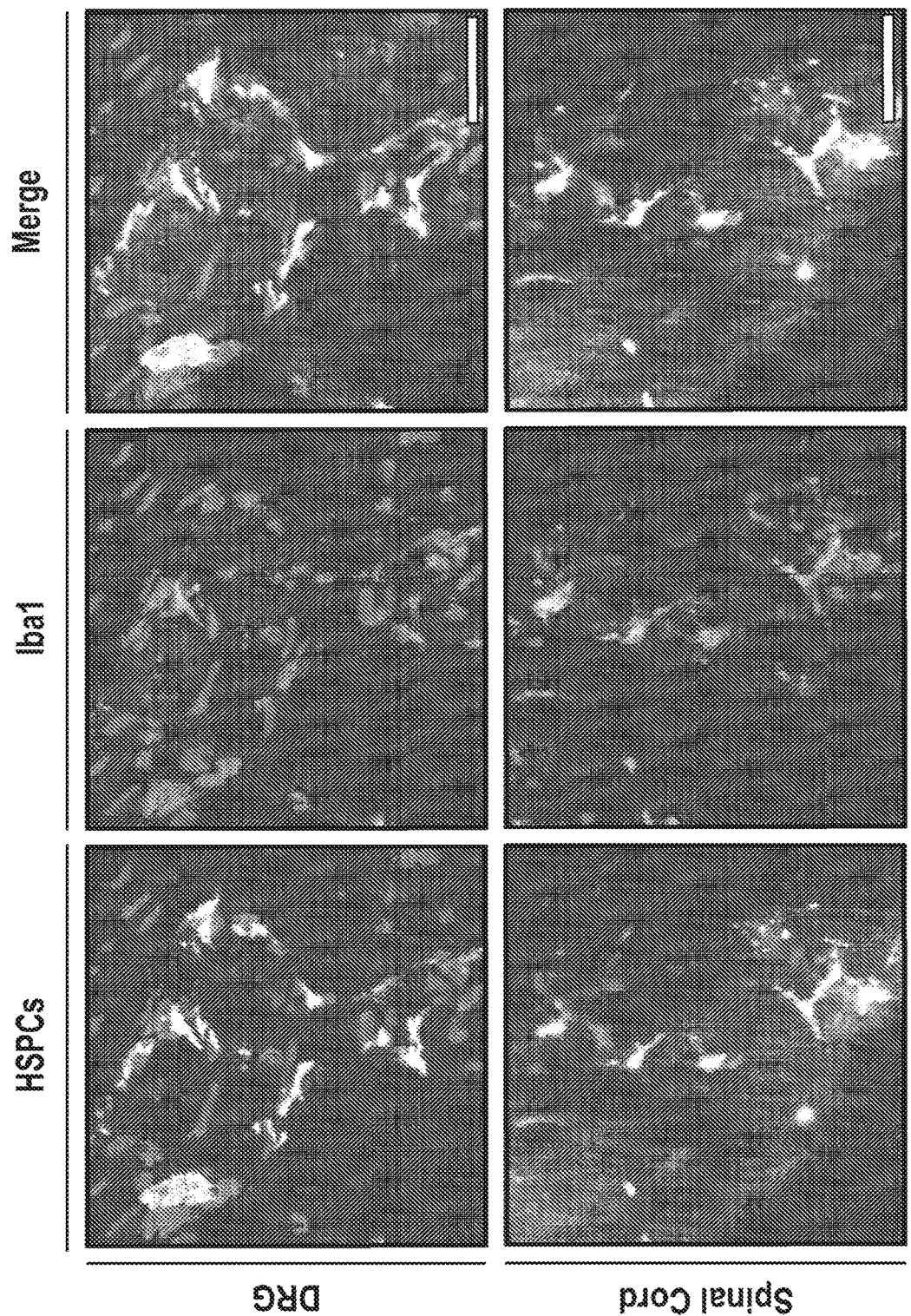
FIG. 1E shows confocal images of DRG and spinal cord sections of a GFP+ HSPC-treated YG8R mouse. Engrafted cells (GFP) are closely associated with neurons (NeuN), and co-localization with Iba1 marker; Scale bars: 30 µm.
Figure 5:
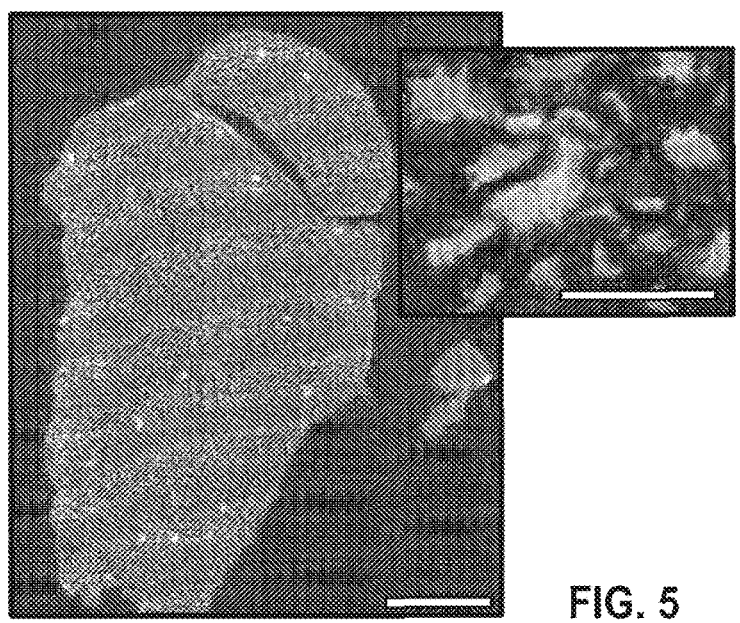
FIG. 5 is a pictorial diagram showing that HSPCs engraft in the peripheral nerve in YG8R mice. Confocal images of sciatic nerve from WT GFP+ HSPC-transplanted YG8R mice labeled with anti-GFP, and with a neurofilament marker, anti-NF200, and a myelin basic protein marker, anti-MBP. Scale bars: 100 μm (left), 10 μm (inset).
Figure 6A:
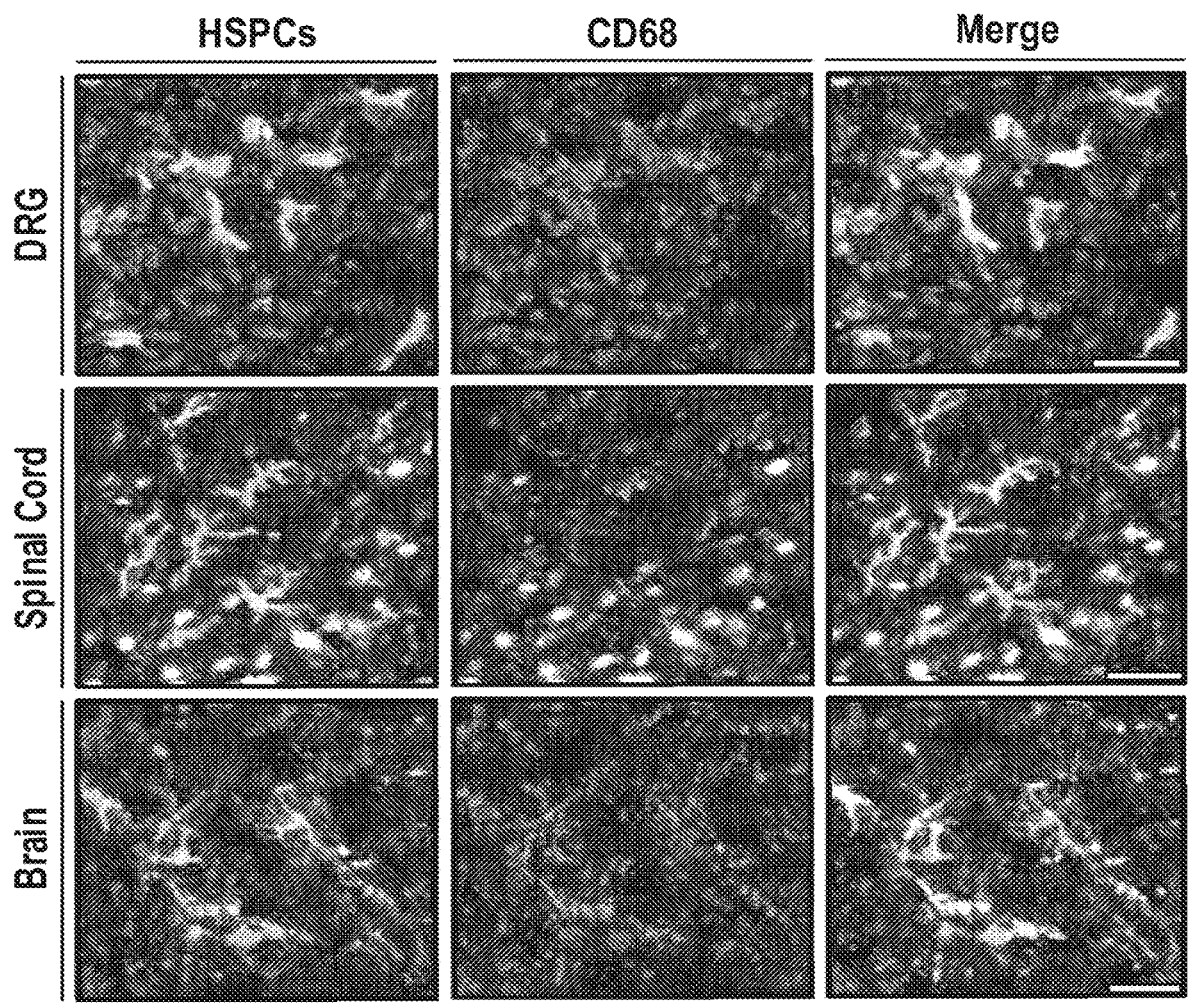
FIGS. 6A-6F are pictorial diagrams showing that HSPCs differentiate into macrophages in DRG and microglia in the spinal cord and brain.
Figure 6B:
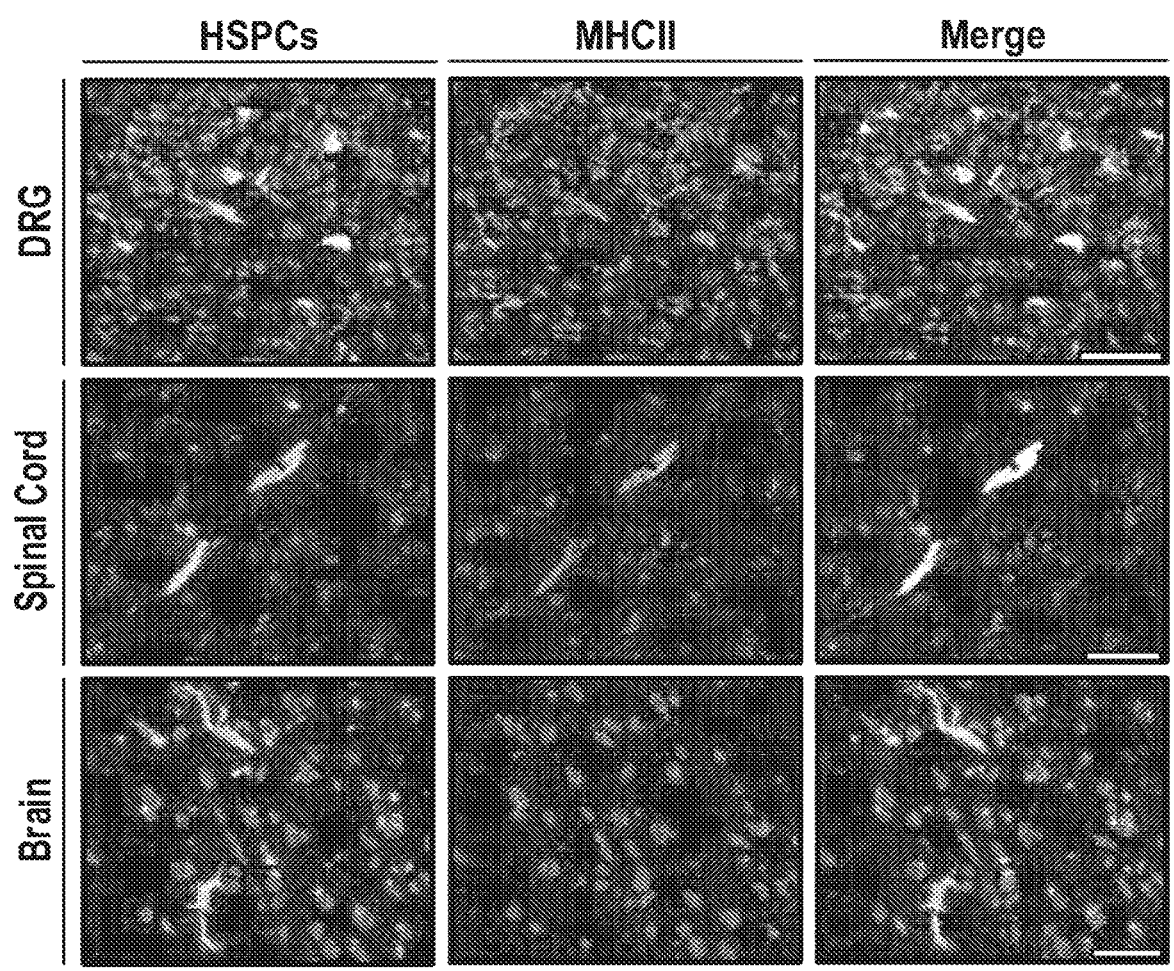
Figure 6C:
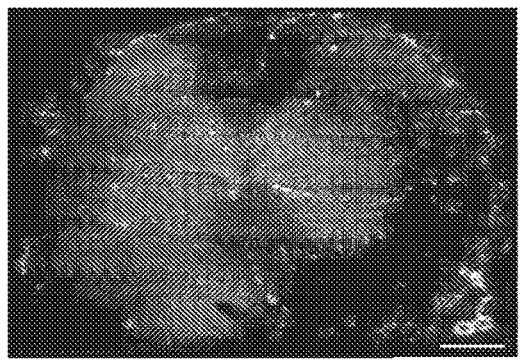
Figure 6D:
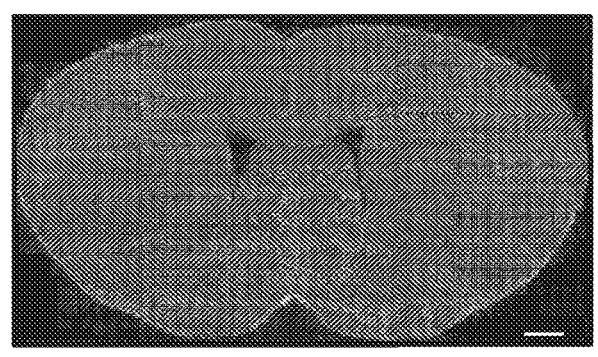

HSPCs differentiate into phagocytic cells after engraftment in the nervous system. Because FRDA affects the central nervous system (CNS) in addition to peripheral sensory neurons, the engraftment and differentiation of HSPCs was investigated in different regions of the nervous system. It was found that substantial engraftment of GFP$^+$ HSPC-derived cells within the DRGs, spinal cord and peripheral nerves (FIGS. 1C and 5). Within DRGs at all levels, donor cells were found in close proximity to neurons and were immunoreactive for the macrophage markers CD68 and MHCII, as well as Iba1, characterizing these cells as DRG resident macrophages (FIGS. 1D, 1E, 6A and 6B). In the spinal cord, HSPC-derived cells were abundant in the ascending sensory axon tracts, within the dorsal and ventral roots, motor pools and dorsal spinal cord gray matter (FIGS. 1C and 1D). These cells were >99% Iba1$^+$ and CD68$^+$, while fewer cells expressed MHCII (~30%; FIGS. 6A-6C) indicating their microglial identity. 3D-visualization of engrafted spinal cord subjected to tissue clearing showed that a high concentration of engrafted HSPC-derived cells was found in close proximity to perivascular regions, suggesting that these cells infiltrate the CNS via the vasculature.

Figure 2A:
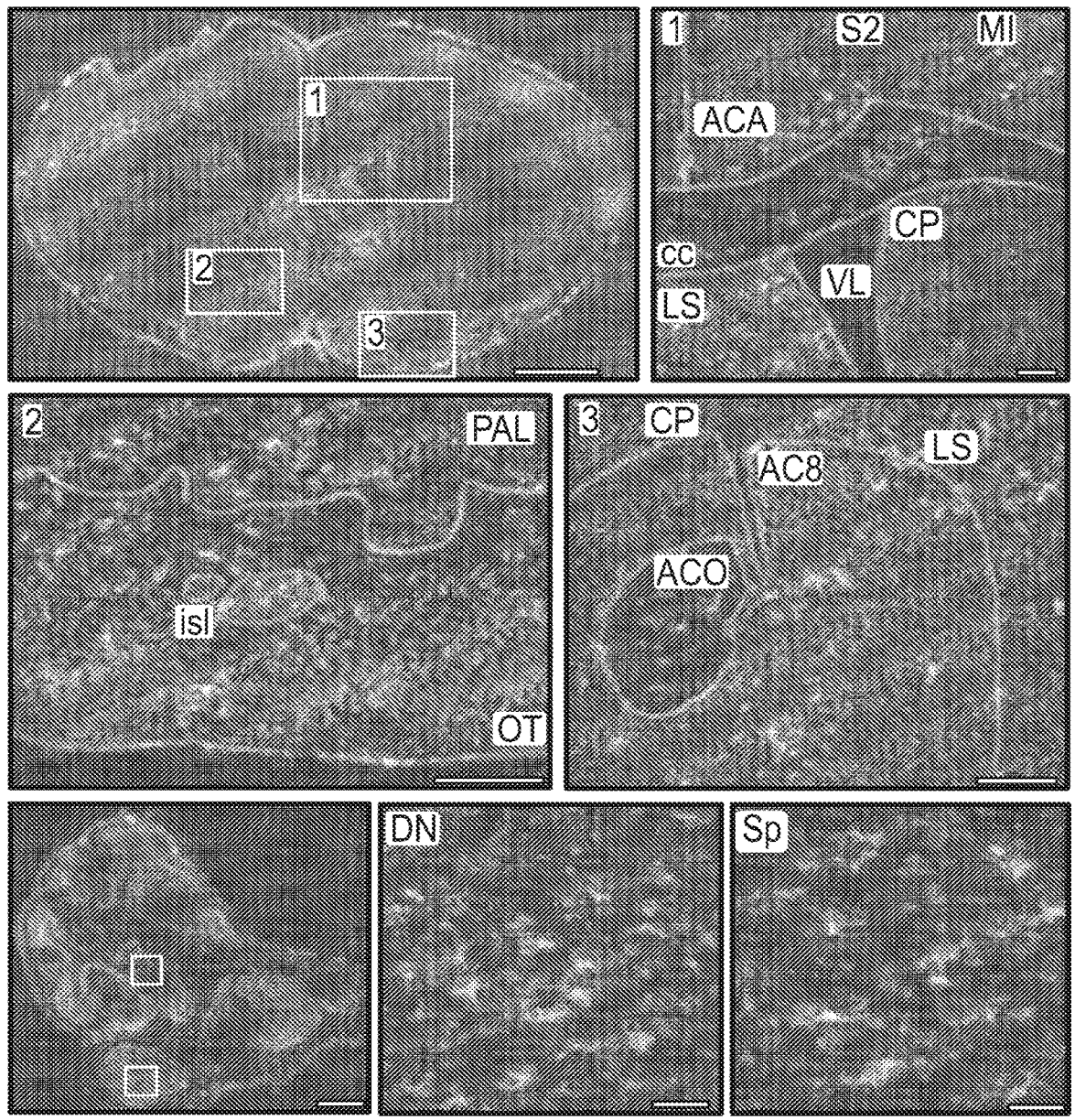
FIGS. 2A-2E are graphical and pictorial diagrams showing that transplanted HSPCs engraft throughout the brain and prevent frataxin-deficiency toxicity.
Figure 2B:
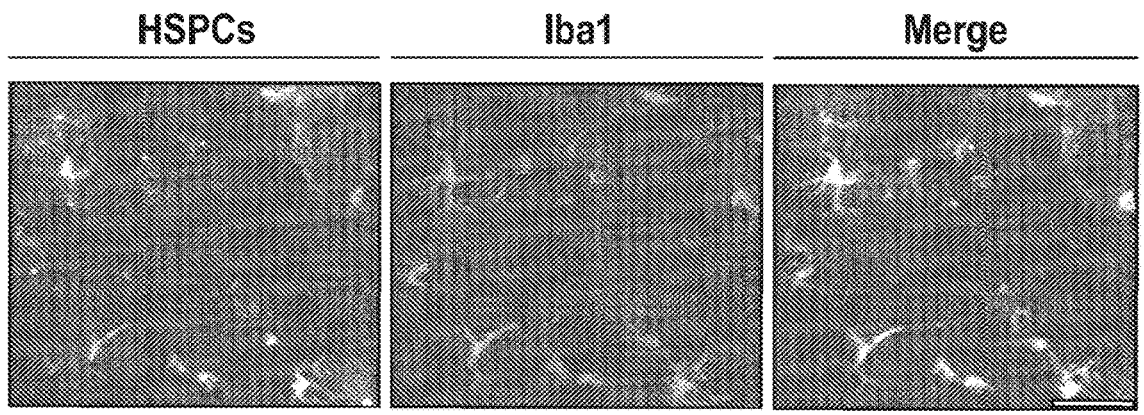
Figure 6E:
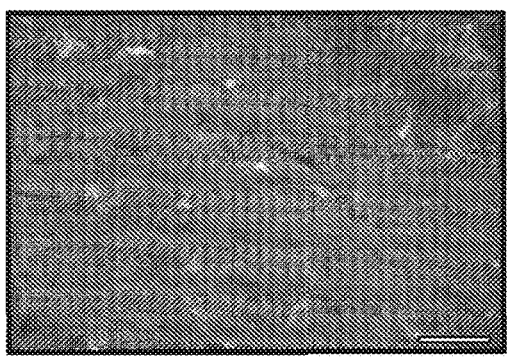
Figure 6F:
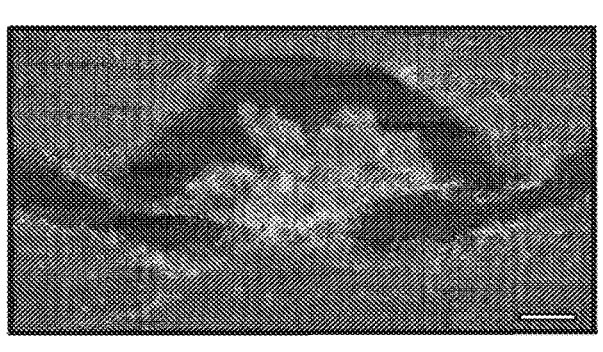

Graft-derived cells were also detected throughout gray and white matter in the brain, brainstem and cerebellum in treated YG8R mice (FIG. 2A). The vast majority (>99%) of HSPC-derived cells within all regions of the brain displayed the typical ramified morphology of microglia and expressed CD68 and Iba1, but were not immunoreactive for MHCII, demonstrating that these cells were microglial cells (FIGS. 2B, 6A, 6B and 6D). Perivascular infiltration in the brain was further demonstrated by the presence of GFP$^+$ HSPC-derived cells in close proximity of blood vessels (FIG. 6E) especially in the highly vascularized choroid plexus (FIG. 6F).

Figure 2C:
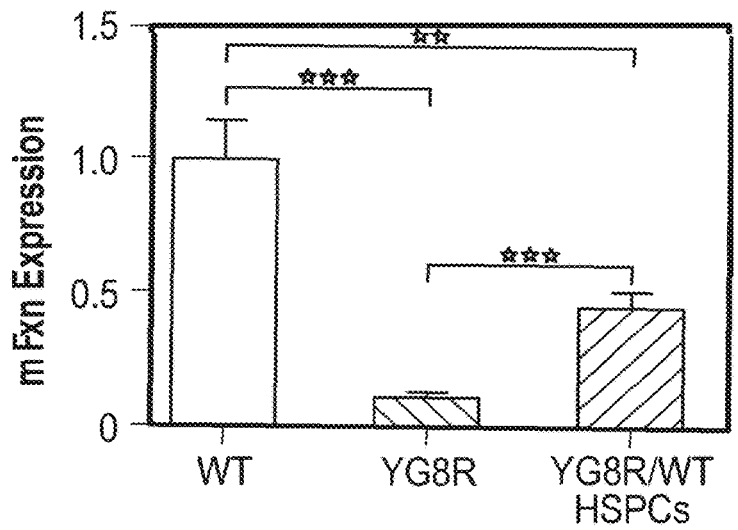
Figure 2D:
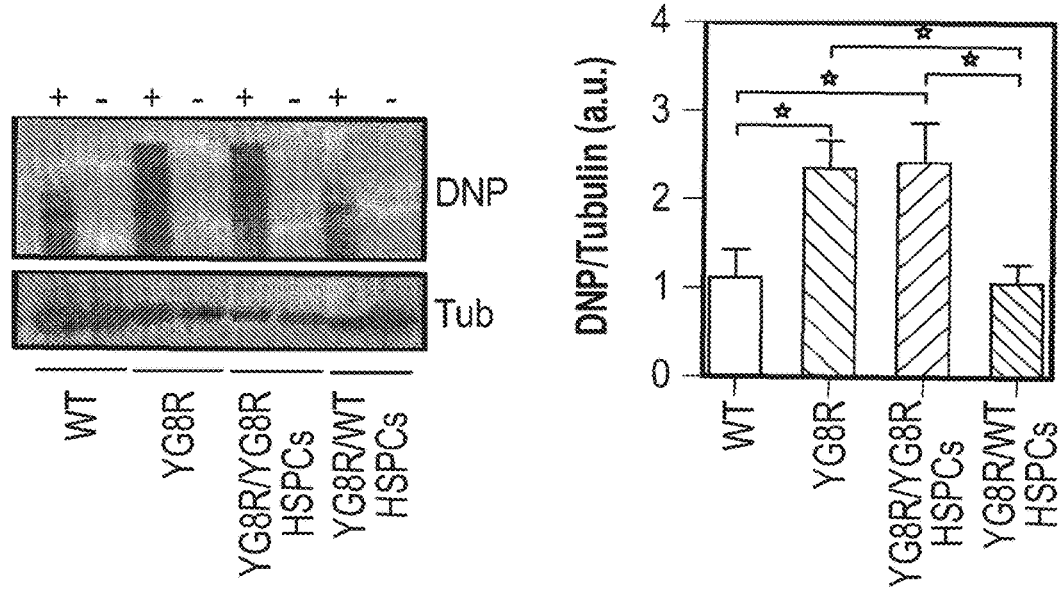

WT HSPC transplantation restores frataxin expression and mitochondrial function in the brain of YG8R mice. Murine frataxin (mFxn) expression analysis in the brain confirmed that tissue engraftment of the HSPC-derived cells correlated with partial restoration of mfxn expression in treated mice as compared to YG8R controls, although not up to WT expression levels; a residual expression was also detected in YG8R mice likely due to cross-reactivity with human FXN (FIG. 2C). Mitochondrial dysfunction in FRDA is associated with the presence of increased levels of oxidized proteins within tissues. Compared to WT controls, levels of oxidized proteins were significantly higher in the cerebrum of YG8R mice and YG8R mice transplanted with mfxn$^{-/-}$ hFXN$^+$ HSPCs (FIG. 2D). WT HSPC transplantation resulted in significant attenuation of oxidized protein levels in YG8R mice to a level comparable to WT, suggesting restoration of mitochondrial function in treated mice (FIG. 2D).

Figure 2E:
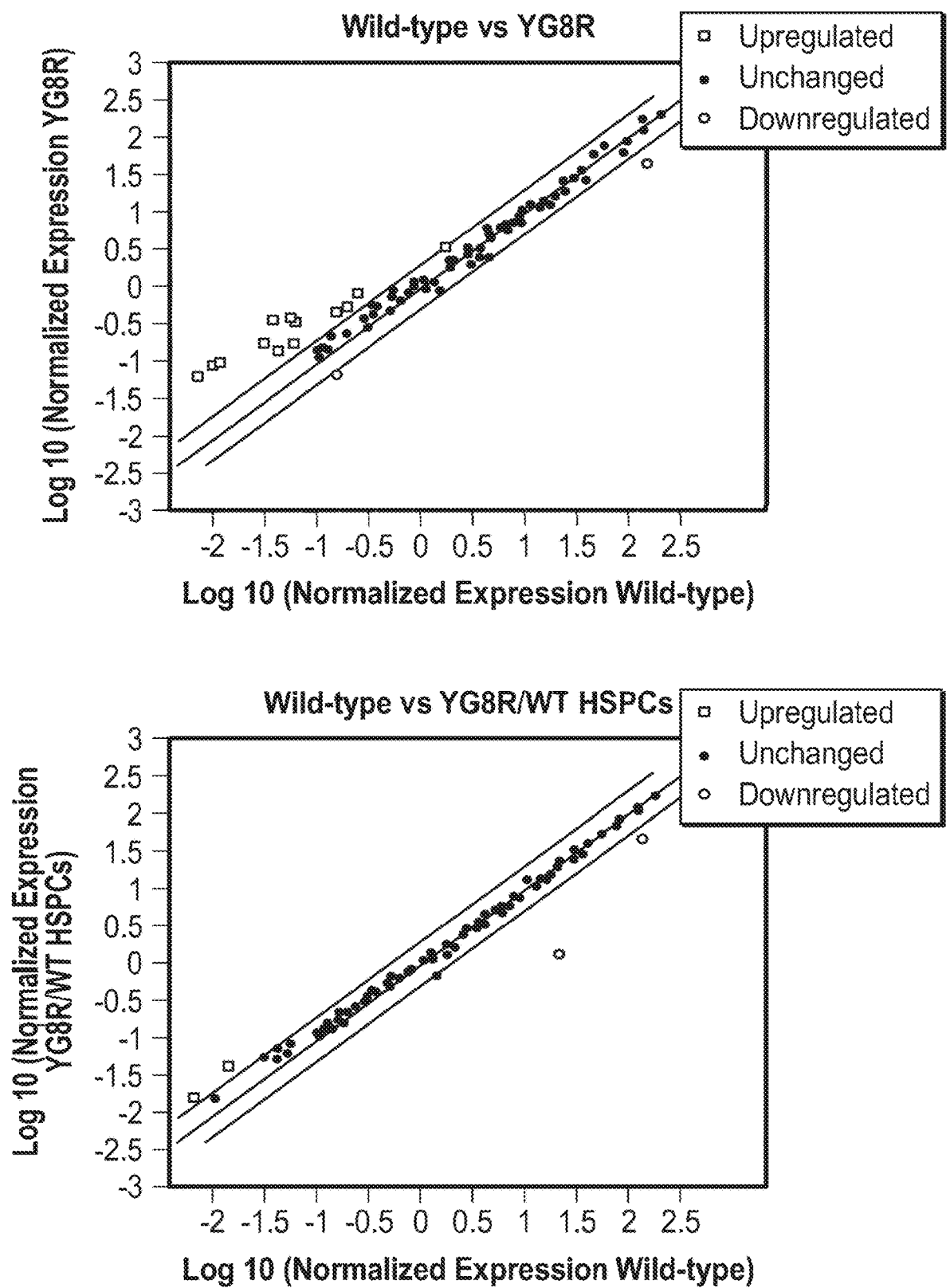
Figure 2E:
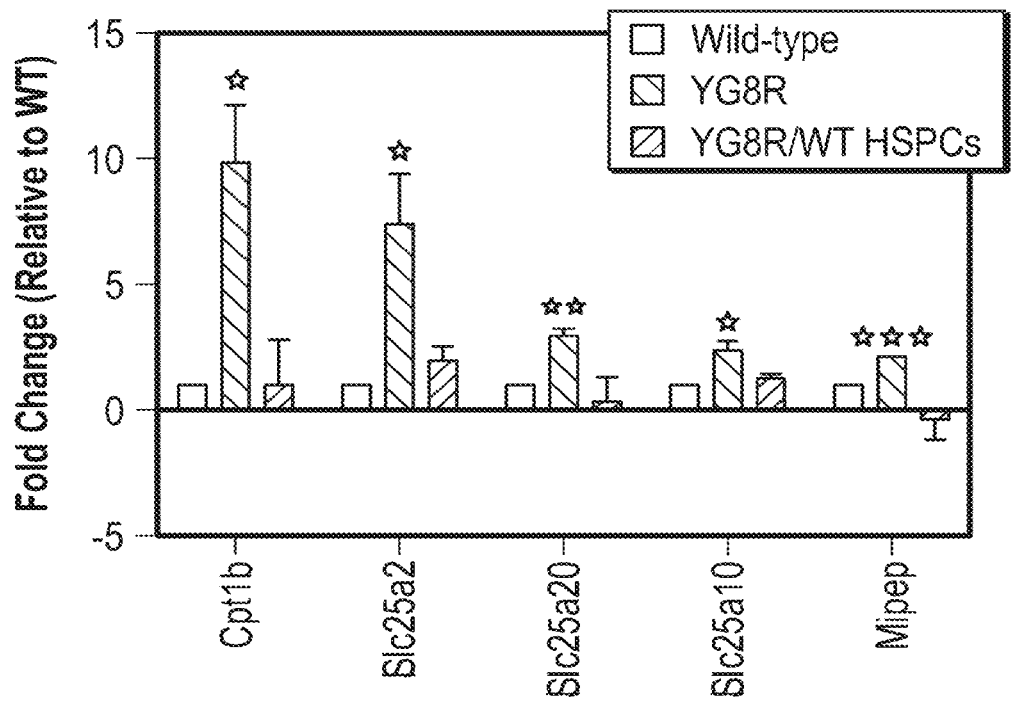

Additionally, mitochondrial function was assessed using mitochondrial PCR array profiling in the cerebrum of WT, YG8R, and YG8R/WT HSPCs. Expression of numerous mitochondrial genes crucial to a wide variety of processes ranging from control of apoptosis to oxidative phosphorylation were altered in the YG8R animals; out of 89 genes tested, 15.7% had at an increase of at least two-fold over WT, while only 4.4% were upregulated in treated animals (FIG. 2E). Of these genes, five were significantly upregulated genes were found in YG8R mice compared to WT, including several members of the SLC family of inner mitochondrial membrane transporters as well as other proteins involved in mitochondrial lipid metabolism (FIG. 2E). No significant difference was evidenced between YG8R/WT HSPCs and WT mice (FIG. 2E). The PCR array data findings reflect significant mitochondrial dysfunction in YG8R mice that is corrected in the WT HSPC-treated YG8R mice.

Figure 3A:
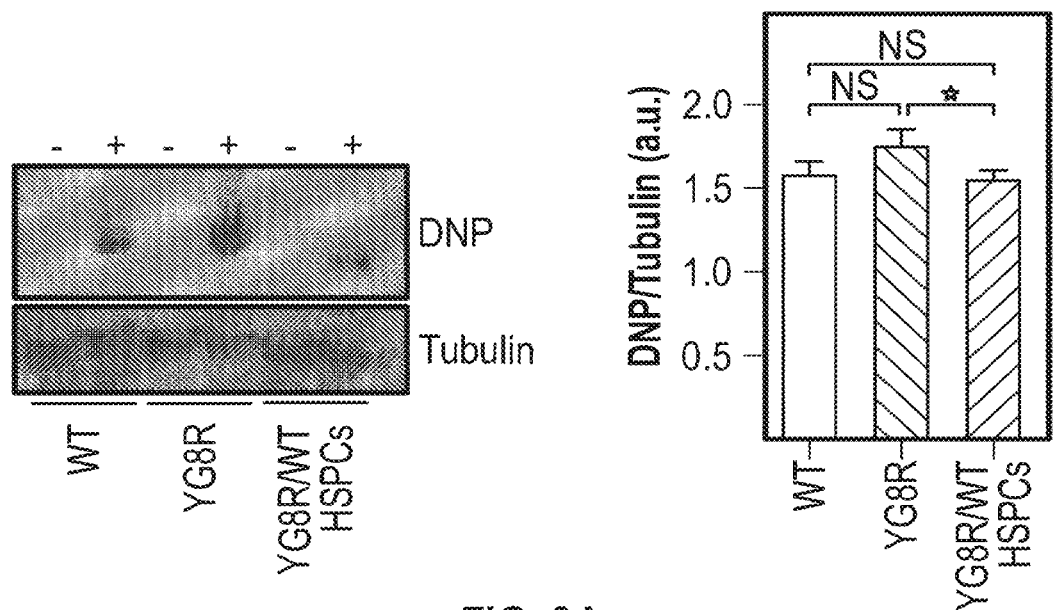
Figure 3B:
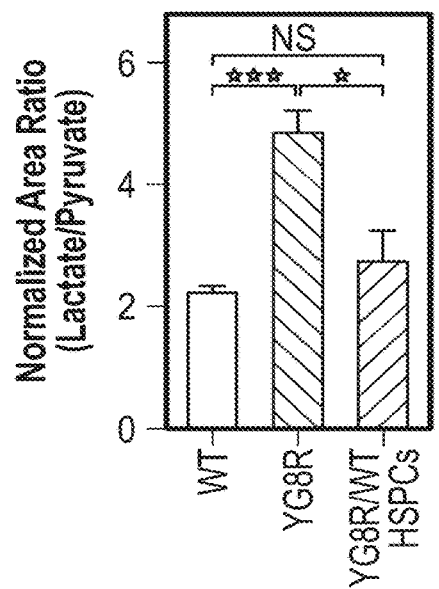

HSPCs engraft abundantly in heart and muscle of YG8R mice, restore mitochondrial function and improve skeletal muscle atrophy. Increased oxidized proteins was also demonstrated in skeletal muscle of YG8R controls (YG8R and YG8R/YG8R HSPCs; p=0.0798) relative to WT mice, although not significant, and normal level was found in the treated YG8R mice (FIG. 3A). Furthermore, lactate and pyruvate levels were measured by mass spectrometry analysis of skeletal muscle biopsies, a common assay for measuring impairment in oxidative metabolism, which was shown to be elevated in some mitochondrial diseases. A significant increase of lactate and lactate-to-pyruvate ratio in skeletal muscle of YG8R mice was demonstrated compared to WT mice, which was corrected in the transplanted WT HSPC-transplanted YG8R mice (FIG. 3B). These data represent further evidence of mitochondrial dysfunction in the YG8R mice, which is normalized in the treated mice.

Figure 3C:
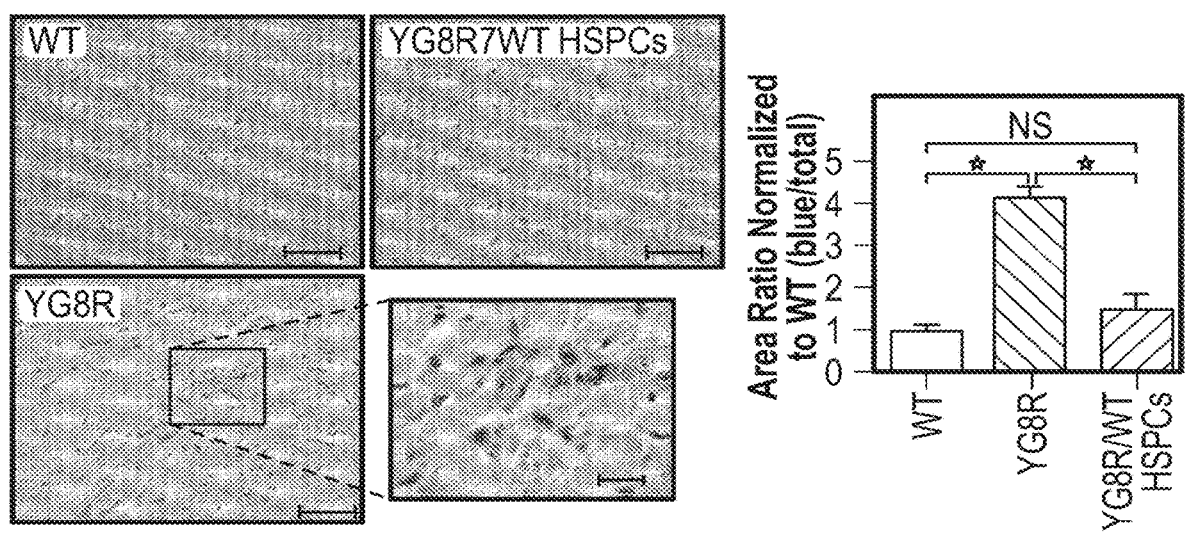

In addition to neurological deficits, FRDA patients also develop a progressive hypertrophic cardiomyopathy. Thus, the potential impact of HSPC transplantation on heart pathology in YG8R mice was investigated. However, as cardiomyopathy is very mild in this mouse model, no significant phenotype was found in the YG8R mice compared to WT at 9 months of age. A significant indicator of cellular iron metabolism dysregulation is the presence of iron deposits. Iron deposits in cardiomyocytes were observed in FRDA patients and in old (14-18 months) YG22 mice. Perl's staining of heart sections did not reveal any iron deposit in 9-month old YG8R mice as expected. Thus, the test was performed in older mice (18 month old), and iron deposition in cardiomyocytes were present in the non-treated YG8R or transplanted with YG8R HSPCs mice, while significantly decreased in YG8R/WT HSPCs mice (FIG. 3C). These data show the capacity of WT HSPC transplantation to correct mitochondrial iron metabolism in YG8R mice.

Figure 3G:
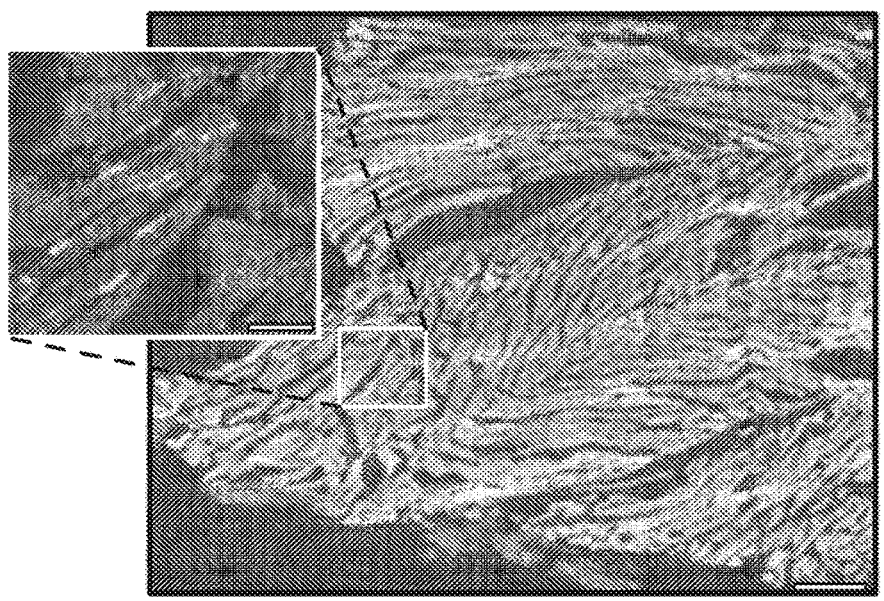
Figure 7A:
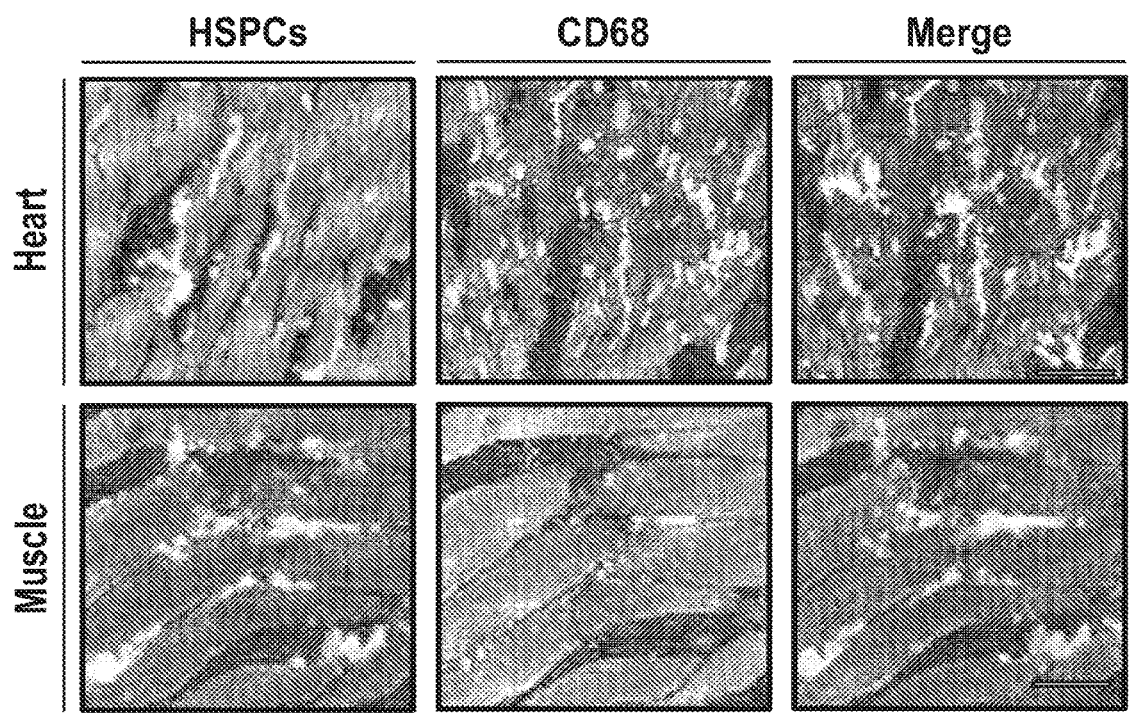
FIGS. 7A and 7B are pictorial diagrams showing that HSPCs differentiate into macrophages in heart and muscle. Confocal images of heart and skeletal muscle section from YG8R transplanted with WT GFP+ HSPCs after labeling with anti-GFP, anti-CD68 (FIG. 7A) anti-MHCII (FIG. 7B), Phalloidin and DAPI. Scale bar, 30 μm.
Figure 7B:
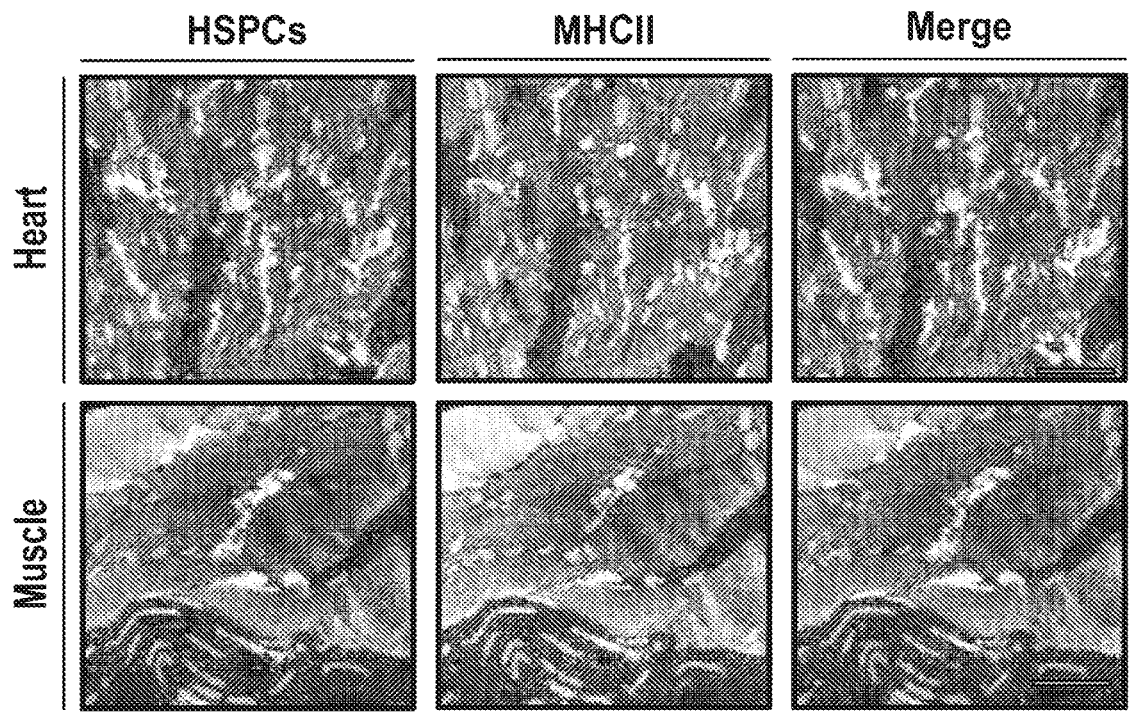

In both heart and skeletal muscle tissues, levels of mFxn expression were increased in the WT HSPC-treated mice compared to YG8R controls (FIGS. 3D and 3E) and confocal microscopy analysis revealed a high level of GFP$^+$ cells engrafted in these tissues in HSPC-transplanted YG8R animals (FIGS. 3F and 3G). The engrafted GFP$^+$ cells expressed CD68 and MHCII (FIGS. 7A and 7B), indicating that these cells are macrophages. Taken together, these data indicate that HSPC-derived cells integrate into the heart and skeletal muscle and differentiate into macrophages in YG8R mice.

Figure 3H:
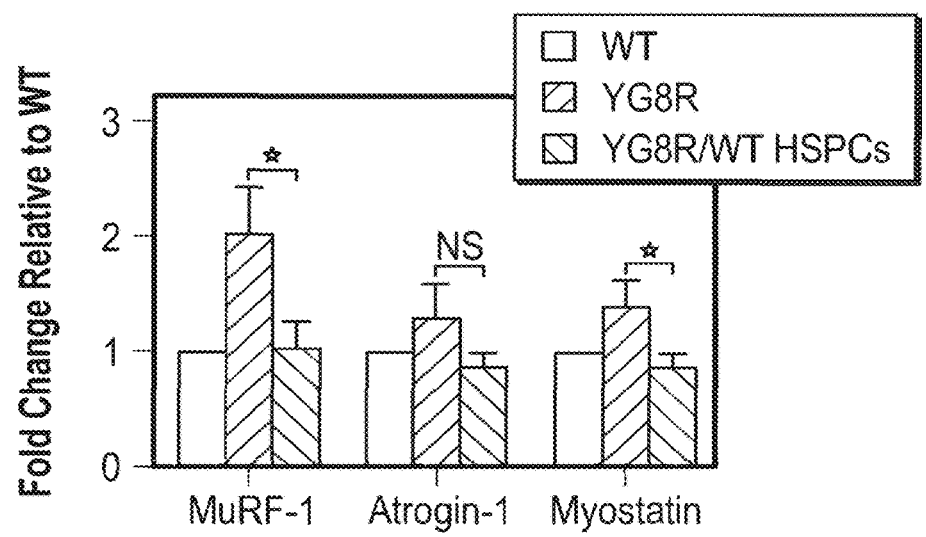

Muscle strength was also observed to be significantly impaired in YG8R mice and normal in the WT HSPC-transplanted YG8R mice. To investigate potential muscular atrophy in YG8R mice, the expression levels were measured of two muscle-specific E3 ubiquitin lagases, Muscle RING finger 1 (MuRF-1) and F-box (MAFbx)/atrogin-1, and a member of the transforming growth factor-β superfamily, myostatin, which are increased in each type of skeletal muscle atrophy. MuRF-1, atrogin-1 and myostatin expression was increased in skeletal muscle from YG8R mice compared to WT (although not significant for Atrogin 1), whereas the levels were normal in the treated YG8R mice (FIG. 3H), demonstrating the rescue of this defect by HSPC transplantation.

Figure 4A:
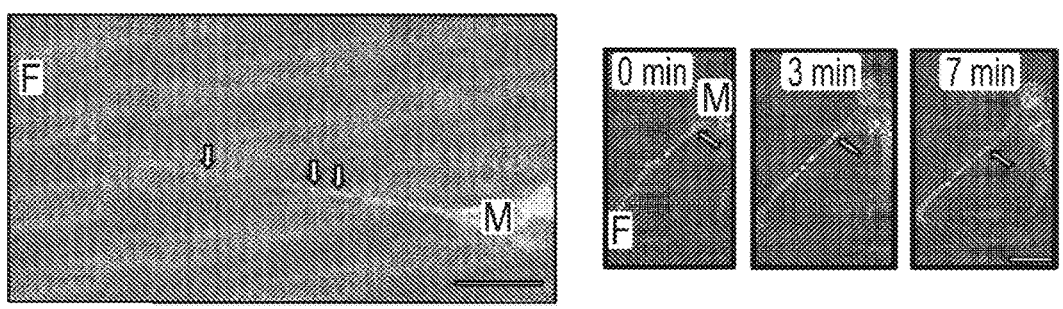
FIGS. 4A-4F are pictorial and graphical diagrams showing that HSPC-derived cells deliver frataxin-bearing mitochondria to the diseased cells in vitro and in vivo.
Figure 4B:
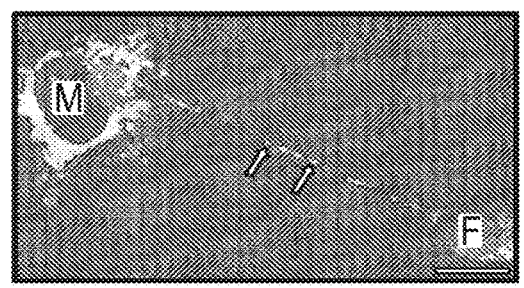

Macrophages deliver frataxin-bearing mitochondria to diseased cells via tunneling nanotubes in vitro. It has been previously reported in the context of the lysosomal storage disorder cystinosis, that HSPC-derived macrophages promote functional rescue of diseased cells through a lysosomal cross-corrective mechanism via TNTs. Hence, it was investigated whether phagocytic cells could also mediate the transfer of frataxin-bearing mitochondria into mfxn$^{-/-}$ hFXN$^+$ cells via similar route. Fibroblasts harvested from YG8R neonate skin were co-cultured with macrophages isolated from the bone marrow of Cox8-GFP DsRed mice, ubiquitously expressing the mitochondrial Cox8 protein fused to GFP alongside the cytosolic DsRed reporter gene. Using live imaging, it was observed that GFP$^+$ mitochondria were transferred from the DsRed-expressing macrophages to the mfxn$^{-/-}$ hFXN$^+$ fibroblasts via long tubular protrusions (FIG. 4A). In parallel, macrophages stably transduced with a lentiviral vector containing the human mitochondrial frataxin tagged with GFP (LV-hFXN-GFP) were used. Mitochondria were then labeled with red MitoTracker in the co-culture assay. Transfer of hFXN-GFP-bearing mitochondria via TNTs was observed from the macrophages to the diseased fibroblasts (FIG. 4B). Together, these results demonstrate the ability of macrophages to transfer frataxin-bearing mitochondria to FRDA cells via TNTs, suggesting a potential mechanism of rescue by HSPC-derived cells in the YG8R model.

Figure 4C:
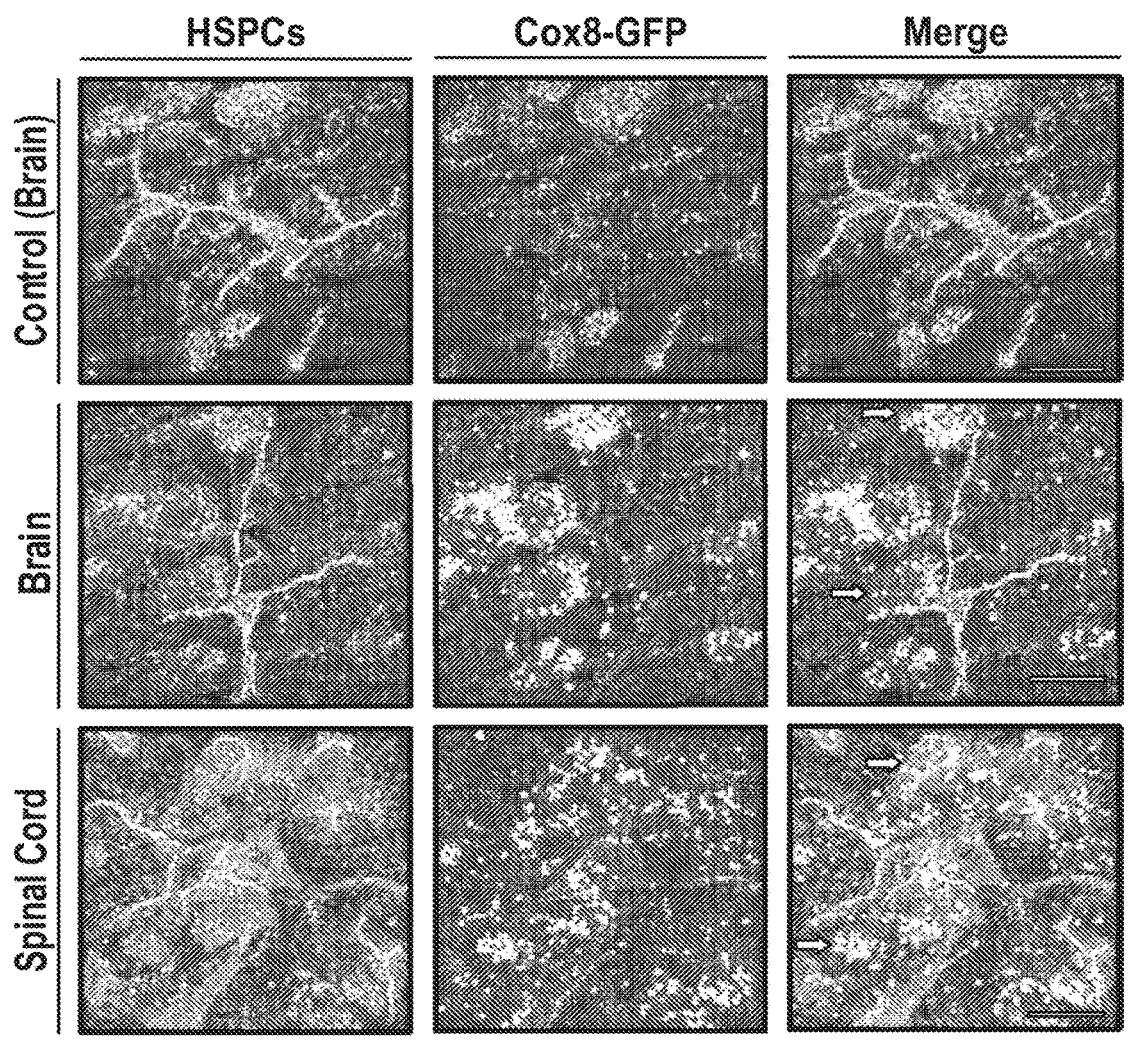
Figure 4D:
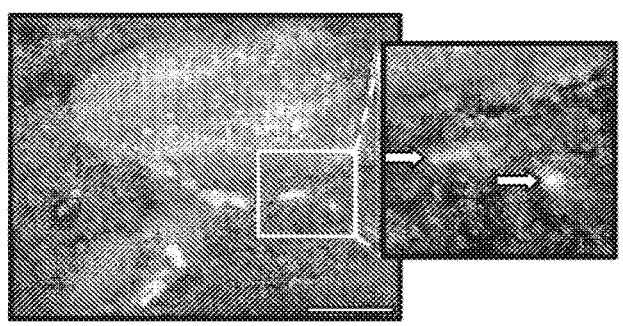
Figure 4E:
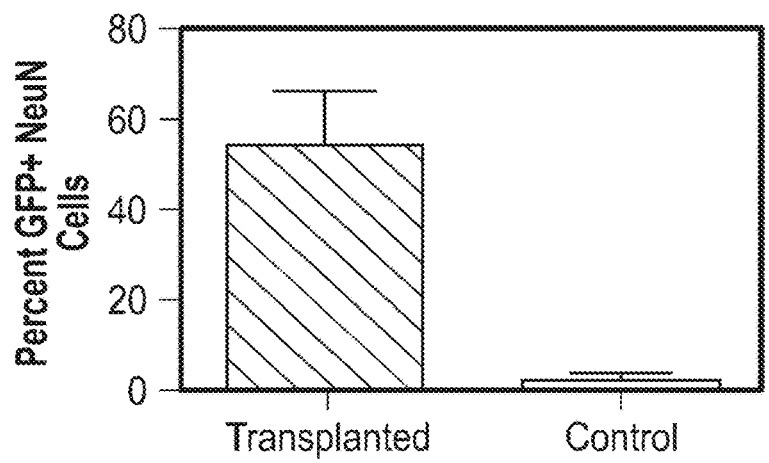
Figure 4F:
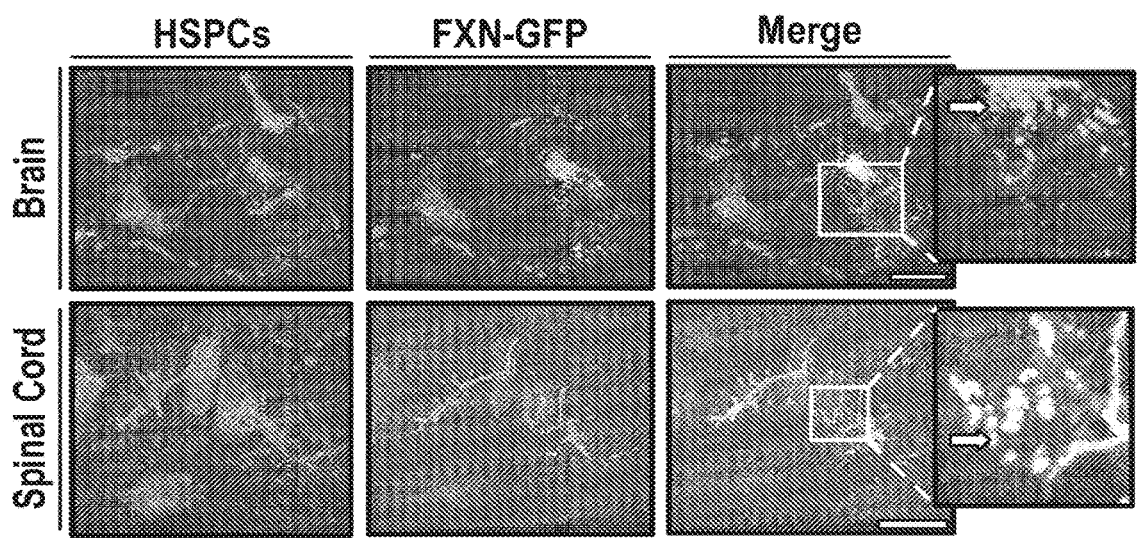
Figure 8:
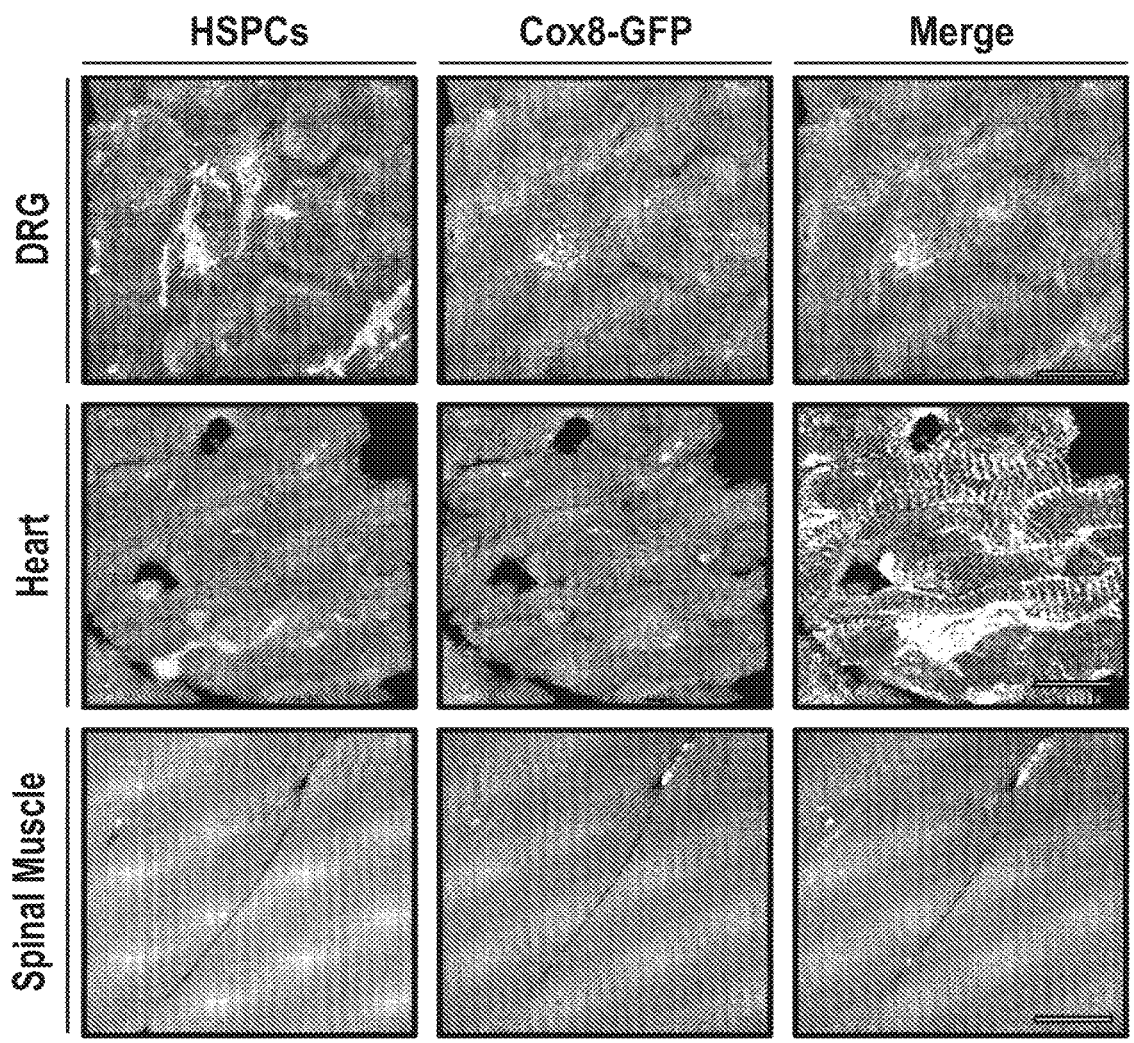
FIG. 8 is a pictorial diagram showing that HSPC-derived macrophages deliver mitochondria to neurons in DRG and to myocytes in heart and skeletal muscle. Representative confocal images of DRG, heart and skeletal muscle from an YG8R mouse transplanted with DsRed$^+$/Cox8-GFP$^+$ HSPCs at 7 months post-transplantation stained with anti-NeuN (DRG), anti-α-Actinin (heart) or Palloidin (muscle), and DAPI (heart and muscle). Scale bars, 10 μm.
Figure 9A:
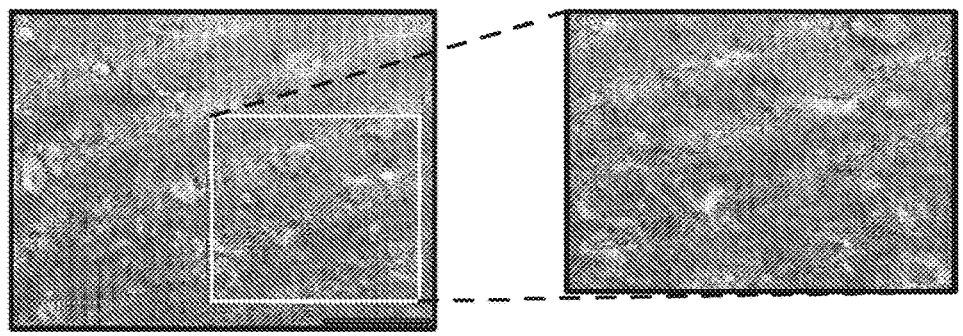
FIGS. 9A-9D are pictorial and graphical diagrams showing quantification of Cox8-GFP transfer from HSPC-derived microglia to neurons.
Figure 9B:
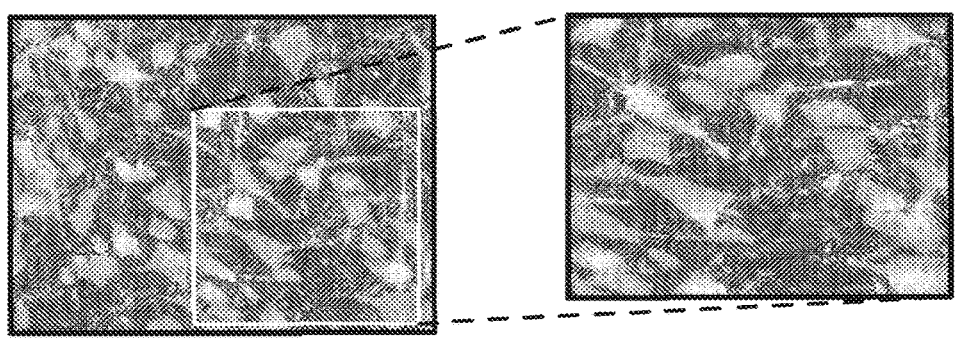
Figure 9C:
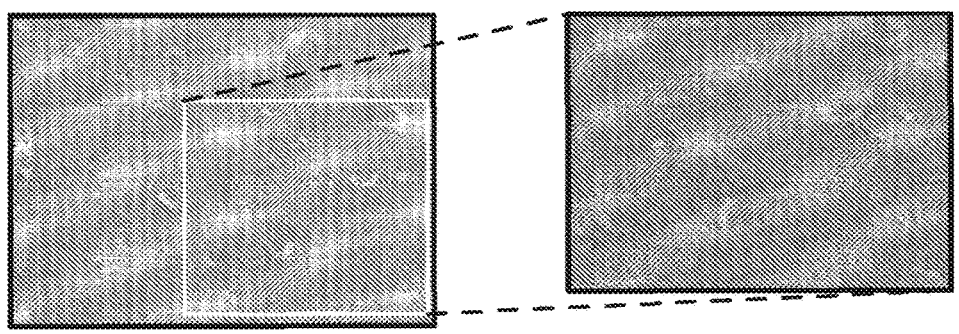
Figure 9D:
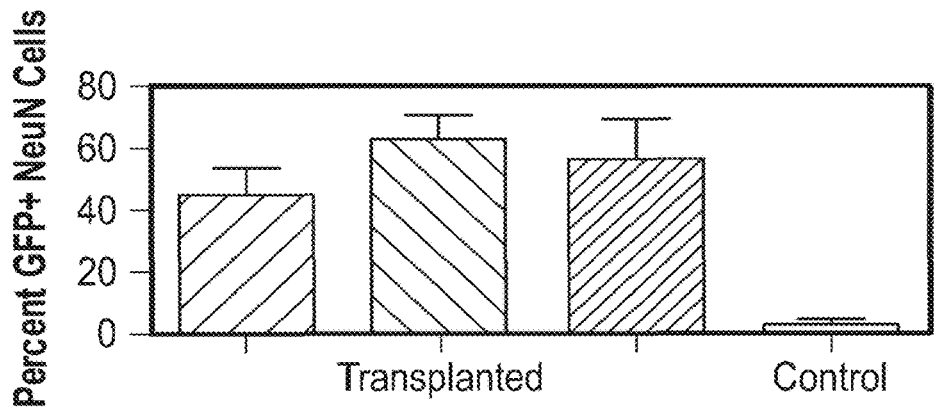

HSPC-derived microglial cells macrophages enable neuronal and muscular cross-correction in vivo. To assess whether transfer of mitochondrial proteins occurs in vivo, YG8R mice were transplanted with HPSCs isolated from DsRed Cox8-GFP mice. Cox8-GFP punctae were detected within the DsRed-expressing microglial cells but also within neurons in brain, spinal cord and DRGs (FIGS. 4C and 8). It was observed that neurons containing Cox8-GFP were in contact with one or more DsRed$^+$ microglial branch extensions (FIG. 4C) and GFP$^+$ punctae were also observed within these microglial processes (FIG. 4D). These data suggest the involvement of the microglial membrane projections in the transfer of Cox8-GFP proteins from HSPC-derived microglia to host neurons. Quantification in spinal cord tissue revealed that about 50% of neurons contained Cox8-GFP (FIGS. 4E and 9A-9D). Cross-correction of frataxin from microglia to neurons was also demonstrated by transplanting YG8R mice with HSPCs isolated from DsRed-transgenic mice and stably transduced with LV-hFXN-GFP (FIG. 4F). In addition, evidence of transfer was apparent in heart and skeletal muscle, in which Cox8-GFP was detected in host cardiac/muscular myocytes in apposition to graft-derived macrophages (FIG. 8). Together, these results represent the first demonstration of mitochondrial protein transfer from microglia to neuronal cells and provide strong indication that cross-correction is involved in HSPC-mediated rescue of FRDA phenotype in this animal model.

pCCL-FXN Constructs and In Vitro Testing. For developing a HSC gene therapy approach for FRDA, pCCL-EFS-X-WPRE (pCCL) LV were used. This vector backbone is the one used for the future clinical trial for cystinosis. A central polypurine tract (cPPT) fragment that increases the nuclear import of viral DNA was added to the CCL vector backbone. A Woodchuck hepatitis virus Posttranslational Regulatory Element (WPRE) is present to boost titer and gene expression. However, its open-reading frame was eliminated because it overlapped with the woodchuck hepatitis virus X protein, a transcriptional activator involved in the development of liver tumors. Transgene expression is driven by the ubiquitously expressed short intron-less human Elongation Factor 1 alpha promoter (EFS, 242 bp). The human FXN cDNA (633 bp), corresponding to the canonical frataxin (isoform I, FXN I) found in mitochondria, was amplified by PCR and inserted into pCCL generating pCCL-EFS-hFXN (FIG. 5A), and upstream eGFP generating pCCL-EFS-hFXNeGFP. Additionally, a lentviral construct that carries Cas9 enzyme and guide RNA was generated to remove the expansion of GAA repeats in the first intron of frataxin gene. The integrity of the constructs was verified by sequencing and restriction enzyme digestion. LV virus particles were produced and titered as previously described.

YG8R fibroblasts were transduced with pCCL-EFShFXNeGFP, resulting in ~100% GFP$^+$ cells, which were tested for their functional rescue. It was reported that frataxin deficiency results in increased cell susceptibility to $H_2O_2$ toxicity. Compared to WT fibroblasts, significant reduction in cell survival after exposure to $H_2O_2$ was observed in YG8R fibroblasts. Improved survival was demonstrated in the FXN-GFP-transduced fibroblasts compared to YG8R controls but did not reach the WT level (FIG. 5B).

The data provided herein demonstrates that neurological and muscular pathology can be fully prevented in the YG8R mice transplanted with WT HSPCs at 2 months of age. Finally, the data suggests that the mechanism involved in this rescue is the transfer of frataxin-bearing mitochondria from the HSPC-derived phagocytic cells to the diseased cells via TNTs.

Example 2

Materials and Methods

Animals. YG8R mice with a deletion of murine Fxn gene (mFxn) and expressing mutant human FX gene (hFXN) containing 190+90 GAA repeat expansion were generated in a C57BL/6J background as previously described (Al-Mahdawi, et al., GAA repeat instability in Friedreich ataxia YAC transgenic mice. *Genomics* 84, 301-310 (2004); Al-Mahdawi, et al., GAA repeat expansion mutation mouse models of Friedreich ataxia exhibit oxidative stress leading to progressive neuronal and cardiac pathology. Genomics 88, 580-590 (2006), both of which are incorporated herein by reference). Breeding pairs consisted of females heterozygous for Fxn and males heterozygous for Fxn and hemizygous for FXA (B6.Cg-Fxntm1Mkn Tg(FXN)YG8Pook/J), and were purchased from Jackson Laboratory (Bar Harbor, ME). YG8R mice and wild-type (WT) mice used as controls for these studies were obtained from these breeders. Genotyping was performed using the following primers:

```
mfxn-F:
                                     (SEQ ID NO: 5)
5'-CTTCCCTCTACCCTGCCTTC-3' mfxn-R:
                                     (SEQ ID NO: 6)
5'-GGAGAACAGTGGACACAGTAACA-3'

PGK-NEO:
                                     (SEQ ID NO: 7)
5'-CATCGCCTTCTATCGCCTTCT-3'

FXN-F:
```

-continued

FXN-R:
(SEQ ID NO: 8)
5'-GGGCAGATAAAGGAAGGAGATAC-3'

(SEQ ID NO: 9)
5'-ACGATAGGGCAACACCAATAA-3'.

Transgenic mice constitutively expressing GFP (C57BL/6-Tg(ACTB-EGFP)1Osb/J) or DsRed (B6.Cg-Tg(CAG-DsRed*MST)1Nagy/J) were also purchased from Jackson Laboratory. The mtGFP-Tg transgenic mice (C57BL/6J-Tg (CAG-Cox8/EGFP)49Rin) expressing the Cox8-GFP mitochondrial fusion protein were purchased from the RIKEN BioResource Center through the National Bio-Resource Project of the MEXT (Wako, Saitama, Japan). mtGFP-Tg mice were backcrossed with Dsred-Tg mice to produce DsRed-mtGFP-tg mice. Genotyping for mt-GFP was done by PCR as previously described (Shitara, et al., Non-invasive visualization of sperm mitochondria behavior in transgenic mice with introduced green fluorescent protein (GFP). *FEBS Lett* 500, 7-11 (2001)). Mice were maintained in a temperature- and humidity-controlled animal facility, with a 12-h light-dark cycle and free access to water and food. Both male and female mice were used in all experiments.

Frataxin-GFP lentivirus construction, production and titer. The Self Inactivated (SIN)-lentivirus vector (LV), pCCL-EFS-X-WPRE-GFP (pCCL-GFP) was used for stable gene transfer in HSPCs and macrophages. The vector backbone contains the intron-less human elongation factor 1a promoter to drive transgene expression. The human FXN cDNA (Clone ID 5300379, GE Healthcare; 633 bp) corresponding to the canonical frataxin (isoform I, FXN I) found in mitochondria (Perez-Luz, et al., Delivery of the 135 kb human frataxin genomic DNA locus gives rise to different frataxin isoforms. *Genomics* 106, 76-82 (2015), incorporated herein by reference) was amplified by PCR using the following primers: F: 5'-TTAGGATC-CATGTGGACTCTCG-3' (SEQ ID NO: 10) and R: 5'-AGAGGATCCAGCATCTTTTCCG-3' (SEQ ID NO: 11); and inserted into pCCL at the BamH1 restriction site in phase with the GFP cDNA. LV were produced and titered as previously described (Harrison, et al., Hematopoietic stem cell gene therapy for the multisystemic lysosomal storage disorder cystinosis. *Mol Ther* 21, 433-444 (2013), incorporated herein by reference).

Bone marrow cell isolation, transduction transplantation and engraftment determination. Bone marrow cells were flushed from the femurs of 6-8 week old YG8R mice, GFP transgenic mice, DsRed transgenic mice or DsRed mt-GFP transgenic mice. Hematopoietic stem and progenitor cells (HSPCs) were isolated by immunomagnetic separation using anti-Sca1 antibody conjugated to magnetic beads (Miltenyi Biotec, Auburn, CA). Sca1$^+$ cells were directly transplanted by tail vein injection of 1×10$^6$ cells re-suspended in 100 µl of PBS into lethally irradiated (7 Gy; X-Rad 320, PXi) YG8R mice. Prior to transplantation, Sca1$^+$ cells from the DsRed transgenic mice were first transduced with LV-hFXN-GFP using a multiplicity of infection (MOI) of 10 in presence of polybrene (4 mg/mL) in retronectin-coated (20 g/mL) 24-well plates at a density of 2×10$^6$ cells per well for 16 hours in StemSpan medium (StemCell Technologies) supplemented with SCF, TPO, FLT3 ligand (100 ng/mL each), and IL6 (20 ng/mL) cytokines (PeproTech). Bone marrow cell engraftment of the transplanted cells was measured in peripheral blood 2 months post-transplantation; blood samples freshly harvested from the tails were treated with red blood cell lysis buffer (eBioscience, San Diego, CA) and subsequently analyzed by flow cytometry (BD Accuri C6, BD Biosciences) to determine the proportion of GFP- or DsRed-expressing cells.

Behavioral tests. WT mice, YG8R mice, YG8R mice transplanted with mfxn$^{-/-}$ hFXN$^+$ HSPCs, and YG8R mice transplanted with either WT GFP or DsRed/mt-GFP HSPCs were tested at both 5 and 9 months of age before being sacrificed for tissue analysis. Rotarod analysis was performed using a Roto-rod Series 8 apparatus (Ugo Basille, Comerio, Italy). The rod was a knurled plastic dowel (6.0 cm diameter) set at a height of 30 cm. During training the mice were placed on the stationary rotarod for 30 sec before the trial was initiated. Then each mouse was given 4 trials per day, with a 60 sec inter-trial interval on the accelerating rotarod (4-40 rpm over 5 min). The latency to fall was recorded for each trial. Locomotor activity was measured using an automated monitoring system (Kinder Associates, San Diego, CA). Polycarbonate cages (42×22×20 cm) containing a thin layer of bedding material were placed into frames (25.5×47 cm) mounted with photocell beams. Each mouse was placed into the open field and all movements were recorded over a 60-second testing period. Grip strength was measured using a device consisting of a 10 cm long T-shaped bar connected to a digital dynamometer (Ugo Basile, Comerio, Italy). Animals were held by the tail and placed before the bar, allowed to grip the bar with their forelimbs, and then gently pulled backwards until the bar was released. Ten consecutive measurements were made for each animal and both the average and maximal readouts were recorded. Gait measure (stride length) was collected using an automated gait analysis system (CatWalk (Noldus Instruments)). Animals were placed at one end of the walkway and allowed to run down the length of the walkway, as two light sources illuminated the surface contact of paws with the glass floor, producing an image of a paw print. During locomotion, the glass walkway was filmed from below by a video camera. The CatWalk software program was used to analyze recorded footage, define individual paw prints (e.g., left forepaw, right hindpaw), and give readouts of multiple parameters of gait. Testing was administered daily for 5 days. Only unbroken bouts of locomotion, during which animals ran down the walkway at a consistent speed, were used for analysis.

Primary fibroblast and macrophage isolation, and transduction. Fibroblasts were generated from skin biopsies of neonate of YG8R mice. Cultures were maintained using high-glucose DMEM (Dulbecco's modified Eagle's medium; Life Technologies, Carlsbad, CA) supplemented with 10% fetal bovine serum (FBS; Gibco, Life Technologies) and 1% penicillin/streptomycin (PenStrep; Gibco) at 37° C. under 5% CO$_2$. Primary macrophages from DsRed mt-GFP mice were derived from bone marrow cells. Bone marrow cells were flushed from the femurs of 6-8 week old mice and kept in culture in RPMI medium with 10% FBS, 1% PenStrep and 10% L929 conditioned medium 29 at 37° C. under 5% CO$^2$. For macrophage transduction with pCCL-FXN-eGFP, the IC-21 macrophage cell line was used (American Type Culture Collection, catalog #TIB-186) and cultured in RPMI 1640 medium (Gibco). Six-well plates were coated with retronectin (20 l/ml; Takara Bio) following the manufacturer's instructions. IC-21 macrophages were plated at 250,000 cells in 2 ml per well and transduced with pCCLFXN-eGFP using a MOI of 15. Media was changed 24 hours after transduction.

Live imaging. YG8R fibroblasts were co-cultured with DsRed Cox8-GFP or macrophages stably transduced with a lentivirus expressing hFXN-GFP as previously described (Naphade, et al., Brief reports: lysosomal cross-correction by hematopoietic stem cell-derived macrophages via tunneling nanotubes. *Stem Cells* 33, 301-309 (2015), incorporated herein by reference). Briefly, 75,000 fibroblasts were co-cultured with equal number of macrophages in glass-bottomed culture dishes (MatTek Corp, Ashland, MA). hFXN-GFP co-cultures were stained with 50 nM MitoTracker (Invitrogen) for 45 minutes prior to imaging. Confocal live imaging was performed 1 and 2 days later using Perkin Elmer UltraView Vox Spinning Disk Confocal with X40 (Numerical aperture (NA)=1.30) and X60 (NA=1.42) oil objective at 37° C. under 5% $CO_2$. Images were captured, processed, and analyzed using Velocity Software (Perkin Elmer, Waltham, MA).

Mouse frataxin quantitative RT-PCR. Total RNA was prepared from snap-frozen skeletal muscle, brain and heart biopsies using the RNeasy Lipid and Fibrous Tissue kits (Qiagen) according to manufacturer's instructions. cDNA was then prepared using iScript cDNA Synthesis kit (Bio-Rad). Commercial TaqMan probes specific to mouse frataxin were employed to quantitate expression (Applied Biosystems).

Oxidative stress detection. Protein lysates from tissues directly snap-frozen in liquid nitrogen after dissection were prepared using RIPA buffer (Sigma) containing proteases inhibitors (Roche) as previously described (Campuzano, et al., Frataxin is reduced in Friedreich ataxia patients and is associated with mitochondrial membranes. *Human molecular genetics* 6, 1771-1780 (1997), incorporated herein by reference). For each assay, g of protein was used after total protein concentration was determined using the BCA assay. Proteins were then derivatized by adding 1×2,4-Dinitrophenylhydrazine (DNPH) solution contained in the OxyBlot Protein Oxidation Detection kit (Chemicon International) according to manufacturer's instructions. Samples were applied to electrophoresis and transferred to a PVDF membrane. After blocking with 1% BSA/PBS-T, membrane was incubated with Rabbit anti-Dinitrophenyl (DNP) antibody followed by a Goat anti-rabbit HRP conjugate, and visualized using ECL kit (Pierce). Protein levels were normalized using an anti-Tubulin (ab6161, Abcam) antibody and band intensity was quantified using ImagePro software (Media Cybernetics).

Mouse Mitochondria RT2 Profiler PCR Array. RNA was isolated from the cerebrum using the RNeasy Lipid Tissue Mini Kit (Qiagen) and 0.5 µg was then reverse transcribed with the iScript cDNA Synthesis Kit (Bio-rad). Samples were mixed with SYBR green and equally loaded into all wells of the Mouse Mitochondria RT2 Profiler PCR Array (Qiagen, Cat. no. PAMM-087Z) and amplified per manufacture's recommendation on the CFX96 Thermocycler (Bio-rad). Ct data was exported and fold change calculated using the delta Ct method between sample genes and a panel of housekeeping controls.

Lactate Pyruvate analysis. Muscle biopsies (10 mg) were homogenized in ice in 1 ml of ice cold 40% acetonitrile (containing 0.1% formic acid)/40% methanol/20% $H_2O$) using a tissue grinder (dounce), followed by centrifugation for 10 minutes at 13,000×g. The extraction solution contained stable isotope of lactate ($^{13}C_3$ sodium-lactate, Cambridge Isotope Laboratories, Inc.). Supernatants were removed, dried in a speed vac/lyophilizer system, and re-suspended in 150 µl 0.1% formic acid. Pellets were re-dissolved in 0.1N NaOH and protein content measured using a bicinchoninic acid (BCA assay). 5 µl of each resuspended supernatant was injected on a C18-pfp HPLC column (Mac-Mode Analytical, Chadds Ford, PA), as previously described (Gertsman, et al., Validation of a dual LC-HRMS platform for clinical metabolic diagnosis in serum, bridging quantitative analysis and untargeted metabolomics. *Metabolomics* 10, 312-323 (2014), incorporated herein by reference), and coupled to an API-4000 triple quadrupole mass spectrometer (AB Sciex). MRM (molecular reaction monitoring) for lactate (89>43), $^{13}C_3$-lactate (92>45), and pyruvate (87>43 and 87>87) were used during the acquisition. Lactate and pyruvate peaks were both normalized to $^{13}C_3$ lactate. Both lactate and pyruvate were further normalized to protein content (mg) prior to calculation of the final lactate/pyruvate (L/P) peak area ratios used in FIG. 3B. Since the ratio is expressed in terms of normalized peak areas, the ratio values should not be confused with those determined from absolute concentration measurements as performed in previous studies measuring L/P, but still effective for examining relative differences between cohorts.

Vacuole imaging and quantification. Dorsal root ganglia (DRG) from lumbar level 5 (L5) were collected, sectioned at 30 µm intervals using a cryostat, and mounted on gelatin-coated slides. DRG sections were stained with thionin (Nissl stain) for visualization of neuronal cell bodies. Three DRGs per subject were acquired at 60× magnification using a BZ-X700 fluorescent microscope (Keyence). The presence of vacuoles in each DRG was traced and measured by a blinded experimenter in duplicate using ImageJ; vacuoles were defined as extremely circular white (Nissl negative) areas with smooth edges within DRG neurons. Number of vacuoles and area of vacuolar space relative to entire area of each DRG section was compared across genotypes.

Heart histology and iron quantification. For histological preparations, terminally anesthetized mice were fixed by intracardial perfusion with 10% formalin. Fixed tissues were dissected, embedded in paraffin wax, and sectioned by standard methods. Sections were deparaffinized and stained using Perl's technique to detect ferric iron as previously described (Al-Mahdawi, et al., GAA repeat expansion mutation mouse models of Friedreich ataxia exhibit oxidative stress leading to progressive neuronal and cardiac pathology. *Genomics* 88, 580-590 (2006)). Whole heart sections were imaged on the Keyence Fluorescence Microscope and a single wide-field image stitched together. Using ImagePro Preimier Software (MediaCybernetics), levels of iron staining were assessed by isolating the blue channel, measuring the area of signal and then dividing from total area of the section. Values were reported normalized to wild-type levels.

Immunofluorescence and image acquisition. Heart and muscle tissues were fixed in 5% paraformaldehyde, equilibrated in 20% sucrose overnight and frozen in Tissue-Tek Optimal Cutting Temperature (OCT) medium at −80° C. (Sakura Finetek U.S.A, Torrance, CA); 10 µm sections were cut. DRG, brain, and spinal cord tissue were fixed in paraformaldehyde, cryopreserved in 30% sucrose, and frozen in OCT medium. For DRGs, tissue was cut into 20 µm sections and directly mounted to gelatin-coated slides. For brain and spinal cord, tissue was sectioned to 30 µm and collected as free-floating sections. For immunofluorescence, tissues were incubated with the following antibodies: rat anti-CD68 (1:100; BioLegend 137001), Biotin rat anti-MHCII (1:100; BD Pharmigen 553622), rabbit anti-GFP (1:500; Abcam ab290), chicken anti-GFP (1:1500, Abcam ab13970), rabbit anti-Iba1 (1:1500; Wako #019-19741), goat anti-mCherry (1:1000, Sicgen AB0040), mouse anti-NeuN (1:500; Millipore MAB377), rabbit anti-MBP (1:200, Millipore AB980), mouse anti-NF200 (1:500, Millipore MAB5262), mouse anti-α-Actinin (1:400; Sigma), Rabbit anti-von Willibrand factor (1:300; Chemicon), DAPI (1:500; Molecular Probes), Bodipy-Phalloidin (1:100; Molecular Probes). The appropriate AlexaFluor-conjugated secondary antibodies (Invitrogen) were used for visualization of antigens. Images were acquired using the LSM 880 with Airyscan confocal microscope (Zeiss), a Keyence BZ-X710 digital microscope system for high resolution stitching images of tissue sections, or an Olympus FV1000 confocal microscope for live imaging. Confocal image stacks were analyzed with IMARIS Software (Bitplane, Oxford Instruments).

Quantification of neuronal cross-correction. The entire gray matter region of lumbar spinal cord sections from three YG8R mice transplanted with Cox8-GFP HSPCs and an untransplanted control were stained with NeuN and imaged at 20× on the LSM 880 confocal microscope (Zeiss). NeuN+ neuronal cells were outlined and counted using ImagePro Plus software (Media Cybernetics) and then assessed for GFP positivity which was reported as a percentage of total NeuN cells (FIG. 8). All acquisition, filtration and processing steps were performed identically on the GFP channel between all samples.

Clearing of mouse spinal cord. A 6-mm segment of cervical spinal cord from a mouse at 3 months post-transplantation with DsRed+ HSPCs was processed for optical clearing as previously described (Chung, et al., Structural and molecular interrogation of intact biological systems. Nature 497, 332-337 (2013), incorporated herein by reference). Briefly, PFA-fixed tissue was infused with hydrogel monomer solution (4% PFA, 4% acrylamide, 0.05% bis-acrylamide) and thermally polymerized. Lipids were then passively extracted in SDS-containing borate buffer at 37° C. for 4 weeks, until tissue was cleared. Clarified tissue was incubated in Rapidclear CS for 1 day and mounted using a Wilco dish. Tissues were then imaged using an Olympus FV1200 system equipped with a 10× water-immersion objective (numerical aperture: 0.6; working distance: 3 mm; stack size: 1.65 mm; step size, 5 μm).

Statistics. No animals were excluded from the experiments. Experimenters were blinded to the genotype of the specific sample to every extent possible. Power calculation analysis was not performed. All data displayed normal variance except DRG vacuole measurements. For normal data and mitochondrial PCR array data, one-way analysis of variance (ANOVA) was performed, followed by post-hoc Student's t-test to determine statistical significance using GraphPad Prism 7.01 (GraphPad Software, La Jolla, CA). Oxidative stress measurements employed one-tailed t-tests with the assumption that YG8R oxidation levels would be higher. For vacuole measurements, the Mann-Whitney non-parametric test corrected for multiple testing by the Bonferroni correction was used. In vitro experiments were performed in biological triplicates. Error bars denote s.e.m. The level of significance is indicated as follows: *P<0.05, P<0.01, *P<0.005.

Although the invention has been described with reference to the above examples, it will be understood that modifications and variations are encompassed within the spirit and scope of the invention. Accordingly, the invention is limited only by the following claims.

What is claimed is:

1. A method of treating a mitochondrial disease or disorder in a subject comprising:
   (a) contacting a hematopoietic stem and progenitor cell (HSPC) from the subject expressing a dysfunctional endogenous human frataxin (hFXN) gene or reduced levels of hFXN mRNA with a gene editing system to produce a functional hFXN gene,
   wherein the dysfunctional endogenous hFXN gene comprises a trinucleotide extension mutation, and
   wherein following contacting the HSPC, the gene editing system removes the trinucleotide extension mutation in the dysfunctional endogenous hFXN gene, thereby producing HSPCs expressing a functional hFXN gene; and
   (b) transplanting the HSPCs expressing the functional hFXN gene into the subject,
   wherein upon transplantation into the subject, the HSPCs transfer a functional hFXN gene, a functional hFXN mRNA, a functional protein or a combination thereof from the HSPC or a cell differentiated therefrom to a cell in a tissue or to the central nervous system (CNS) correcting neurologic, cardiac and/or muscular complications within about 6-12 months post-transplantation, thereby treating the mitochondrial disease or disorder.

2. The method of claim 1, wherein the gene editing system is selected from the group consisting of CRISPR/Cas, zinc finger nucleases, and transcription activator-like effector nucleases.

3. The method of claim 1, wherein the mitochondrial disease or disorder is Friedreich's ataxia (FRDA).

4. The method of claim 1, wherein the subject is a mammal.

5. The method of claim 4, wherein the mammal is a human.

6. The method of claim 1, wherein the gene editing system is transfected to the cell by a vector selected from the group consisting of a lentiviral vector, a herpes simplex virus type 1 (HSV-1) vector, an adenoviral vector, a DNA-based adenoviral vector, an RNA-based retroviral vector, and an adeno-associated virus (AAV) vector.

7. The method of claim 6, wherein the vector is a self-inactivating (SIN) lentivirus vector.

8. The method of claim 1, wherein the differentiated cell is a microglial cell or a macrophage.

9. The method of claim 1, wherein the HSPC or differentiated cell transfers a functional hFXN protein, a functional hFXN gene, a functional hFXN mRNA or a combination thereof to a cell expressing dysfunctional hFXN or reduced levels of hFXN mRNA through tunneling nanotube (TNT) intercellular connections from a HSPC-derived macrophage or microglial cell to the cell expressing a dysfunctional hFXN gene or mRNA.

10. The method of claim 9, wherein the cell expressing dysfunctional hFXN or reduced levels of hFXN mRNA is not differentiated from the HSPC providing the functional hFXN gene.

11. The method of claim 9, wherein the cell expressing dysfunctional hFXN or reduced levels of hFXN mRNA is any one of a muscular cell, a heart cell, a fibroblast, or a neuronal cell.

12. A method of transferring a functional hFXN gene, protein or mRNA to a cell expressing a dysfunctional hFXN gene or mRNA in a subject comprising:
  (a) contacting a hematopoietic stem and progenitor cell (HSPC) of the subject expressing a dysfunctional human frataxin (hFXN) gene or reduced levels of hFXN mRNA with a CRISPR/Cas gene editing system, wherein:
    (i) the dysfunctional hFXN gene comprises a trinucleotide extension mutation, and
    (ii) when expressed in the HSPC, the CRISPR/Cas gene editing system removes the trinucleotide extension mutation in the dysfunctional hFXN gene, thereby producing HSPCs expressing a functional hFXN gene or restoring levels of mRNA;
  (b) transplanting the HSPCs expressing the functional hFXN gene or mRNA into the subject, wherein:
    (i) upon transplantation into the subject, the HSPCs differentiate into a macrophage or a microglial cell in a brain, a spinal cord, a DRG, a skeletal muscle or a heart; and
    (ii) the macrophage or the microglial cell transfers a functional hFXN gene, protein, functional hFXN mRNA, or a combination thereof to a brain cell, a spinal cord cell, a DRG cell, a skeletal muscle cell, or a heart cell; or
    (iii) the HSPCs transfer a functional hFXN gene, protein, functional hFXN mRNA, or a combination thereof to a cell in a brain, spinal cord, DRG, skeletal muscle or heart;
  thereby transferring a functional hFXN gene, protein or mRNA to a cell expressing a dysfunctional hFXN gene or mRNA in the subject.

13. The method of claim 1 or claim 12, wherein the trinucleotide extension mutation is GAA.

14. The method of claim 2 or 12, wherein the CRISPR/Cas gene editing system is CRISPR/Cas9.

* * * * *